United States Patent
He et al.

(10) Patent No.: US 11,332,461 B2
(45) Date of Patent: May 17, 2022

(54) 2-(1H-PYRAZOL-3-YL) PHENOL COMPOUND AND USE THEREOF

(71) Applicant: BEIJING JIALIN PHARMACEUTICAL INC., Beijing (CN)

(72) Inventors: Wei He, Beijing (CN); Xiaoding Hou, Beijing (CN); E Liang, Beijing (CN); Hongbo Li, Beijing (CN); Bin Li, Beijing (CN); Le Guo, Beijing (CN); Shuang Yang, Beijing (CN)

(73) Assignee: BEIJING JIALIN PHARMACEUTICAL INC., Beijing (CN)

( * ) Notice: Subject to any disclaimer, the term of this patent is extended or adjusted under 35 U.S.C. 154(b) by 0 days.

(21) Appl. No.: 16/761,091

(22) PCT Filed: Oct. 22, 2018

(86) PCT No.: PCT/CN2018/111154
§ 371 (c)(1),
(2) Date: May 1, 2020

(87) PCT Pub. No.: WO2019/091277
PCT Pub. Date: May 16, 2019

(65) Prior Publication Data
US 2020/0354342 A1    Nov. 12, 2020

(30) Foreign Application Priority Data
Nov. 8, 2017  (CN) .......... 201711091268.0

(51) Int. Cl.
| | | |
|---|---|---|
| *C07D 403/10* | (2006.01) | |
| *C07D 231/12* | (2006.01) | |
| *C07D 401/10* | (2006.01) | |
| *C07D 403/06* | (2006.01) | |
| *C07D 403/12* | (2006.01) | |
| *C07D 413/12* | (2006.01) | |
| *C07D 471/08* | (2006.01) | |

(52) U.S. Cl.
CPC ......... *C07D 403/10* (2013.01); *C07D 231/12* (2013.01); *C07D 401/10* (2013.01); *C07D 403/06* (2013.01); *C07D 403/12* (2013.01); *C07D 413/12* (2013.01); *C07D 471/08* (2013.01)

(58) Field of Classification Search
None
See application file for complete search history.

(56) References Cited

FOREIGN PATENT DOCUMENTS

JP    WO 2006109680    * 10/2006 ........... C07D 231/12

* cited by examiner

*Primary Examiner* — Samantha L Shterengarts
(74) *Attorney, Agent, or Firm* — Platinum Intellectual Property LLP

(57) ABSTRACT

Provided are a compound of formula (I) or a pharmaceutically acceptable salt, stereoisomer, ether, ester, prodrug and solvate thereof. The compound can be used for preventing and/or treating cancers.

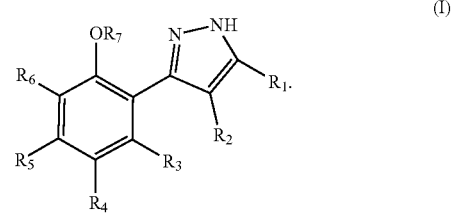

3 Claims, No Drawings

2-(1H-PYRAZOL-3-YL) PHENOL COMPOUND AND USE THEREOF

RELATED APPLICATIONS

This application is a United States National Stage Application filed under 35 U.S.C 371 of PCT Patent Application Serial No. PCT/CN2018/111154, filed Oct. 22, 2018, which claims Chinese Patent Application Serial No. CN 201711091268.0, filed Nov. 8, 2017, the disclosure of all of which are hereby incorporated by reference in their entirety.

FIELD

The present invention belongs to the field of medicine, and relates to a compound for preventing and/or treating cancers and a preparation method thereof.

BACKGROUND

BRG2 and BRM are core ATPase subunits of a mammalian chromatin remodeling complex SWI/SNF, have similar structures and are functionally complementary. An ATP hydrolase domain of the BRG1 can bind and hydrolyze ATP to provide energy, such that the chromatin remodeling complex binds to a chromatin to mediate DNA dissociation from a nucleosome, thereby regulating gene transcription. The C-terminus of the BRG1 is a reader domain of a histone code, which can specifically recognize acetylated lysines. This process is crucial for the binding of the chromatin remodeling complex to a correct chromatin site.

Studies suggest that, the BRG1 is involved in the regulation of some mutations in transcription related to tumorigenesis and tumor progression, such as CD44 and c-fos, and the BRG1 is an important tumor suppressor gene in the pathogenesis of cancers such as lung cancer, bladder cancer, breast cancer, prostate cancer, and gastric cancer. Furthermore, Takahiro Oike et al also reported that a BRM protein could be used as a candidate target site for the treatment of BRG1-deficient lung cancer. By an immunohistochemical analysis method, it shows that BRG1-deficiency and BRM overexpression are present in about 10% of patients with the non-small cell lung cancers (NSCLCs), and thus it proves the feasibility of therapies against the BRM target site, and the deficiency of the BRG1 also occurs in other cancers, including pancreatic cancer, skin cancer and brain cancer. For example, the BRG1 has recently been identified as a gene that frequently mutates in medulloblastoma, and thus a targeted therapy for a BRM protein can be applied to treatment of various cancers.

CN105523955A discloses a series of compounds for cancer treatment, especially for the treatment of NSCLCs with deficiency of the BRG1 gene. However, the compounds disclosed therein still have defects of insufficient activity and poor druggability, and especially for compounds of the 2-(1H-pyrazol-3-yl)phenol type, only alkyl substituent groups can be applied as substituents on the pyrazole ring, which greatly limits the application scope.

SUMMARY

An aspect of the present invention provides a compound represented by Formula (I) or a pharmaceutically acceptable salt, stereoisomer, ether, ester, prodrug and solvate thereof.

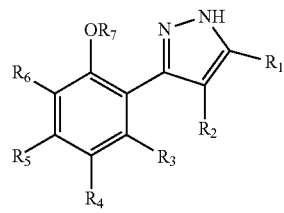

Formula (I)

wherein
when $R_1$ is selected from H, $C_{1-10}$ alkyl, $C_{2-10}$ alkenyl, $C_{2-10}$ alkynyl, $C_{3-10}$ cycloalkyl, $R_2$ is selected from $C_{2-10}$ alkenyl, $C_{2-10}$ alkynyl, where any carbon atom on alkyl, alkenyl or alkynyl can be substituted by one or more selected from groups consisting of: halogen, —CN, —$OC_{0-10}$ alkyl, —$S(O)_mC_{0-10}$ alkyl, —$SO_2N(C_{0-10}$ alkyl)($C_{0-10}$ alkyl), —$N(C_{0-10}$ alkyl)($C_{0-10}$ alkyl), —$N(C_{0-10}$ alkyl)C(=O)($C_{0-10}$ alkyl), —$N(C_{0-10}$ alkyl)C(=O)O($C_{0-10}$ alkyl), —$N(C_{0-10}$ alkyl)C(=O)N($C_{0-10}$ alkyl), —$C(=O)C_{0-10}$ alkyl, —$C(=O)OC_{0-10}$ alkyl, —$C(=O)N(C_{0-10}$ alkyl)($C_{0-10}$ alkyl), -heterocycloalkyl, —$N(C_{0-10}$ alkyl)heterocycloalkyl, —$N(C_{0-10}$ alkyl)aryl, —$N(C_{0-10}$ alkyl)heterocycloaryl, aryl, —N-heterocycloaryl, —S-heterocycloaryl or —O-heterocycloaryl, and m is 0, 1 or 2;
preferably, when $R_1$ is selected from H, $C_{1-6}$ alkyl, $R_2$ is selected from $C_{2-6}$ alkenyl, $C_{2-6}$ alkynyl, wherein any carbon atom on alkenyl or alkynyl can be substituted by one or more selected from the group consisting of halogen and phenyl; more preferably, when $R_1$ is selected from H or $C_{1-3}$ alkyl, $R_2$ is selected from $C_{2-6}$ alkenyl, wherein any carbon atom on the alkenyl or alkynyl can be substituted by one or more selected from the group consisting of halogen and phenyl; most preferably, when $R_1$ is selected from methyl, ethyl or propyl, $R_2$ is selected from —CH=$CH_2$, —CH=$CHCH_2CH_2CH_3$,

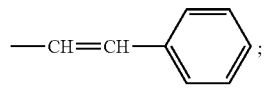

alternatively, when $R_1$ is selected from

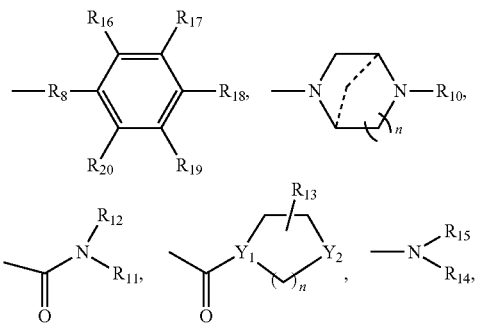

$R_2$ is selected from H, $C_{1-10}$ alkyl, $C_{2-10}$ alkenyl, $C_{2-10}$ alkynyl or $C_{3-10}$ cycloalkyl, wherein any carbon atom on alkyl, alkenyl or alkynyl can be substituted by one or more selected from the group consisting of: halogen, —CN, —$OC_{0-10}$ alkyl, —$S(O)_mC_{0-10}$ alkyl, —$SO_2N(C_{0-10}$ alkyl)($C_{0-10}$ alkyl), —$N(C_{0-10}$ alkyl)($C_{0-10}$ alkyl), —$N(C_{0-10}$ alkyl)

C(=O)(C$_{0-10}$ alkyl), —N(C$_{0-10}$ alkyl)C(=O)O(C$_{0-10}$ alkyl), —N(C$_{0-10}$ alkyl)C(=O)N(C$_{0-10}$ alkyl), —C(=O)C$_{0-10}$ alkyl, —C(=O)OC$_{0-10}$ alkyl, —C(=O)N(C$_{0-10}$ alkyl)(C$_{0-10}$ alkyl), -heterocycloalkyl, —N(C$_{0-10}$ alkyl)heterocycloalkyl, —N(C$_{0-10}$ alkyl)aryl, —N(C$_{0-10}$ alkyl)heterocycloaryl, aryl, —N-heterocycloaryl, —S-heterocycloaryl and —O-heterocycloaryl, and m is 0, 1 or 2;
preferably, when R$_1$ is selected from

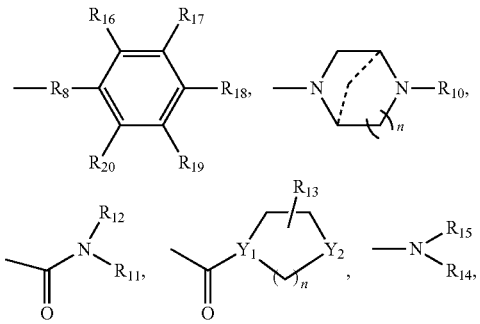

R$_2$ is selected from H, C$_{1-6}$ alkyl or C$_{2-6}$ alkenyl, wherein any carbon atom on alkyl or alkenyl or alkynyl can be substituted by one or more selected from the group consisting of: halogen, —OC$_{0-6}$ alkyl, —S(O)$_m$C$_{0-6}$ alkyl, and phenyl, and m is 0, 1 or 2;
wherein, R$_8$ is selected from a single bond, C$_{1-10}$ alkylene, C$_{1-10}$ alkylenearyl, C(=O)N(C$_{0-10}$ alkyl)(C$_{1-10}$ alkylene), —C(=O)N(C$_{0-10}$ alkyl)(aryl)-, -aryl C(=O)N(C$_{0-10}$ alkyl)-, —C$_{1-10}$ alkylene C(=O)N(C$_{0-10}$ alkyl)-, wherein any carbon atom on alkylene, alkyl or aryl can be substituted by one or more selected from the group consisting of: halogen, —CN, —OC$_{0-10}$ alkyl, —S(O)$_m$C$_{0-10}$ alkyl, —SO$_2$N(C$_{0-10}$ alkyl)(C$_{0-10}$ alkyl), —N(C$_{0-10}$ alkyl)(C$_{0-10}$ alkyl), —N(C$_{0-10}$ alkyl)C(=O)(C$_{0-10}$ alkyl), —N(C$_{0-10}$ alkyl)C(=O)O(C$_{0-10}$ alkyl), —N(C$_{0-10}$ alkyl)C(=O)N(C$_{0-10}$ alkyl), —C(=O)C$_{0-10}$ alkyl, —C(=O)OC$_{0-10}$ alkyl, —C(=O)N(C$_{0-10}$ alkyl)(C$_{0-10}$ alkyl), -heterocycloalkyl, —N(C$_{0-10}$ alkyl)heterocycloalkyl, —N(C$_{0-10}$ alkyl)aryl, —N(C$_{0-10}$ alkyl)heterocycloaryl, aryl, —C$_{1-10}$ alkylaryl, —C$_{1-10}$ alkylheterocycloaryl, —N-heterocycloaryl, —S-heterocycloaryl and —O-heterocycloaryl, and m is 0, 1 or 2;
preferably, R$_8$ is selected from a single bond, C$_{1-6}$ alkylene,

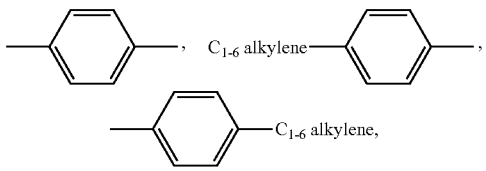

—N(C$_{0-6}$ alkyl)C(=O)—, —N(C$_{0-6}$ alkyl)C(=O)(C$_{1-6}$ alkylene),

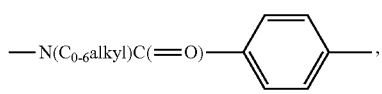

—N(C$_{0-6}$ alkyl)C(=O)—, C$_{1-6}$ alkylene N(C$_{0-6}$ alkyl)C(=O)—,

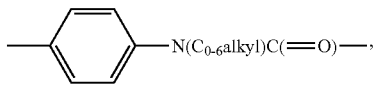

wherein any carbon atom on alkylene, alkyl or phenyl can be substituted by one or more selected from the group consisting of: halogen and —OC$_{0-6}$ alkyl;
more preferably, R$_8$ is selected from a single bond, —CH$_2$, —CH$_2$CH$_2$—,

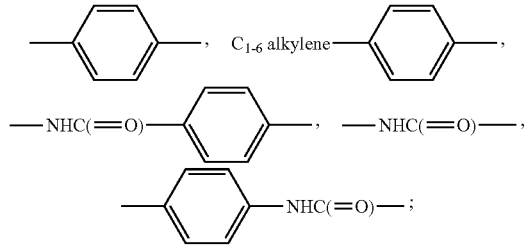

R$_{16}$, R$_{17}$, R$_{18}$, R$_{19}$ and R$_{20}$ are independently selected from H, C$_{1-10}$ alkyl, C$_{2-10}$ alkenyl, C$_{2-10}$ alkynyl, C$_{3-10}$ cycloalkyl, halogen, —CN, —OC$_{0-10}$ alkyl, —S(O)$_m$C$_{0-10}$ alkyl, —SO$_2$N(C$_{0-10}$ alkyl)(C$_{0-10}$ alkyl), —N(C$_{0-10}$ alkyl)(C$_{0-10}$ alkyl), —N(C$_{0-10}$ alkyl)C(=O)R$_{21}$, —N(C$_{0-10}$ alkyl)C(=O)O(C$_{0-10}$ alkyl), —N(C$_{0-10}$ alkyl)C(=O)N(C$_{0-10}$ alkyl), —C(=O)C$_{0-10}$ alkyl, —C(=O)OC$_{0-10}$ alkyl, —C(=O)N(C$_{0-10}$ alkyl)(C$_{0-10}$ alkyl), -heterocycloalkyl, —N(C$_{0-10}$ alkyl)heterocycloalkyl, —N(C$_{0-10}$ alkyl)heterocycloaryl, —N(C$_{0-10}$ alkyl)aryl, heterocycloalkyl, aryl, —N-heterocycloaryl, —S-heterocycloaryl, —O-heterocycloaryl, or silicyl, wherein
any carbon atom on alkyl, aryl, heterocycloalkyl, heterocycloaryl, alkenyl or alkynyl can be substituted by one or more selected from the group consisting of: halogen, —CN, —OC$_{0-10}$ alkyl, —S(O)$_m$C$_{0-10}$ alkyl, —SO$_2$N(C$_{0-10}$ alkyl)(C$_{0-10}$ alkyl), —N(C$_{0-10}$ alkyl)(C$_{0-10}$ alkyl), —N(C$_{0-10}$ alkyl)C(=O)(C$_{0-10}$ alkyl), —N(C$_{0-10}$ alkyl)C(=O)O(C$_{0-10}$ alkyl), —N(C$_{0-10}$ alkyl)C(=O)N(C$_{0-10}$ alkyl), —C(=O)C$_{0-10}$ alkyl, —C(=O)OC$_{0-10}$ alkyl, —C(=O)N(C$_{0-10}$ alkyl)(C$_{0-10}$ alkyl), -heterocycloalkyl, —N(C$_{0-10}$ alkyl)heterocycloalkyl, —N(C$_{0-10}$ alkyl)heterocycloaryl, heterocycloalkyl, aryl, —C$_{1-10}$ alkylaryl, —C$_{1-10}$ alkylheterocyclo aryl, —N-heterocycloaryl, —S-heterocyclo aryl and —O-heterocycloaryl, and m is 0, 1 or 2;
R$_{21}$ is selected from H, C$_{1-10}$ alkyl, C$_{2-10}$ alkenyl, C$_{2-10}$ alkynyl, C$_{3-10}$ cycloalkyl, halogen, —CN, —OC$_{0-10}$ alkyl, —S(O)$_m$C$_{0-10}$ alkyl, —SO$_2$N(C$_{0-10}$ alkyl)(C$_{0-10}$ alkyl), —N(C$_{0-10}$ alkyl)(C$_{0-10}$ alkyl), —N(C$_{0-10}$ alkyl)C(=O)O(C$_{0-10}$ alkyl), —N(C$_{0-10}$ alkyl)C(=O)N(C$_{0-10}$ alkyl), —C(=O)C$_{0-10}$ alkyl, —C(=O)OC$_{0-10}$ alkyl, —C(=O)N(C$_{0-10}$ alkyl)(C$_{0-10}$ alkyl), -heterocycloalkyl, —N(C$_{0-10}$ alkyl)heterocycloalkyl, —N(C$_{0-10}$ alkyl)heterocycloaryl, —N(C$_{0-10}$ alkyl)aryl, heterocycloalkyl, aryl, —N-heterocycloaryl, —S-heterocycloaryl, —O-heterocycloaryl or silicyl, wherein
any carbon atom on alkyl, aryl, heterocycloalkyl, heterocycloaryl, alkenyl or alkynyl can be substituted by one or more selected from the group consisting of: halogen, —CN, —OC$_{0-10}$ alkyl, —S(O)$_m$C$_{0-10}$ alkyl, —SO$_2$N(C$_{0-10}$ alkyl)(C$_{0-10}$ alkyl), —N(C$_{0-10}$ alkyl)(C$_{0-10}$ alkyl), —N(C$_{0-10}$ alkyl)C(=O)(C$_{0-10}$ alkyl), —N(C$_{0-10}$ alkyl)C(=O)O(C$_{0-10}$ alkyl), —N(C$_{0-10}$ alkyl)C(=O)N(C$_{0-10}$ alkyl), —C(=O)C$_{0-10}$ alkyl, —C(=O)OC$_{0-10}$ alkyl, —C(=O)N(C$_{0-10}$ alkyl)(C$_{0-10}$ alkyl), -heterocycloalkyl, —N(C$_{0-10}$ alkyl)heterocycloalkyl, —N(C$_{0-10}$ alkyl)heterocycloaryl, heterocycloalkyl, aryl, —C$_{1-10}$ alkylaryl, —C$_{1-10}$ alkylheterocyclo aryl, —N-heterocycloaryl, —S-heterocycloaryl and —O-heterocycloaryl, and m is 0, 1 or 2;

preferably, R$_{16}$, R$_{17}$, R$_{18}$, R$_{19}$ and R$_{20}$ are independently selected from H, C$_{1-6}$ alkyl, halogen, phenyl, —CN, —OH, —S(O)$_2$C$_{0-3}$ alkyl, —C(=O)C$_{0-3}$ alkyl, —N(C$_{0-3}$ alkyl)C(=O)(C$_{0-3}$ alkyl), trimethylsilyl, triethylsilyl, N-heterocyclobutyl, pyridyl, pyrazolyl, pyrrolidinyl, pyranyl, tetrahydropyranyl, thienyl, tetrahydrofuryl, pyrazinyl, imidazolyl, piperidyl, piperazinyl, indolyl, morpholinyl, homopiperazinyl, thienyl, furyl, or oxazolyl, —NHC(=O)R$_{21}$, wherein H on the N atom may optionally be substituted by C$_{1-10}$ alkyl, C$_{3-10}$ cycloalkyl, —CF$_3$, or t-butyloxycarboryl;

more preferably, R$_{21}$ is selected from linear or branched C$_{1-6}$ alkyl, C$_{3-10}$ cycloalkyl, halogen, —OC$_{0-6}$ alkyl, phenyl, N-heterocyclobutyl, pyridyl, pyrazolyl, pyrrolidinyl, pyranyl, tetrahydropyranyl, thienyl, tetrahydrofuryl, pyrazinyl, imidazolyl, piperidyl, piperazinyl, indolyl, morpholinyl, homopiperazinyl, thienyl, furyl, oxazolyl, wherein H on the N atom may optionally be substituted by C$_{1-10}$ alkyl, C$_{3-10}$ cycloalkyl, —CF$_3$, or t-butyloxycarboryl;

most preferably, R$_{21}$ is selected from halophenyl, benzyl,

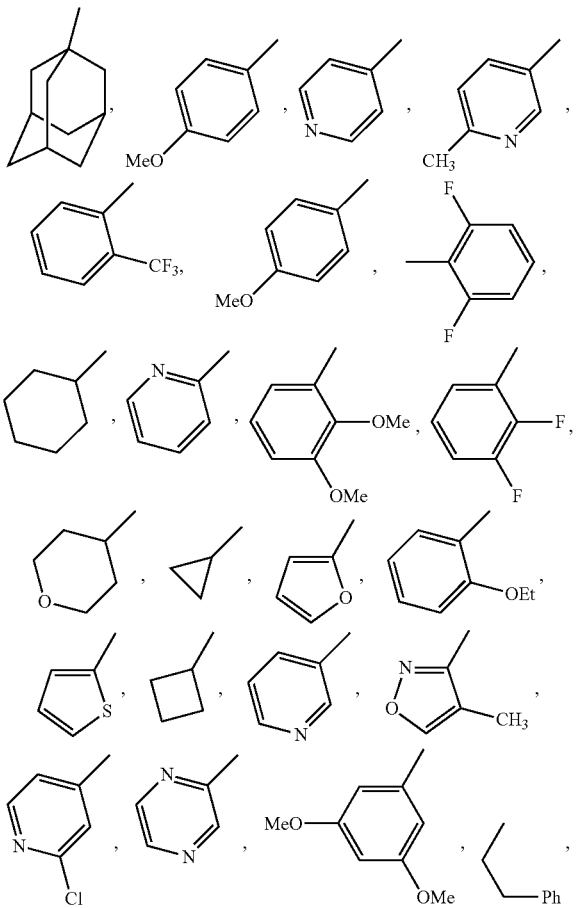

isobutyl, or propyl, it is particularly preferred that, R$_{16}$, R$_{17}$, R$_{18}$, R$_{19}$ and R$_{20}$ are independently selected from H, methyl, ethyl, propyl, isopropyl, halogen, —OH,

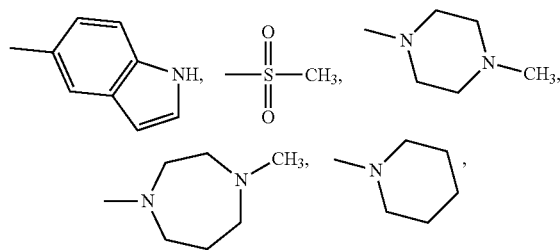

R$_{10}$ is selected from H, C$_{1-10}$ alkyl, C$_{2-10}$ alkenyl, C$_{2-10}$ alkynyl, C$_{3-10}$ cycloalkyl, heterocycloalkyl, aryl, —N-heterocycloaryl, —S-heterocycloaryl or —O-heterocycloaryl, wherein any carbon atom on alkyl, aryl, heterocycloalkyl, heterocycloaryl, alkenyl or alkynyl can be substituted by one or more selected from the group consisting of: halogen, —CN, —OC$_{0-10}$ alkyl, —S(O)$_m$C$_{0-10}$ alkyl, —SO$_2$N(C$_{0-10}$ alkyl)(C$_{0-10}$ alkyl), —N(C$_{0-10}$ alkyl)(C$_{0-10}$ alkyl), —N(C$_{0-10}$ alkyl)C(=O)(C$_{0-10}$ alkyl), —N(C$_{0-10}$ alkyl)C(=O)O(C$_{0-10}$ alkyl), —N(C$_{0-10}$ alkyl)C(=O)N(C$_{0-10}$ alkyl), —C(=O)C$_{0-10}$ alkyl, —C(=O)OC$_{0-10}$ alkyl, —C(=O)N(C$_{0-10}$ alkyl)(C$_{0-10}$ alkyl), -heterocycloalkyl, —N(C$_{0-10}$ alkyl)heterocycloalkyl, —N(C$_{0-10}$ alkyl)heterocycloaryl, heterocycloalkyl, aryl, —C$_{1-10}$ alkylaryl, —C$_{1-10}$ alkylheterocycloaryl, —N-heterocycloaryl, —S-heterocycloaryl and —O-heterocycloaryl, and m is 0, 1 or 2;

preferably, R$_{10}$ is selected from H, linear or branched C$_{1-6}$ alkyl, phenyl, pyridyl;

R$_{11}$ and R$_{12}$ are independently selected from H, C$_{1-10}$ alkyl, C$_{2-10}$ alkenyl, C$_{2-10}$ alkynyl, C$_{3-10}$ cycloalkyl, heterocycloalkyl, —N(C$_{0-10}$ alkyl)heterocycloalkyl, —N(C$_{0-10}$ alkyl)heterocycloaryl, heterocycloalkyl, aryl, —N-heterocycloaryl, —S-heterocycloaryl or —O-heterocycloaryl, wherein any carbon atom on alkyl, aryl, heterocycloalkyl, heterocycloaryl, alkenyl or alkynyl can be substituted by one or more selected from the group consisting of: halogen, —CN, —OC$_{0-10}$ alkyl, —S(O)$_m$C$_{0-10}$ alkyl, —SO$_2$N(C$_{0-10}$ alkyl)(C$_{0-10}$ alkyl), —N(C$_{0-10}$ alkyl)(C$_{0-10}$ alkyl), —N(C$_{0-10}$ alkyl)C(=O)(C$_{0-10}$ alkyl), —N(C$_{0-10}$ alkyl)C(=O)O(C$_{0-10}$ alkyl), —N(C$_{0-10}$ alkyl)C(=O)N(C$_{0-10}$ alkyl), —C(=O)C$_{0-10}$ alkyl, —C(=O)heterocycloalkyl, —C(=O)OC$_{0-10}$ alkyl, —C(=O)N(C$_{0-10}$ alkyl)(C$_{0-10}$ alkyl), -heterocycloalkyl, —N(C$_{0-10}$ alkyl)heterocycloalkyl, —N(C$_{0-10}$ alkyl)heterocycloaryl, heterocycloalkyl, aryl, —C$_{1-10}$ alkylaryl, —C$_{1-10}$ alkylheterocycloaryl, —N-hetero cyclo aryl, —S-heterocycloaryl and —O-heterocycloaryl, and m is 0, 1 or 2;

preferably, R$_{11}$ and R$_{12}$ are independently selected from H, C$_{1-6}$ alkyl, C$_{3-10}$ cycloalkyl, phenyl, N-heterocyclobutyl, pyridyl, pyrazolyl, pyrrolidinyl, pyranyl, tetrahydropyranyl, thienyl, tetrahydrofuryl, pyrazinyl, imidazolyl, piperidyl, piperazinyl, indolyl, morpholinyl, homopiperazinyl, thienyl, furyl, or oxazolyl, wherein H on the N atom may optionally be substituted by C$_{1-6}$ alkyl, C$_{3-10}$ cycloalkyl, —CF$_3$, or t-butyloxycarboryl, and preferably, any carbon atom on the alkyl can be substituted by one or more selected from the group consisting of: halogen, —OC$_{0-6}$ alkyl, —S(O)$_m$C$_{0-6}$ alkyl, phenyl, halophenyl, benzyl, p-hydroxyphenyl, indolyl, —C(=O)OC$_{0-6}$ alkyl, p-formamidophenyl, —C(=O)tetrahydropyrrole, and —C(=O)morpholinyl, and m is 0, 1 or 2;

more preferably, R$_{11}$ and R$_{12}$ are independently selected from methyl, ethyl,

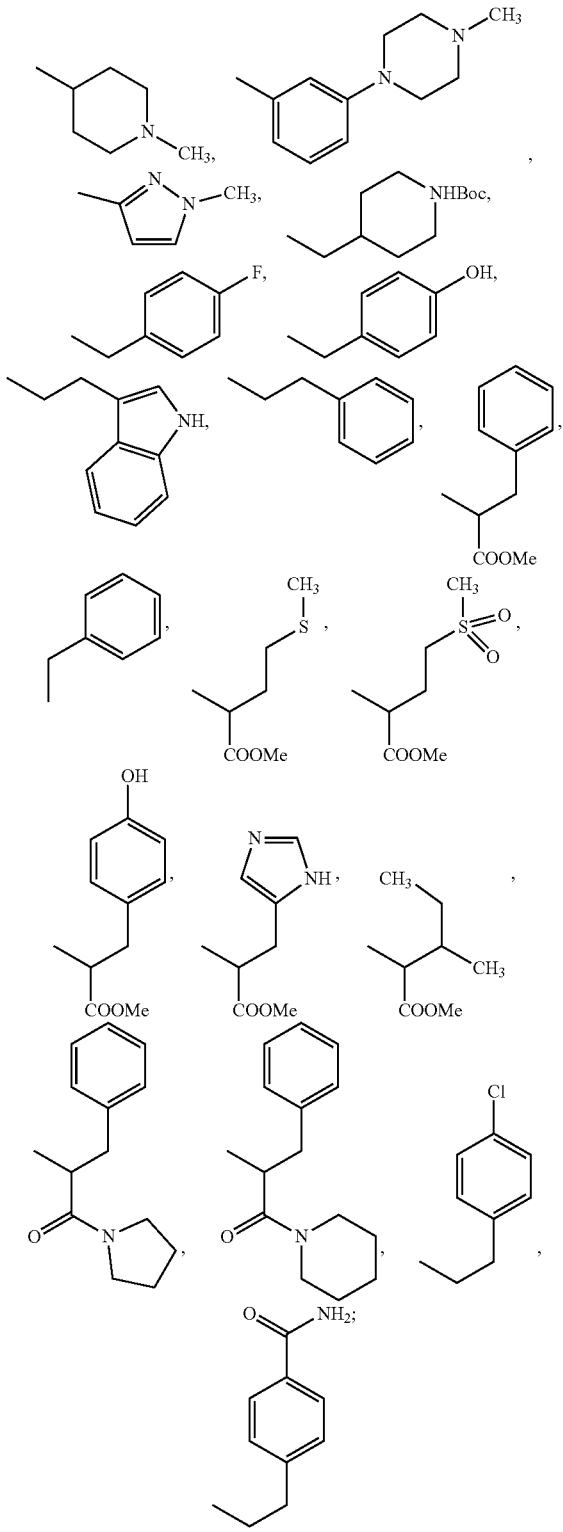

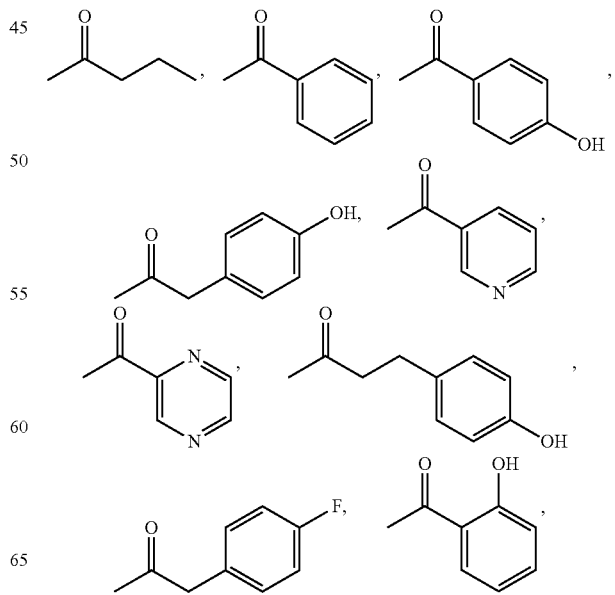

$R_{13}$ is selected from H, $C_{1-10}$ alkyl, $C_{2-10}$ alkenyl, $C_{2-10}$ alkynyl, $C_{3-10}$ cycloalkyl, heterocycloalkyl, aryl, —N-heterocycloaryl, —S-heterocycloaryl or —O-heterocycloaryl, wherein any carbon atom on the alkyl, aryl, heterocycloalkyl, heterocycloaryl, alkenyl or alkynyl can be substituted by one or more selected from the group consisting of: halogen, —CN, —OC$_{0-10}$ alkyl, —S(O)$_m$C$_{0-10}$ alkyl, —SO$_2$N(C$_{0-10}$ alkyl)(C$_{0-10}$ alkyl), —N(C$_{0-10}$ alkyl)(C$_{0-10}$ alkyl), —N(C$_{0-10}$ alkyl)C(=O)(C$_{0-10}$ alkyl), —N(C$_{0-10}$ alkyl)C(=O)O(C$_{0-10}$ alkyl), —N(C$_{0-10}$ alkyl)C(=O)N(C$_{0-10}$ alkyl), —C(=O)C$_{0-10}$ alkyl, —C(=O)OC$_{0-10}$ alkyl, —C(=O)N(C$_{0-10}$ alkyl)(C$_{0-10}$ alkyl), -heterocycloalkyl, —N(C$_{0-10}$ alkyl)heterocycloalkyl, —N(C$_{0-10}$ alkyl)heterocycloaryl, heterocycloalkyl, aryl, —C$_{1-10}$ alkylaryl, —C$_{1-10}$ alkylheterocycloaryl, —N-heterocycloaryl, —S-heterocycloaryl and —O-heterocycloaryl, and m is 0, 1 or 2;

preferably, $R_{13}$ is selected from H, $C_{1-6}$ alkyl, pyridyl, phenyl, t-butyloxycarboryl, —C(=O)OC$_{0-6}$ or alkyl;

$Y_1$ and $Y_2$ are selected from N or C;

n is selected from 1, 2 or 3;

$R_{14}$ and $R_{15}$ are independently selected from H, linear or branched $C_{1-10}$ alkyl, linear or branched $C_{2-10}$ alkenyl, linear or branched $C_{2-10}$ alkynyl, $C_{3-10}$ cycloalkyl, heterocycloalkyl, —C(=O)C$_{0-10}$ alkyl, —C(=O)heterocycloaryl, —C(=O)aryl, heterocycloaryl, heterocycloalkyl, aryl, —N-heterocycloaryl, —S-heterocycloaryl or —O-heterocycloaryl, wherein any carbon atom on the alkyl, aryl, heterocycloalkyl, heterocycloaryl, alkenyl or alkynyl can be substituted by one or more selected from the group consisting of: halogen, —CN, —OC$_{0-10}$ alkyl, —S(O)$_m$C$_{0-10}$ alkyl, —SO$_2$N(C$_{0-10}$ alkyl)(C$_{0-10}$ alkyl), —N(C$_{0-10}$ alkyl)(C$_{0-10}$ alkyl), —N(C$_{0-10}$ alkyl)C(=O)(C$_{0-10}$ alkyl), —N(C$_{0-10}$ alkyl)C(=O)O(C$_{0-10}$ alkyl), —N(C$_{0-10}$ alkyl)C(=O)N(C$_{0-10}$ alkyl), —C(=O)C$_{0-10}$ alkyl, —C(=O)heterocycloalkyl, —C(=O)OC$_{0-10}$ alkyl, —C(=O)N(C$_{0-10}$ alkyl)(C$_{0-10}$ alkyl), -heterocycloalkyl, —N(C$_{0-10}$ alkyl)heterocycloalkyl, —N(C$_{0-10}$ alkyl)heterocycloaryl, heterocycloalkyl, aryl, —C$_{1-10}$ alkylaryl, —C$_{1-10}$ alkylheterocycloaryl, —N-heterocycloaryl, —S-heterocycloaryl or —O-heterocycloaryl, and m is 0, 1 or 2;

preferably, $R_{14}$ and $R_{15}$ are independently selected from H, $C_{1-6}$ alkyl, —C(=O)C$_{0-6}$ alkyl, —C(=O)C$_{0-6}$ alkylenephenyl, —C(=O)pyridyl, —C(=O)pyrazinyl, —C(=O)imidazolyl, —C(=O)pyrazolyl, —C(=O)phenyl, wherein any carbon atom on the alkyl, phenyl, or heterocycloaryl can be substituted by one or more selected from the group consisting of: halogen, —OC$_{0-6}$ alkyl, and CF$_3$;

preferably, $R_{14}$ and $R_{15}$ are independently selected from

-continued

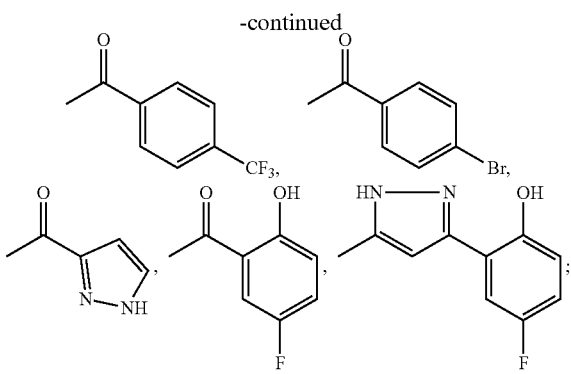

R$_3$, R$_4$, R$_5$ and R$_6$ are independently selected from H, C$_{1-10}$ alkyl, C$_{2-10}$ alkenyl, C$_{2-10}$ alkynyl, C$_{3-10}$ cycloalkyl, halogen, —CN, —OC$_{0-10}$ alkyl, —S(O)$_m$C$_{0-10}$ alkyl, —SO$_2$N(C$_{0-10}$ alkyl)(C$_{0-10}$ alkyl), —N(C$_{0-10}$ alkyl)(C$_{0-10}$ alkyl), —N(C$_{0-10}$ alkyl)C(═O)R$_{21}$, —N(C$_{0-10}$ alkyl)C(═O)O(C$_{0-10}$ alkyl), —N(C$_{0-10}$ alkyl)C(═O)N(C$_{0-10}$ alkyl), —C(═O)C$_{0-10}$ alkyl, —C(═O)OC$_{0-10}$ alkyl, —C(═O)N(C$_{0-10}$ alkyl)(C$_{0-10}$ alkyl), -heterocycloalkyl, —N(C$_{0-10}$ alkyl)heterocycloalkyl, —N(C$_{0-10}$ alkyl)heterocycloaryl, —N(C$_{0-10}$ alkyl)aryl, heterocycloalkyl, aryl, —N-heterocycloaryl, —S-heterocycloaryl, —O-heterocycloaryl, or silicyl, wherein any carbon atom on the alkyl, aryl, heterocycloalkyl, heterocycloaryl, alkenyl or alkynyl can be substituted by one or more selected from the group consisting of: halogen, —CN, —OC$_{0-10}$ alkyl, —S(O)$_m$C$_{0-10}$ alkyl, —SO$_2$N(C$_{0-10}$ alkyl)(C$_{0-10}$ alkyl), —N(C$_{0-10}$ alkyl)(C$_{0-10}$ alkyl), —N(C$_{0-10}$ alkyl)C(═O)(C$_{0-10}$ alkyl), —N(C$_{0-10}$ alkyl)C(═O)O(C$_{0-10}$ alkyl), —N(C$_{0-10}$ alkyl)C(═O)N(C$_{0-10}$ alkyl), —C(═O)C$_{0-10}$ alkyl, —C(═O)OC$_{0-10}$ alkyl, —C(═O)N(C$_{0-10}$ alkyl)(C$_{0-10}$ alkyl), -heterocycloalkyl, —N(C$_{0-10}$ alkyl)heterocycloalkyl, —N(C$_{0-10}$ alkyl)heterocycloaryl, heterocycloalkyl, aryl, —C$_{1-10}$ alkylaryl, —C$_{1-10}$ alkylheterocycloaryl, —N-hetero cyclo aryl, —S-heterocyclo aryl or —O-heterocycloaryl, and m is 0, 1 or 2;

Preferably, R$_3$, R$_4$, R$_5$ and R$_6$ are independently selected from H, C$_{1-6}$ alkyl, C$_{3-10}$ cycloalkyl, halogen, —OC$_{0-6}$ alkyl, —N(C$_{0-6}$ alkyl)(C$_{0-6}$ alkyl), —N(C$_{0-6}$ alkyl)C(═O)(C$_{0-6}$ alkyl), —N(C$_{0-6}$ alkyl)C(═O)O(C$_{0-6}$ alkyl), —N(C$_{0-6}$ alkyl)C(═O)N(C$_{0-6}$ alkyl), —C(═O)C$_{0-6}$ alkyl, —C(═O)OC$_{0-6}$ alkyl, —C(═O)N(C$_{0-6}$ alkyl)(C$_{0-6}$ alkyl), or phenyl, more preferably, R$_3$ is selected from —NH$_2$;

more preferably, R$_4$ is selected from halogen;

more preferably, R$_5$ and R$_6$ are independently selected from H, C$_{1-6}$ alkyl;

R$_7$ is selected from H, C$_{1-10}$ alkyl, C$_{3-10}$ cycloalkyl, —OC$_{0-10}$ alkyl, and C(═O)C$_{0-10}$ alkyl, wherein any carbon atom on the alkyl can be substituted by one or more selected from the group consisting of: halogen, —CN, —OC$_{0-10}$ alkyl, —S(O)$_m$C$_{0-10}$ alkyl, —SO$_2$N(C$_{0-10}$ alkyl)(C$_{0-10}$ alkyl), —N(C$_{0-10}$ alkyl)(C$_{0-10}$ alkyl), —N(C$_{0-10}$ alkyl)C(═O)(C$_{0-10}$ alkyl), —N(C$_{0-10}$ alkyl)C(═O)O(C$_{0-10}$ alkyl), —N(C$_{0-10}$ alkyl)C(═O)N(C$_{0-10}$ alkyl), —C(═O)C$_{0-10}$ alkyl, —C(═O)OC$_{0-10}$ alkyl, —C(═O)N(C$_{0-10}$ alkyl)(C$_{0-10}$ alkyl), -heterocycloalkyl, —N(C$_{0-10}$ alkyl)heterocycloalkyl, —N(C$_{0-10}$ alkyl)heterocycloaryl, heterocycloalkyl, aryl, —C$_{1-10}$ alkylaryl, —C$_{1-10}$ alkylheterocycloaryl, —N-heterocycloaryl, —S-heterocycloaryl and —O-heterocycloaryl, and m is 0, 1 or 2, preferably, R$_7$ is selected from H, or C$_{1-6}$ alkyl, and more preferably, R$_7$ is selected from H.

A specific embodiment of the present invention provides a compound represented by Formula (II), and a pharmaceutically acceptable salt, stereoisomer, ether, ester, prodrug and solvate thereof, Formula (II)

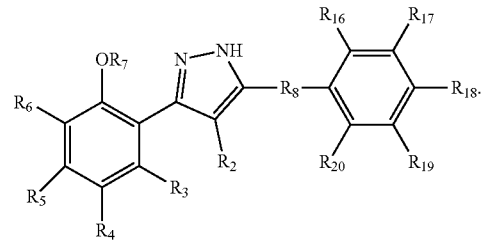

Preferably, a specific embodiment of the present invention provides a compound represented by Formula (II-1), and a pharmaceutically acceptable salt, stereoisomer, ether, ester, prodrug and solvate thereof, Formula (II-1)

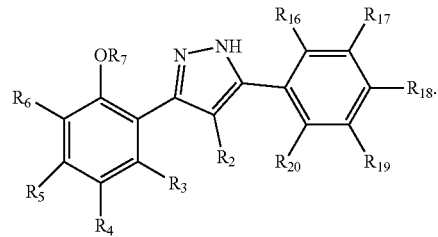

Preferably, a specific embodiment of the present invention provides a compound represented by Formula (II-2), and a pharmaceutically acceptable salt, stereoisomer, ether, ester, prodrug and solvate thereof, Formula (II-2)

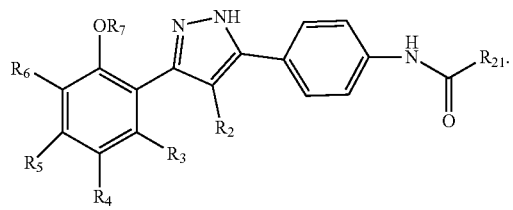

A specific embodiment of the present invention provides a compound represented by Formula (III), and a pharmaceutically acceptable salt, stereoisomer, ether, ester, prodrug and solvate thereof,

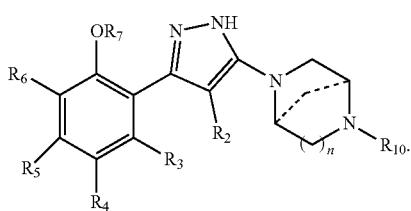

Formula (III)

Preferably, a specific embodiment of the present invention provides a compound represented by Formula (III-1), and a pharmaceutically acceptable salt, stereoisomer, ether, ester, prodrug and solvate thereof,

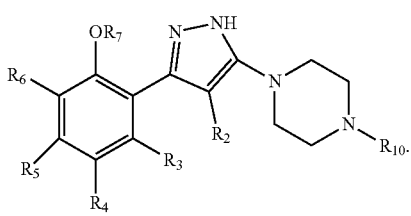

Formula (III-1)

Preferably, a specific embodiment of the present invention provides a compound represented by formula (III-2), and a pharmaceutically acceptable salt, stereoisomer, ether, ester, prodrug and solvate thereof,

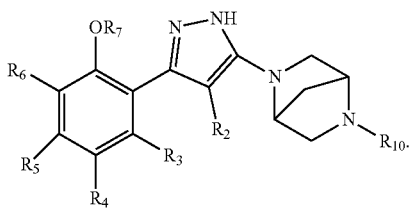

Formula (III-2)

Preferably, a specific embodiment of the present invention provides a compound represented by Formula (III-3), and a pharmaceutically acceptable salt, stereoisomer, ether, ester, prodrug and solvate thereof,

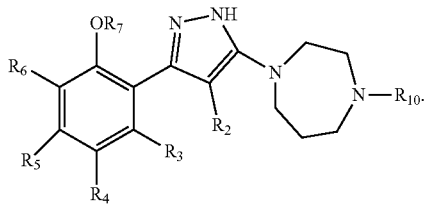

Formula (III-3)

A specific embodiment of the present invention provides a compound represented by Formula (IV), and a pharmaceutically acceptable salt, stereoisomer, ester, prodrug and solvate thereof,

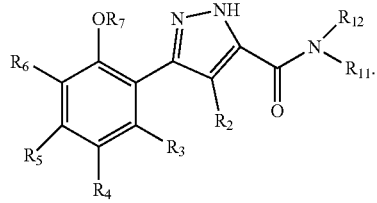

Formula (IV)

Preferably, a specific embodiment of the present invention provides a compound represented by Formula (IV-1), and a pharmaceutically acceptable salt, stereoisomer, ether, ester, prodrug and solvate thereof,

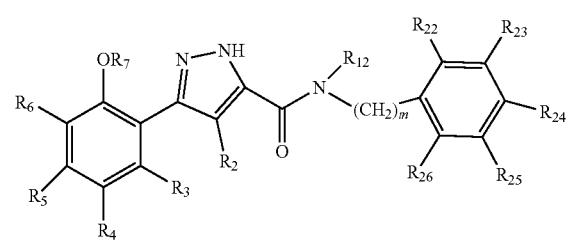

Formula (IV-1)

wherein, $R_{22}$, $R_{23}$, $R_{24}$, $R_{25}$ and $R_{26}$ are independently selected from halogen, $-NH_2$, $-OH$, $C_{1-10}$ alkyl, or $-CF_3$, and m is 0, 1, or 2.

A specific embodiment of the present invention provides a compound represented by Formula (V), and a pharmaceutically acceptable salt, stereoisomer, ether, ester, prodrug and solvate thereof,

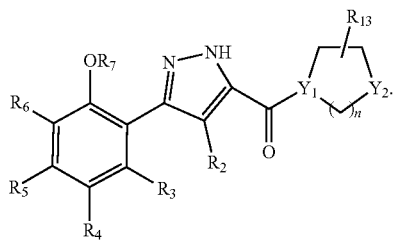

Formula (V)

Preferably, a specific embodiment of the present invention provides a compound represented by Formula (V-1), and a pharmaceutically acceptable salt, stereoisomer, ether, ester, prodrug and solvate thereof,

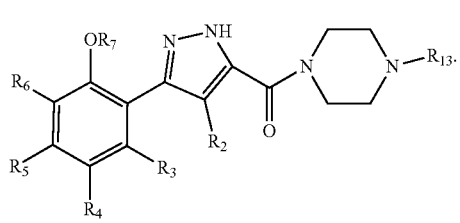

Formula (V-1)

Preferably, a specific embodiment of the present invention provides a compound represented by Formula (V-2), and a pharmaceutically acceptable salt, stereoisomer, ether, ester, prodrug and solvate thereof, Formula (V-2)

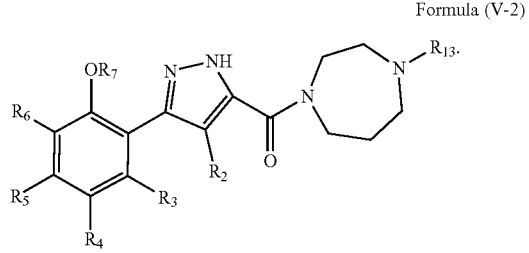

Preferably, a specific embodiment of the present invention provides a compound represented by Formula (V-3), and a pharmaceutically acceptable salt, stereoisomer, ether, ester, prodrug and solvate thereof, Formula (V-3)

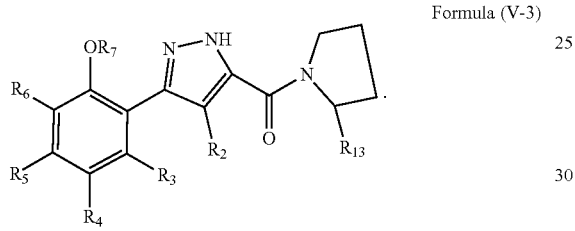

A specific embodiment of the present invention provides a compound represented by Formula (VI), and a pharmaceutically acceptable salt, stereoisomer, ether, ester, prodrug and solvate thereof, Formula (VI)

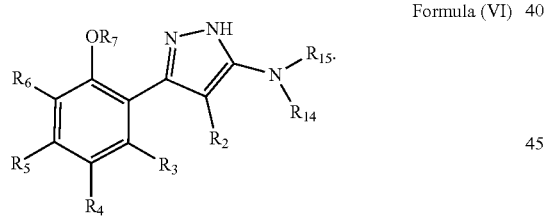

Preferably, a specific embodiment of the present invention provides a compound represented by formula (VI-1), and a pharmaceutically acceptable salt, stereoisomer, ether, ester, prodrug and solvate thereof, Formula (VI-1)

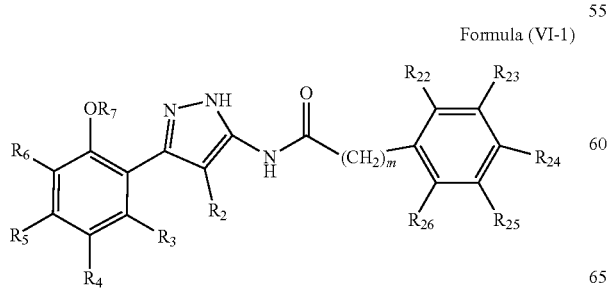

wherein, $R_{22}$, $R_{23}$, $R_{24}$, $R_{25}$ and $R_{26}$ are independently selected from halogen, —$NH_2$, —OH, $C_{1-10}$ alkyl, —$CF_3$, and m is 0, 1, or 2.

A more specific embodiment of the present invention provides specific compounds as follows:

BRM2-1

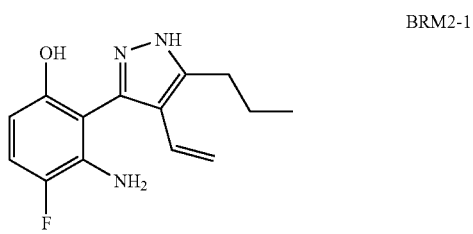

BRM2-2

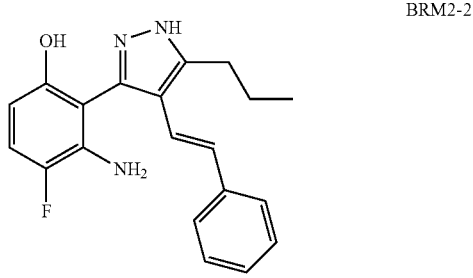

BRM2-3

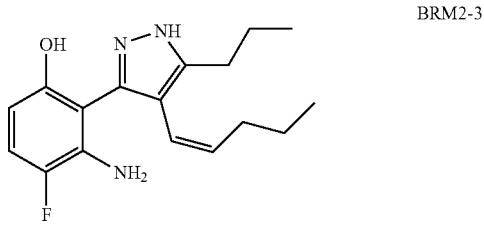

BRM2-4

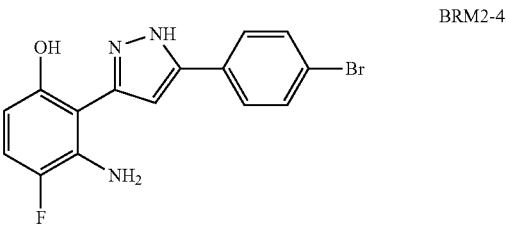

BRM2-5

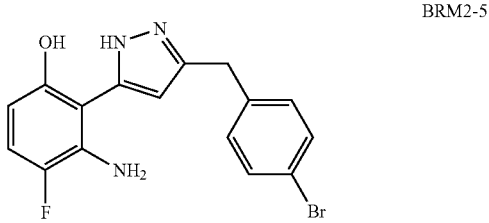

BRM2-6

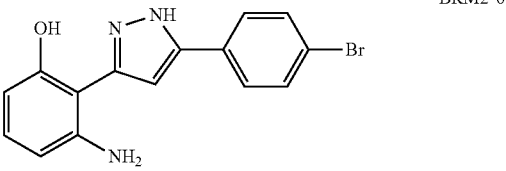

-continued
BRM2-7
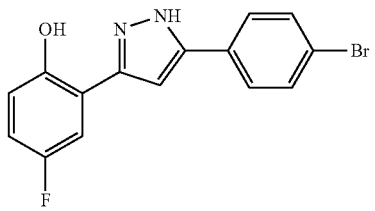 [SMILES: Nc1c(F)ccc(O)c1-c1cc(-c2ccc(Br)cc2)[nH]n1]
BRM2-8
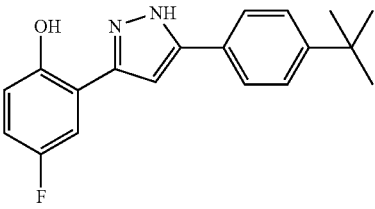 [SMILES: CC(C)(C)c1ccc(-c2cc(-c3cc(F)ccc3O)n[nH]2)cc1]
BRM2-9
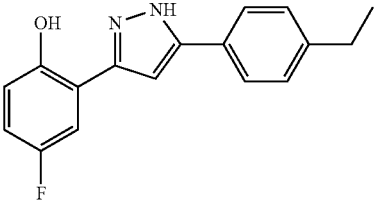 [SMILES: CCc1ccc(-c2cc(-c3cc(F)ccc3O)n[nH]2)cc1]
BRM2-10
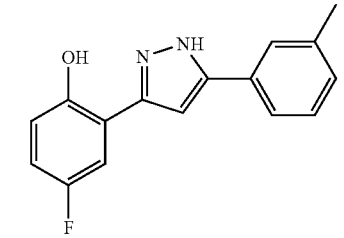
BRM2-11
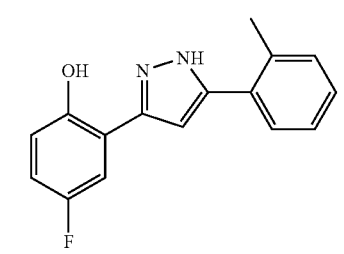 [SMILES: Cc1ccccc1-c1cc(-c2cc(F)ccc2O)n[nH]1]
BRM2-12
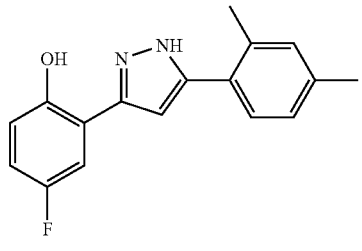
BRM2-13
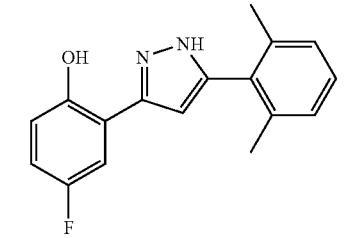
-continued
BRM2-14
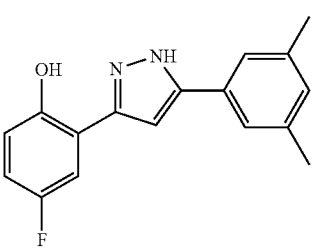
BRM2-15
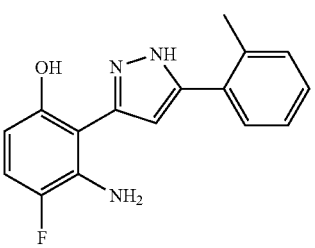
BRM2-16
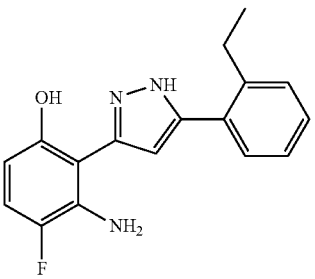
BRM2-17
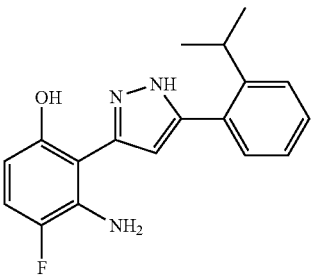
BRM2-18
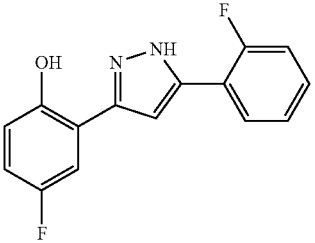
BRM2-19
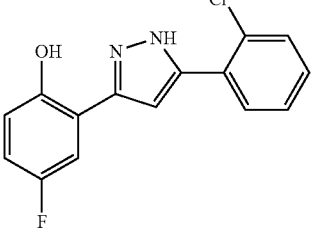

BRM2-20
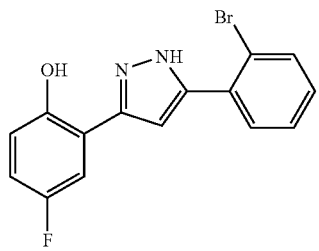
BRM2-21
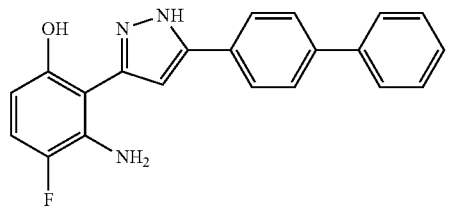
BRM2-22
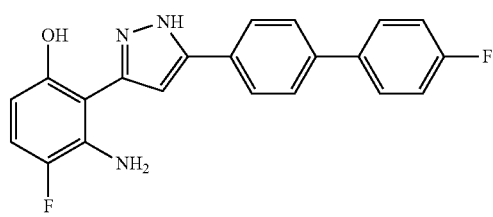 [SMILES: Nc1c(F)ccc(O)c1-c1cc(-c2ccc(-c3ccc(F)cc3)cc2)[nH]n1]
BRM2-23
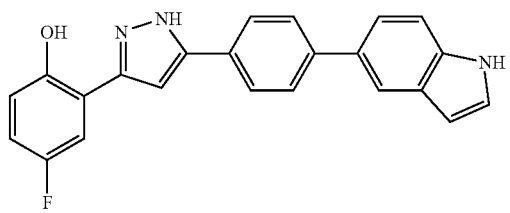
BMR2-24
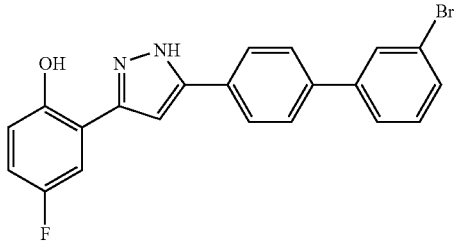
BRM2-25
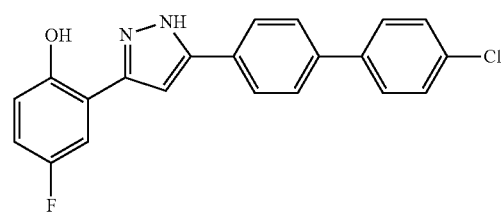
BRM2-26
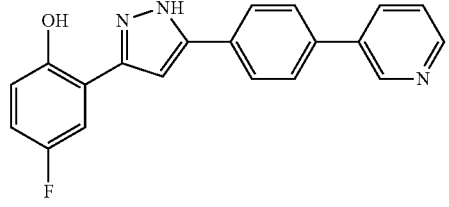
BRM2-27
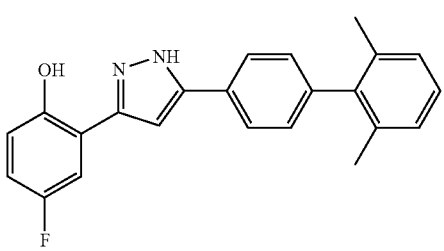 [SMILES: Cc1cccc(C)c1-c1ccc(-c2cc(-c3cc(F)ccc3O)n[nH]2)cc1]
BRM2-28
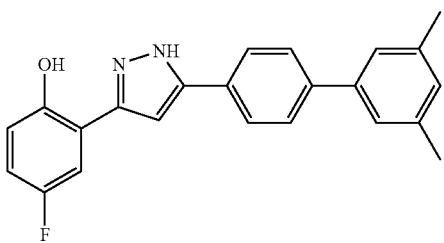
BRM2-29
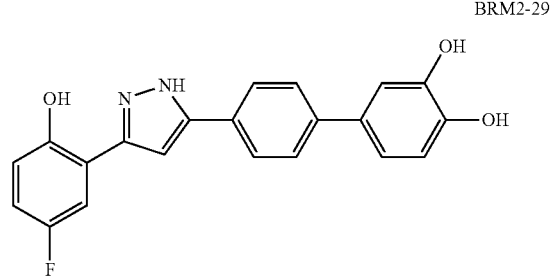
BRM2-30
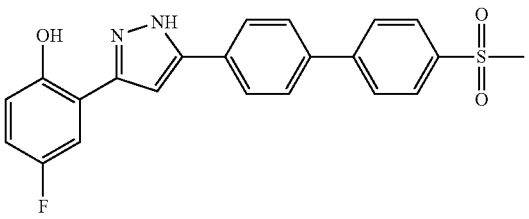 [SMILES: CS(=O)(=O)c1ccc(-c2ccc(-c3cc(-c4cc(F)ccc4O)n[nH]3)cc2)cc1]
BRM2-31
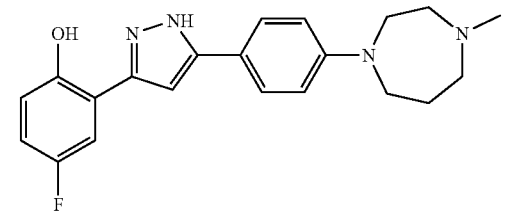 [SMILES: CN1CCCN(c2ccc(-c3cc(-c4cc(F)ccc4O)n[nH]3)cc2)CC1]
BRM2-32
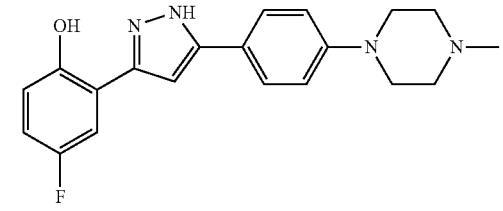 [SMILES: CN1CCN(c2ccc(-c3cc(-c4cc(F)ccc4O)n[nH]3)cc2)CC1]

BRM2-33 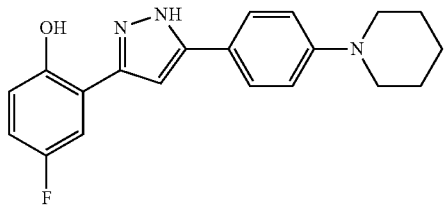 [SMILES: Oc1ccc(F)cc1-c1cc(-c2ccc(N3CCCCC3)cc2)[nH]n1]
BRM2-34 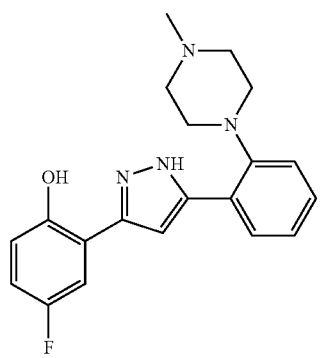 [SMILES: CN1CCN(c2ccccc2-c2cc(-c3cc(F)ccc3O)n[nH]2)CC1]
BRM2-35 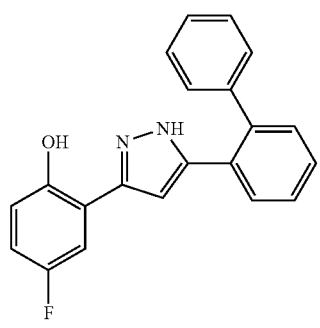
BRM2-36 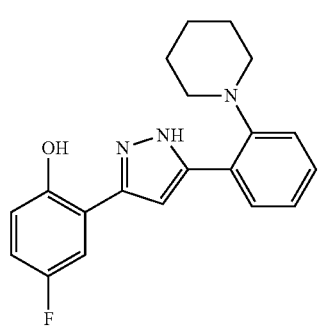
BRM2-37 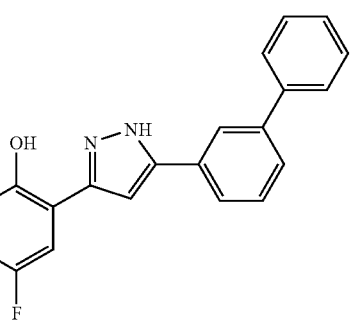
BRM2-38 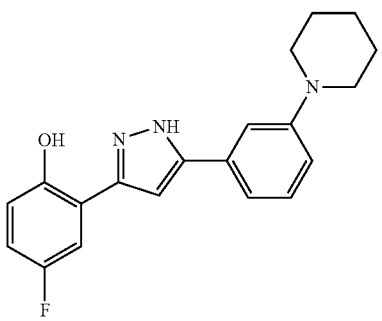
BRM2-39 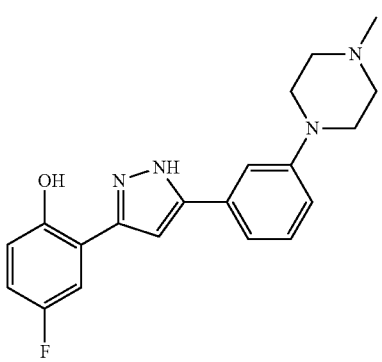 [SMILES: CN1CCN(c2cccc(-c3cc(-c4cc(F)ccc4O)n[nH]3)c2)CC1]
BRM2-40 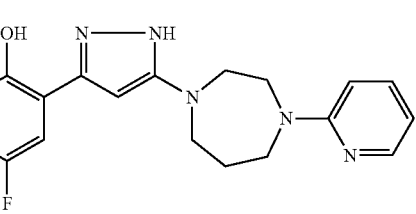
BRM2-41 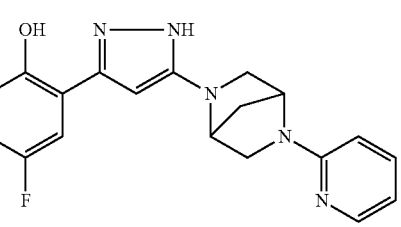
BRM2-42 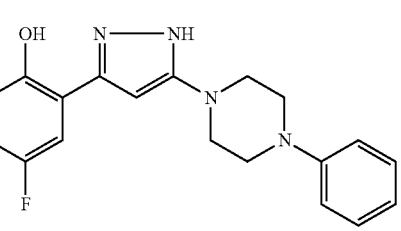
BRM2-96 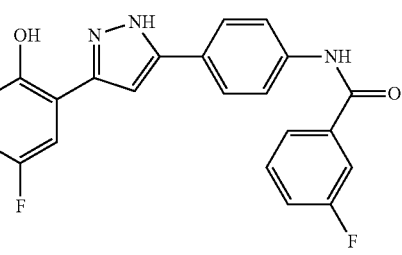

-continued
BRM2-97
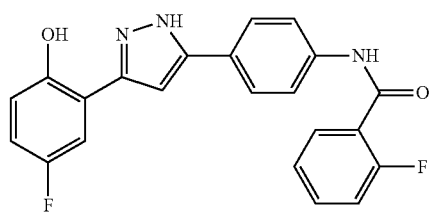
BRM2-98
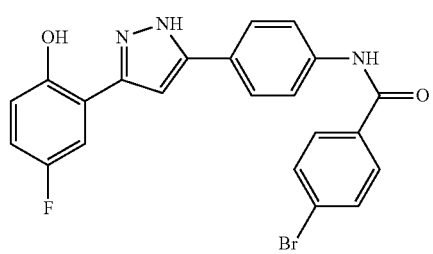
BRM2-99
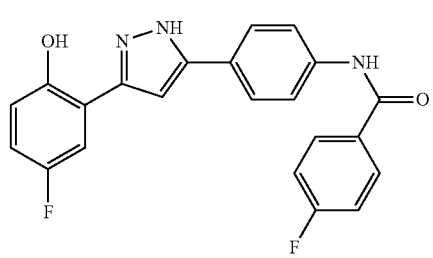
BRM2-100
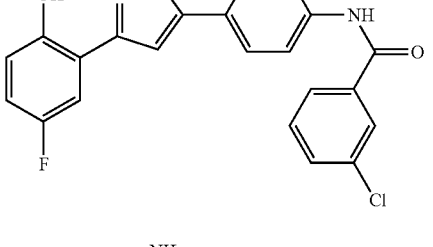
BRM2-101
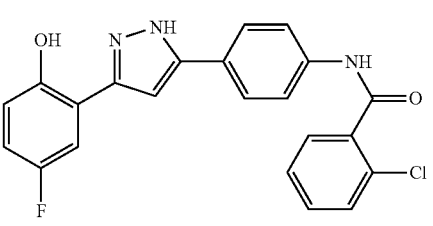
BRM2-102
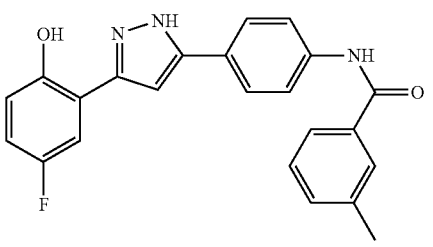
-continued
BRM2-103
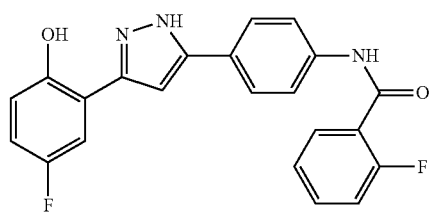
BRM2-104
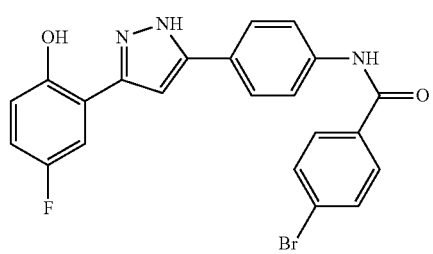
BRM2-105
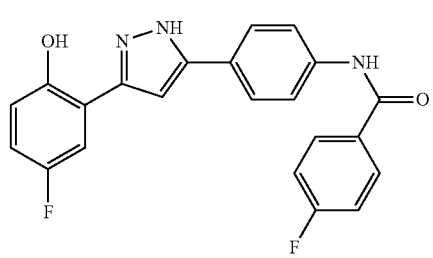
BRM2-106
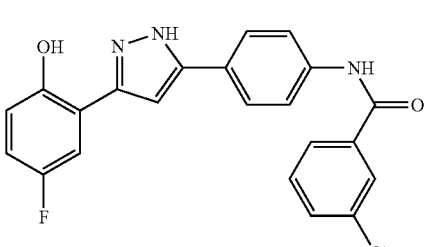
BRM2-107
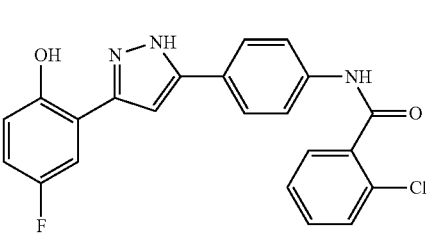
BRM2-108
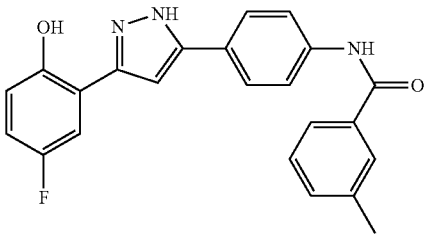

BRM2-109
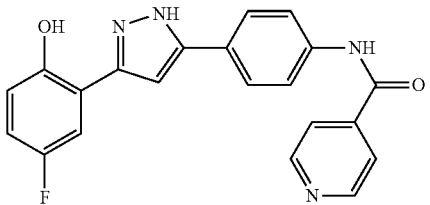
BRM2-110
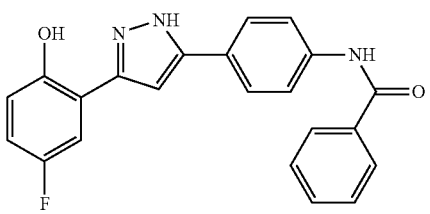
BRM2-111
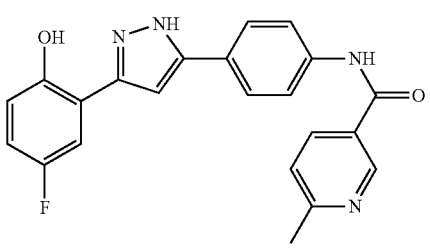 [SMILES: Cc1ccc(C(=O)Nc2ccc(-c3cc(-c4cc(F)ccc4O)n[nH]3)cc2)cn1]
BRM2-112
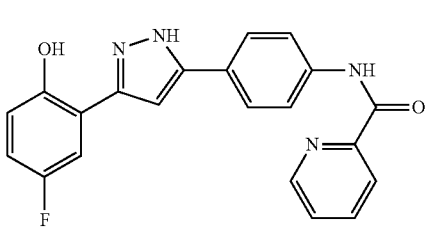 [SMILES: O=C(Nc1ccc(-c2cc(-c3cc(F)ccc3O)n[nH]2)cc1)c1ccccn1]
BRM2-113
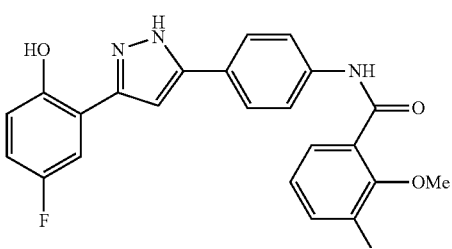
BRM2-114
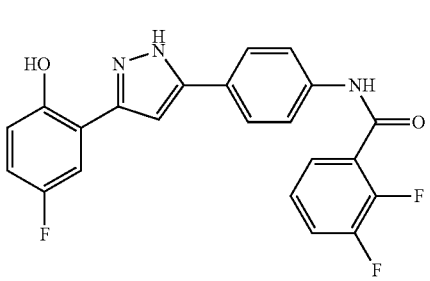
BRM2-115
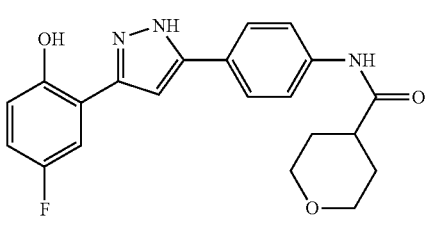
BRM2-116
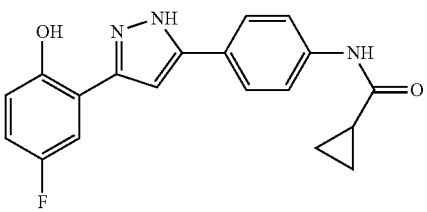
BRM2-117
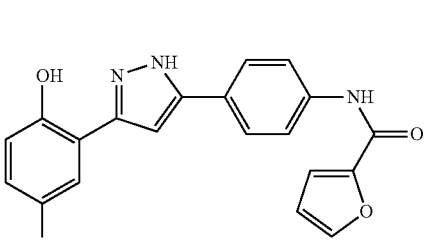
BRM2-118
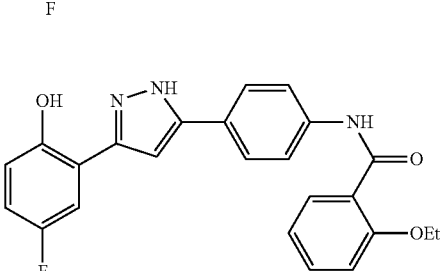
BRM2-119
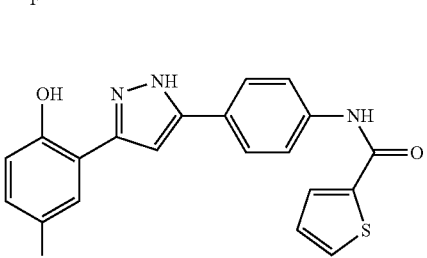
BRM2-120
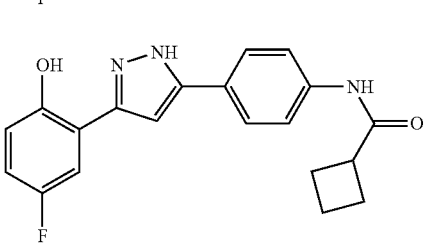
BRM2-121
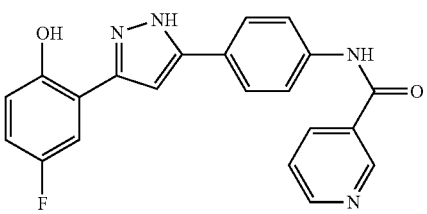 [SMILES: O=C(Nc1ccc(-c2cc(-c3cc(F)ccc3O)n[nH]2)cc1)c1cccnc1]
BRM2-122
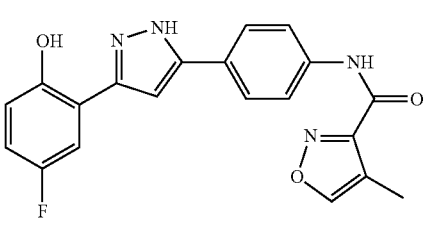

BRM2-123
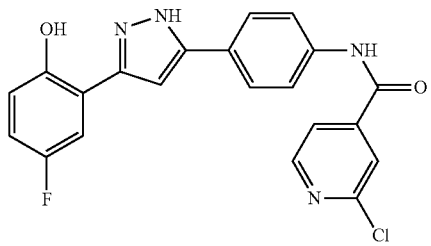 [SMILES: O=C(Nc1ccc(-c2cc(-c3cc(F)ccc3O)n[nH]2)cc1)c1ccnc(Cl)c1]
BRM2-124
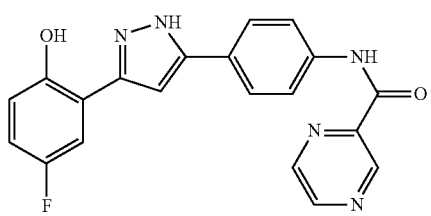 [SMILES: O=C(Nc1ccc(-c2cc(-c3cc(F)ccc3O)n[nH]2)cc1)c1cnccn1]
BRM2-125
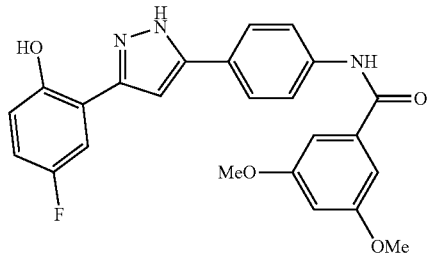
BRM2-126
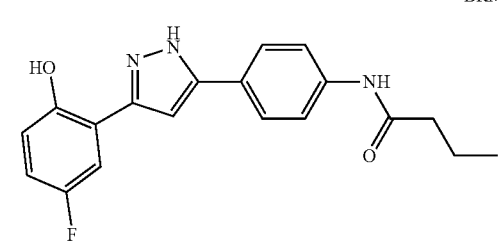
BRM2-127
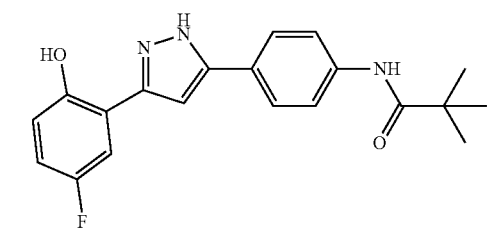
BRM2-128
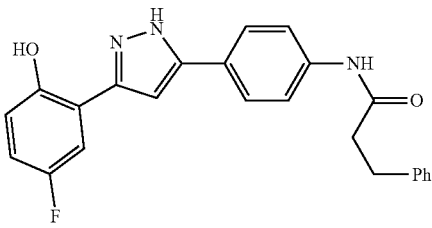
BRM2-129
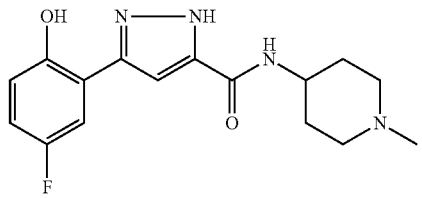
BRM2-130
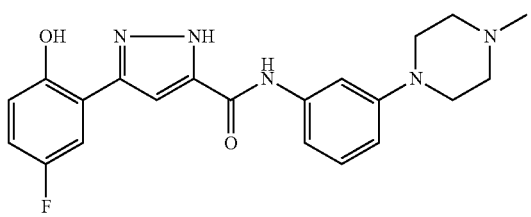
BRM2-131
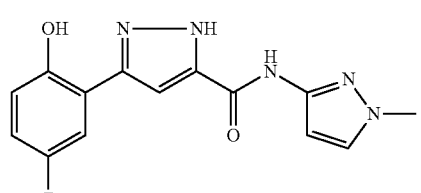
BRM2-132
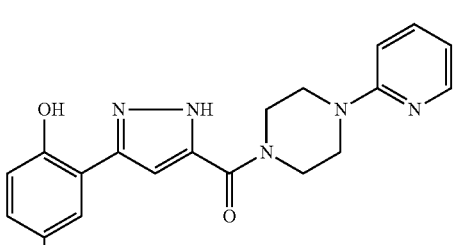
BRM2-133
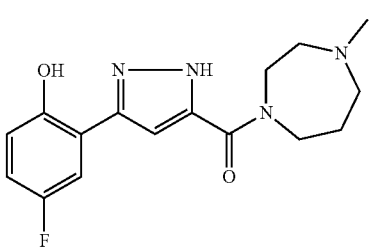
BRM2-134
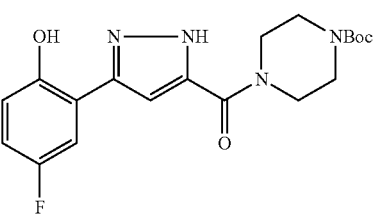
BRM2-135
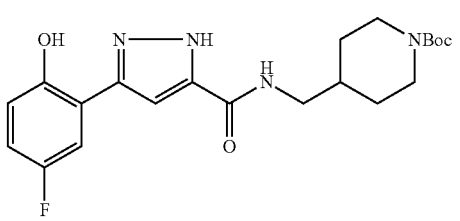

BRM2-136
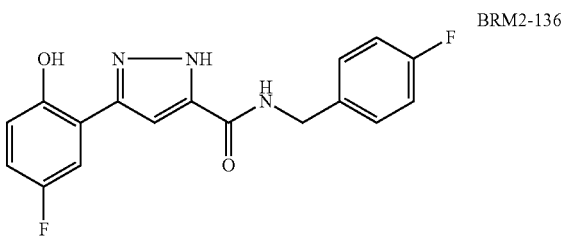
BRM2-137
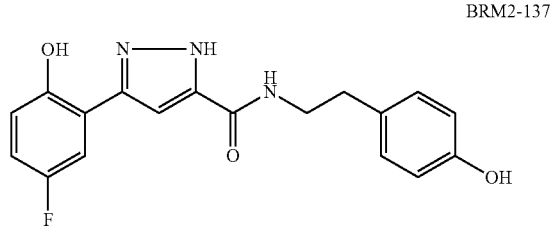
BRM2-138
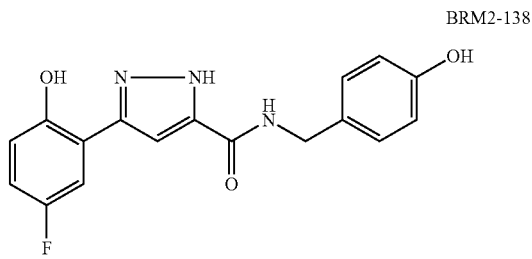
BRM2-139
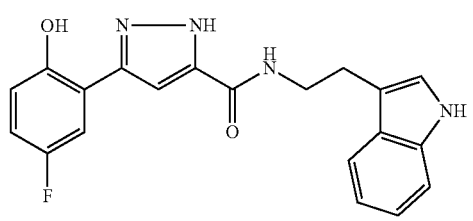
BRM2-140
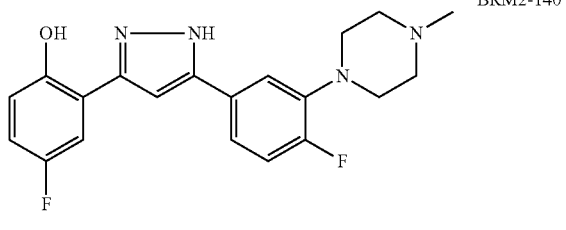
BRM2-141
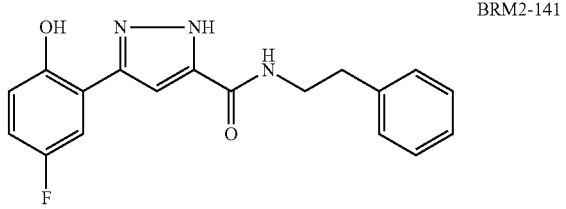
BRM2-142
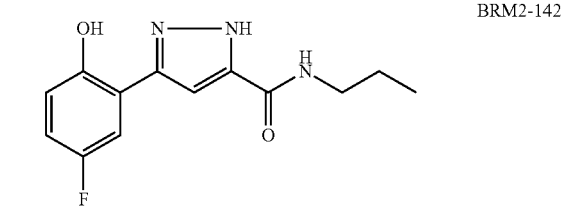
BRM2-143
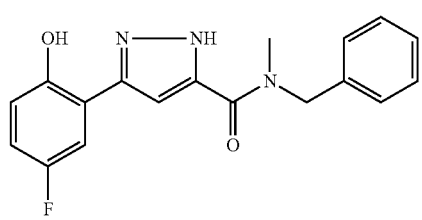 [SMILES: CN(Cc1ccccc1)C(=O)c1cc(-c2cc(F)ccc2O)n[nH]1]
BRM2-144
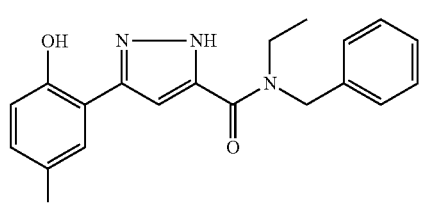
BRM2-145
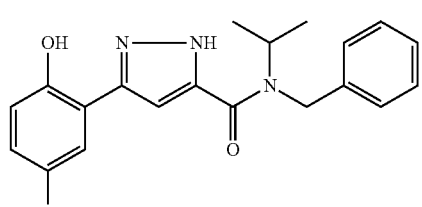
BRM2-146
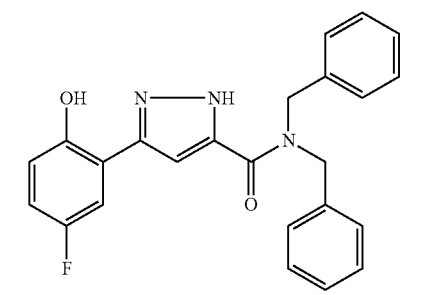
BRM2-147
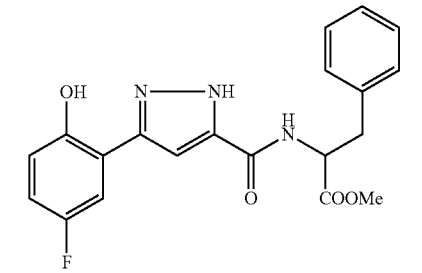
BRM2-148
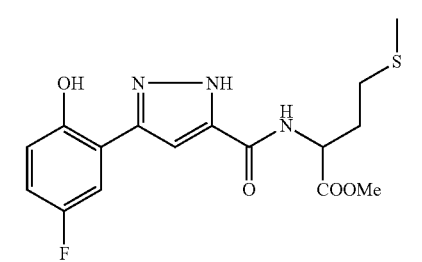

BRM2-149
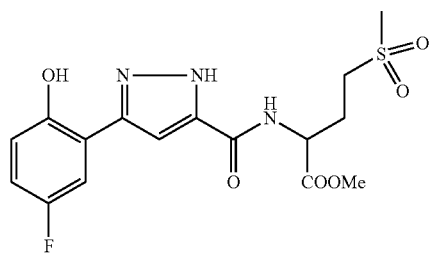
BRM2-150
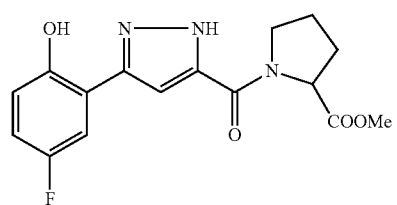 [SMILES: COC(=O)C1CCCN1C(=O)c1cc(-c2cc(F)ccc2O)n[nH]1]
BRM2-151
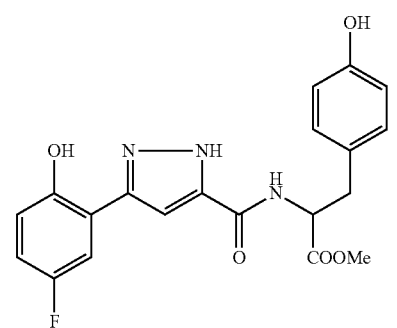
BRM2-152
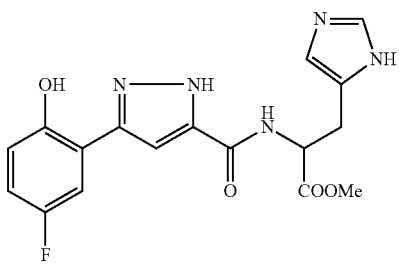 [SMILES: COC(=O)C(Cc1cnc[nH]1)NC(=O)c1cc(-c2cc(F)ccc2O)n[nH]1]
BRM2-153
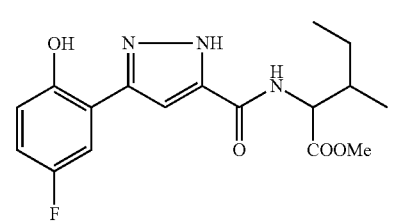
BRM2-154
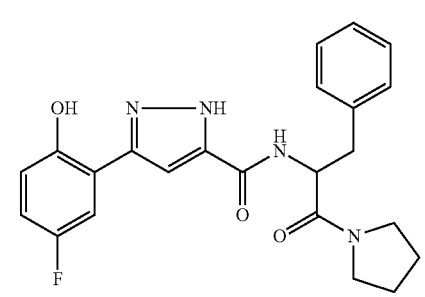
BRM2-155
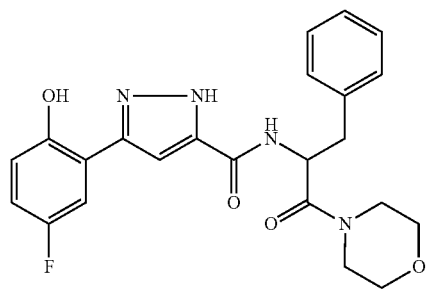
BRM2-156
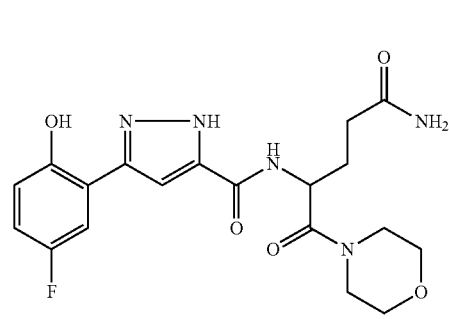 [SMILES: NC(=O)CCC(NC(=O)c1cc(-c2cc(F)ccc2O)n[nH]1)C(=O)N1CCOCC1]
BMR2-157
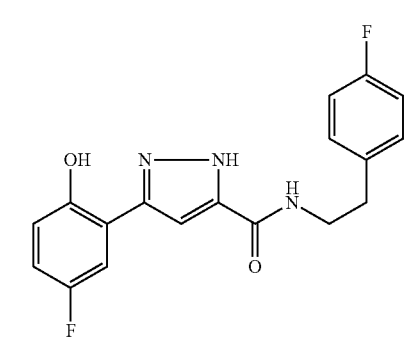 [SMILES: O=C(NCCc1ccc(F)cc1)c1cc(-c2cc(F)ccc2O)n[nH]1]
BRM2-158
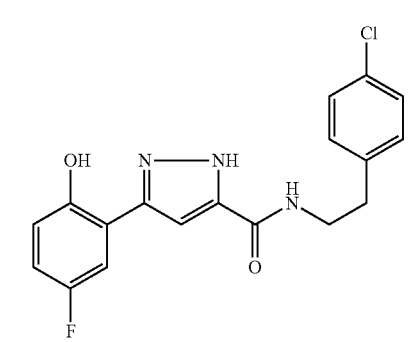
BRM2-159
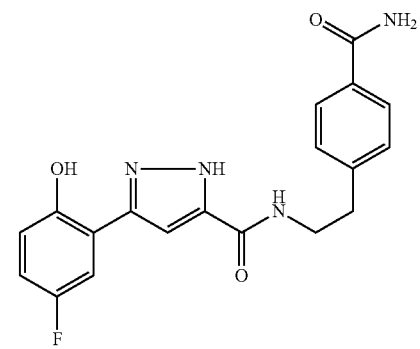

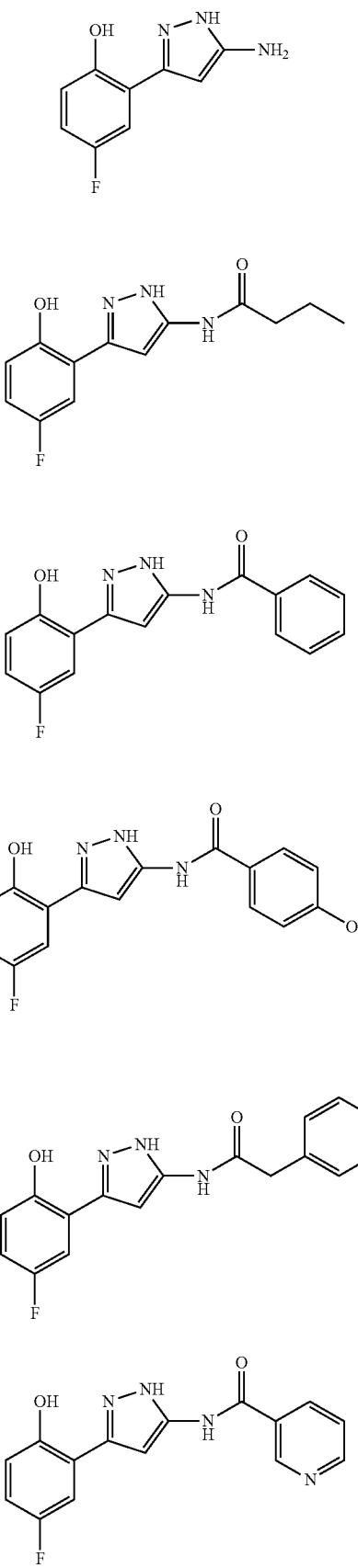
BRM2-160
BRM2-161
BRM2-162
BRM2-163
BRM2-164
BRM2-165
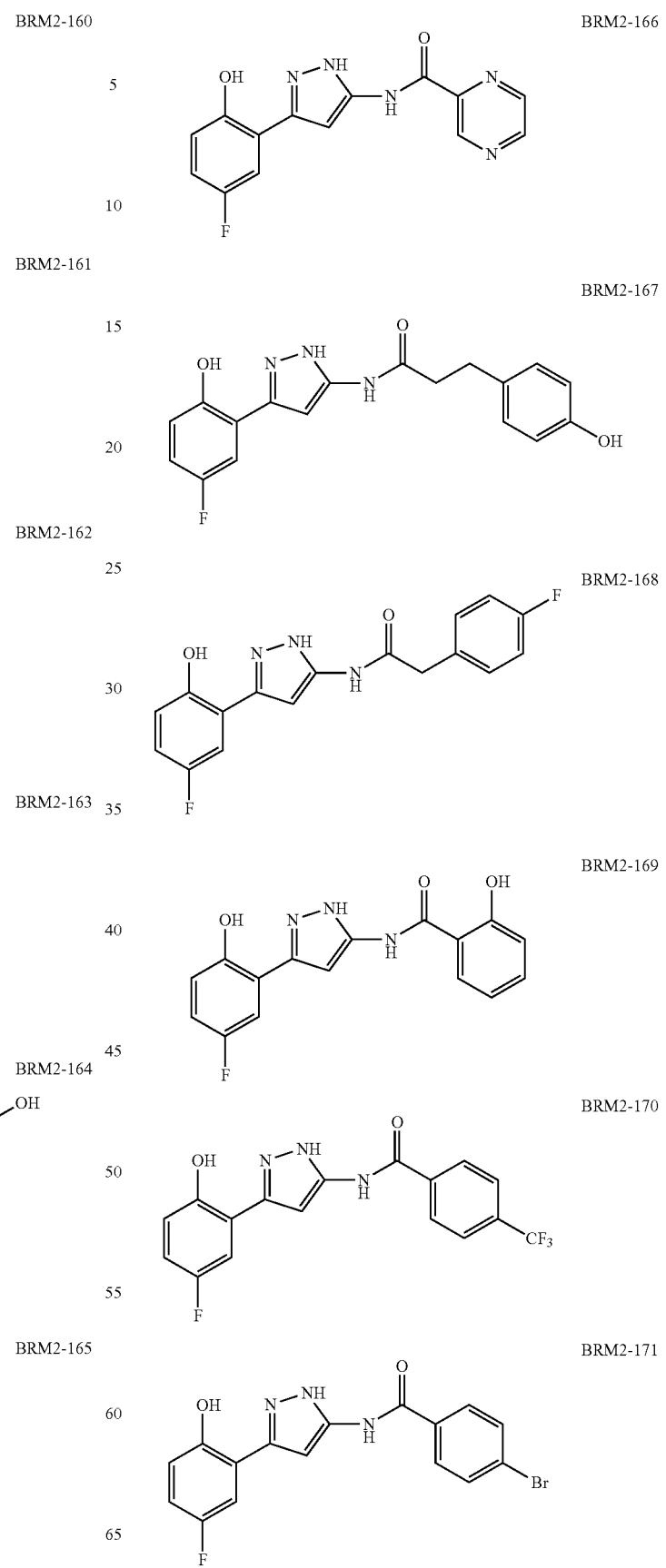
BRM2-166
BRM2-167
BRM2-168
BRM2-169
BRM2-170
BRM2-171

BMR2-172
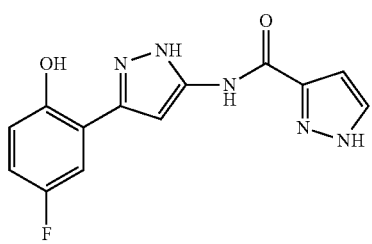
BRM2-173
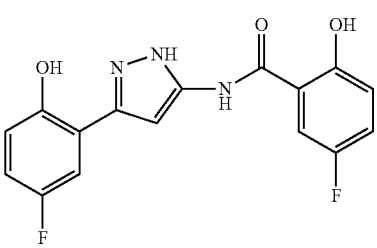 [SMILES: O=C(Nc1cc(-c2cc(F)ccc2O)n[nH]1)c1ccccc1]
BRM2-174
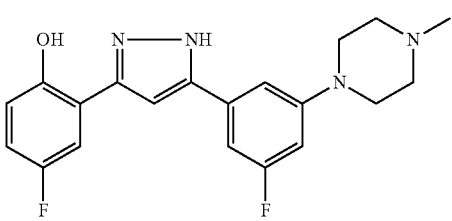
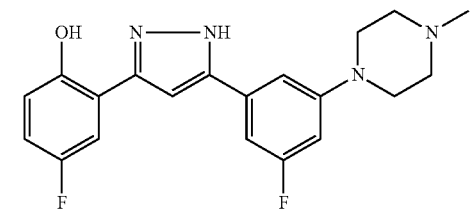
The compound represented by Formula (I) according to the present invention can be synthesized by employing the following reaction routes.
(Route 1) Synthesis of 4-Substituted Pyrazole Compounds
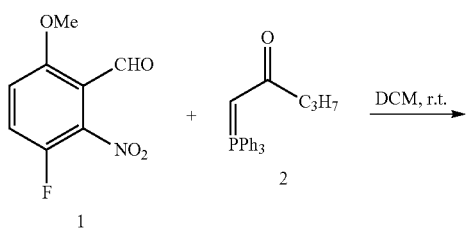
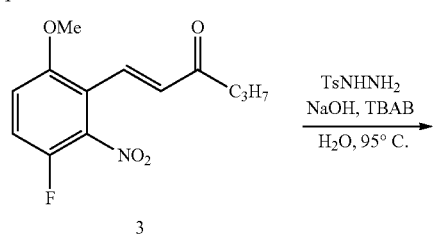
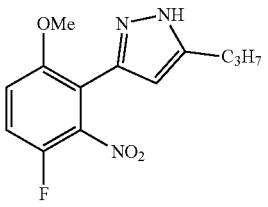
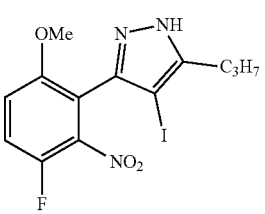
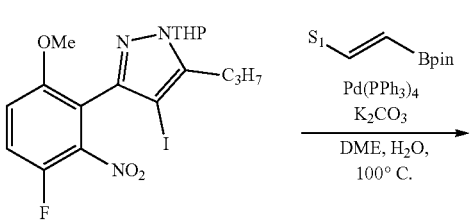
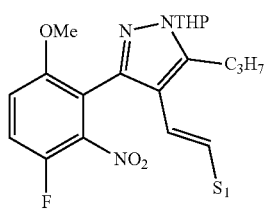
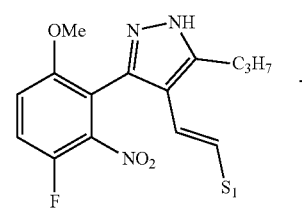
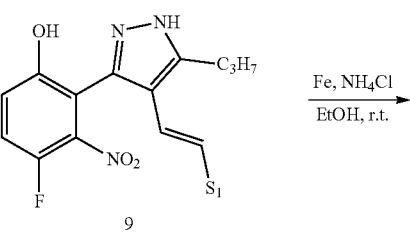

-continued

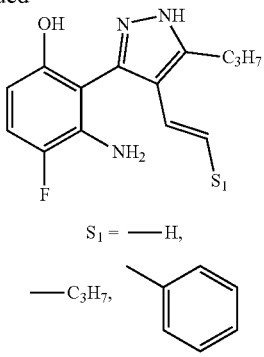

$S_1 = $ —H,

—$C_3H_7$,

—phenyl

A compound 1 (1 eq.) is added into a reaction solvent, namely dichloromethane to produce a solution, and a compound 2 (1.2 eq.) is added into the solution in batches to produce a reaction solution. The produced reaction solution is reacted at r.t. for 8 h, then dichloromethane (DCM) extraction is carried out, and separation is carried out using silica-gel column chromatography to produce an intermediate 3. The intermediate 3 (1 eq.), p-toiuenesulfonyl hydrozide (TsNHNH$_2$, 2 eq.) and tetrabutylammonium bromide (TBAB, 1 eq.) are slowly added into an aqueous solution of NaOH (3 eq.) in batches under stirring to produce a mixed solution. The produced mixed solution is stirred at 95° C. for 12 h to produce a reaction solution. The reaction solution is cooled to room temperature, and a pH value of the reaction solution is adjusted to 4-5 by using 2 N hydrochloric acid to produce a mixed solution. The produced mixed solution is extracted with an equal volume of ethyl acetate for three times. The organic phase is washed with water and saline, and then dried with anhydrous sodium sulfate. After the sodium sulfate is filtered out, the organic phase is removed using a rotary evaporator to produce a crude product. The produced crude product is separated and purified using the silica-gel column chromatography, so as to produce an intermediate 4. The intermediate 4 (1 eq.) and N-iodosuccinimide NIS (1.1 eq.) are dissolved in dichloromethane to be reacted at r.t. for 12 h, so as to produce an intermediate 5. The intermediate 5 (1.0 eq.), diheptyl phthalate (DHP) (2.0 eq.) and PPST (0.2 eq.) are dissolved in dichloromethane, reaction is carried out at r.t. for 12 h, and then separation is carried out through a neutral aluminum oxide chromatographic column to produce an intermediate 6. The intermediate 6 (1.0 eq.), vinylboronic acid pinacol ester (1.2 eq.), Pd(PPh$_3$)$_4$ (0.05 eq.) and K$_2$CO$_3$ (2.0 eq.) are dissolved in a mixed solvent of dimethyl ether (DME) and water, reaction is carried out at 100° C. for 12 h, and then separation is carried out through a neutral aluminum oxide chromatographic column to produce an intermediate 7. The intermediate 7 is dissolved in ethanol to produce a mixture, a solution of 2N HCl in ethanol is added, extraction is carried out through ethyl acetate, saturated sodium bicarbonate is added, and the organic phase is dried by rotary evaporation, so as to produce an intermediate 8 which is directly used for the reaction in the next step. The intermediate 8 is dissolved in dichloromethane, and added with BBr$_3$ (10 eq.) at −78° C. Then reaction is carried out at room temperature for 24 h. After the reaction is completed, and a solvent is removed by rotary evaporation under reduced pressure to produce a crude product, the crude product is dissolved in ethyl acetate, washed once with water and once with saline, the organic phase is dried, and then purified by silica-gel column chromatography to obtain an intermediate 9. The intermediate 9 is dissolved in ethanol, and added with an aqueous solution of reduced Fe powder and ammonium chloride to produce a mixture. The mixture is reacted at r.t. for 12 h, separation is carried out through silica-gel column chromatography to obtain the substituted pyrazole compounds.

(Route 2) Synthesis of 5-Substituted Pyrazole Compounds

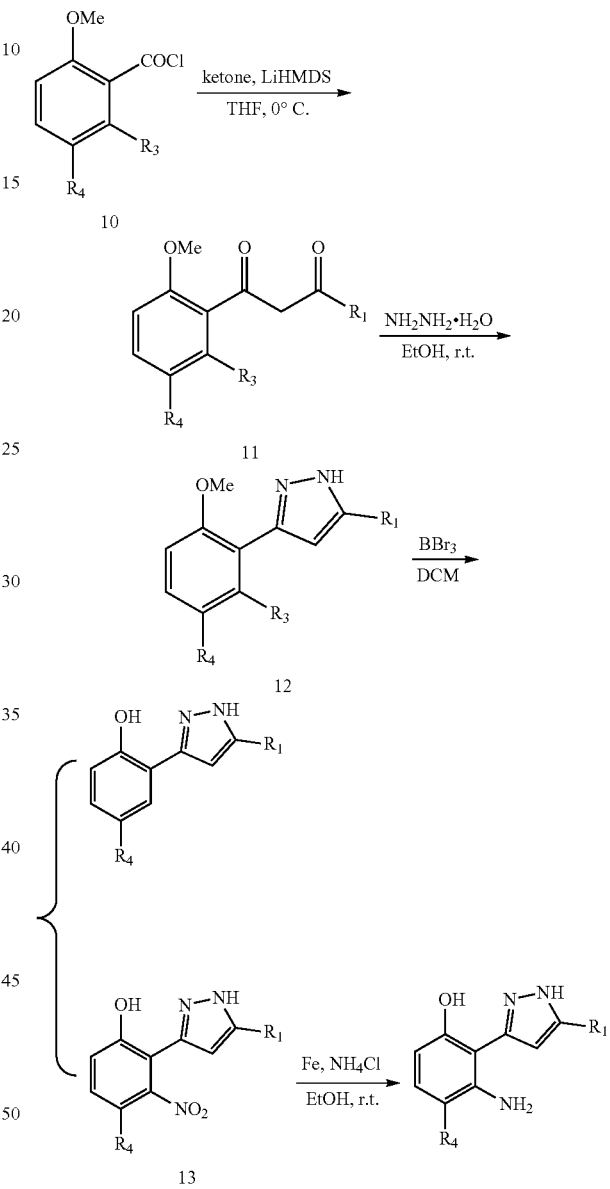

An intermediate 10 is dissolved in dry tetrahydrofuran (THF) to produce a mixture, and then the mixture is added dropwise into a reaction solution of ketone (1.1 eq.) and LiHMDS (1.5 eq.) in an ice bath to produce a reaction solution. The produced reaction solution is stirred at r.t. for 1 h, and then quenched by adding water to produce a solution. The solution is extracted by dichloromethane, and the organic phase is dried using anhydrous magnesium sulfate. After the anhydrous magnesium sulfate is filtered out, the dried organic phase is stirred with silica gel, and then separated and purified using a silica-gel chromatography column, so as to obtain an intermediate 11. The intermediate 11 is dissolved in methanol to produce a reaction solution, and NH$_2$NH$_2$.H$_2$O (3.0 eq.) is added dropwise into the reaction solution, reaction is carried out at r.t. for 12 h to produce a product, the product is dried by rotary evaporation to obtain a crude product, namely an intermediate 12 which is directly used for reaction in the next step. The intermediate 12 is dissolved in dichloromethane, BBr$_3$ (10 eq.) is added at −78° C. Then reaction is carried out at room temperature for 24 to produce a product. After the reaction is completed, the product is dried by rotary evaporation to obtain a crude product. The crude product is dissolved in ethyl acetate, washed once with water and once with saline, the organic phase is dried, and then purified by silica-gel column chromatography to obtain an intermediate 13. The intermediate 13 is dissolved in ethanol, and added with an aqueous solution of reduced Fe powder and ammonium chloride to produce a mixture, the mixture is reacted at r.t. for 12 h to produce a product, and the product is separated by silica-gel column chromatography to produce the 5-substituted pyrazole compounds.

(Route 3) Synthesis of 5-Aryl Substituted Pyrazole Derivatives

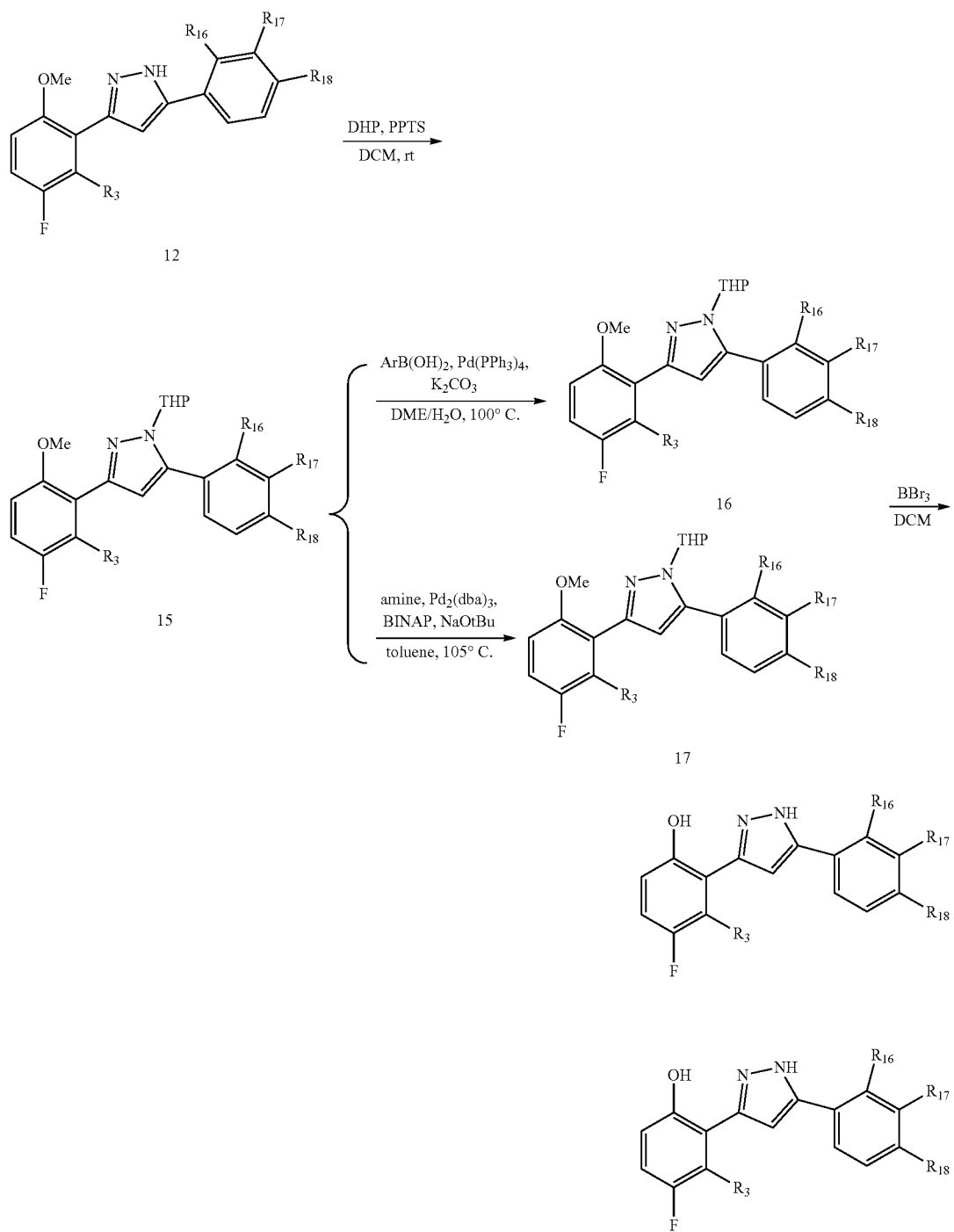

The intermediate 12 (1 eq.) and pyridinium p-toluenesulfonate (PPTS, 0.1 eq.) are dissolved in dichloromethane, then 3,4-dihydro-2H-pyran (DHP, 3 eq.) is added, reaction is carried out at room temperature for 24 h, after the reaction is completed, the organic phase is removed by rotary evaporation under reduced pressure to produce a crude product, and the crude product is separated by column chromatography with neutral aluminum oxide, so as to produce an intermediate 15;

the intermediate 15 (1 eq.) is dissolved in a mixed liquor of ethylene glycol dimethyl ether and water (DME:H$_2$O=4:1) to produce a mixture, the mixture is added with K$_2$CO$_3$ (2.5 eq.), Pd(PPh$_3$)$_4$ (0.1 eq.), an arylboronic acid compound (1.2 eq.), after nitrogen protection, heating is carried out to 100° C., reaction is carried out at 100° C. for 24 h, after the reaction is completed, the organic solvent is removed by rotary evaporation under reduced pressure to produce a product, then the product is extracted twice with ethyl acetate, and the organic phase is dried and then purified by silica-gel column chromatography to produce an intermediate 16; the intermediate 16 is dissolved in dichloromethane, BBr$_3$ (10 eq.) is added at −78° C., reaction is carried out at room temperature for 24 h, after the reaction is completed, the organic phase is dried by rotary evaporation to produce a crude product, the crude product is dissolved in ethyl acetate, washed once with water and once with saline, and the organic phase is dried, and then purified by silica-gel column chromatography to obtain an aromatic ring derivative of a pyrazole ring compound; and the intermediate 15 (1 eq.) and an amino compound (2 eq.) are dissolved in toluene, and then Pd$_2$(dba)$_3$ (0.05 eq.), 1,1'-binaphthalene-2,2'-bisdiphenylphosphine (BINAP, 0.1 eq.), and NaOtBu (2.5 eq.) are added, after protected by nitrogen displacement, a reaction flask is heated 105° C., and reaction is carried out for 24 h to produce a product, after the reaction is completed, the product is extracted with ethyl acetate, the organic phase is washed once with water and once with saline, dried, and then the dried organic phase is purified by silica-gel column chromatography to obtain an intermediate 17; and the intermediate 17 is dissolved in dichloromethane, BBr$_3$ (10 eq.) is added at −78° C., then Reaction is carried out at room temperature for 24 h, after the reaction is completed, the organic phase is dried by rotary evaporation to produce a crude product, the crude product is dissolved in ethyl acetate, washed once with water and once with saline, the organic phase is dried, and then purified by silica-gel column chromatography to obtain amino derivatives of pyrazole ring compounds.

(Route 4) Synthesis of Bis-N Heterocyclic Substituted Pyrazole Compounds

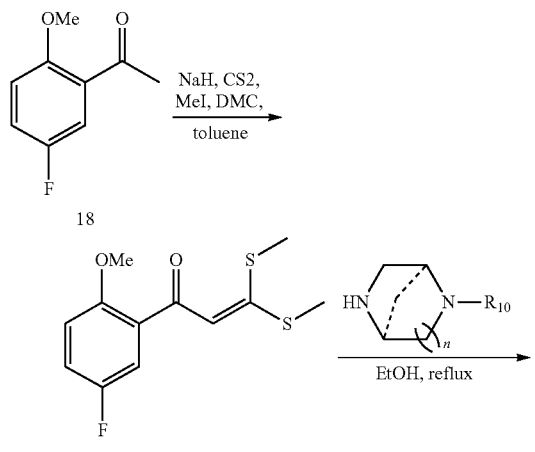

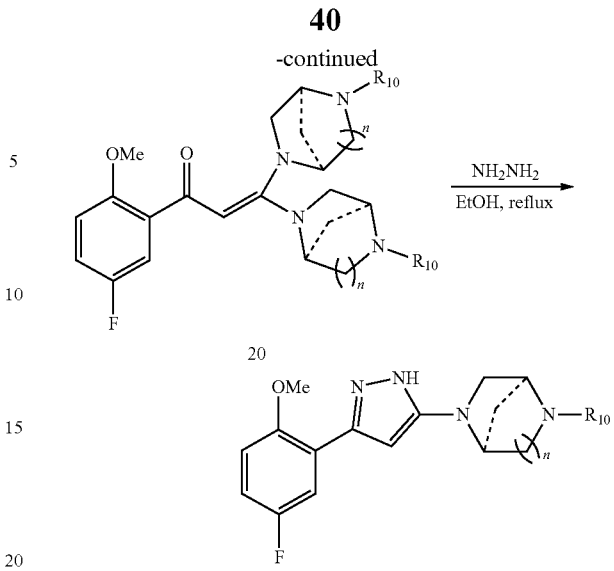

A compound 18 (1 eq.) is dissolved in anhydrous toluene, and added with carbon disulfide (1.6 eq.) and methyl iodide (3.5 eq.). A reactor is placed in ice bath, slowly added with NaH (2.2 eq.), and then slowly added dropwise with N,N-dimethylacetamide (2.2 eq.). After the addition, the reactor is raised to room temperature, reaction is carried out for two days, and after the reaction is completed, the reaction is quenched by adding water. The organic phase is washed once with water and once with saline, the washed organic phase is dried, and then purified by silica-gel column chromatography to obtain a compound 19. The compound 19 is dissolved in ethanol, and added with an amine compound R1 (2.2 eq.) to produce a mixture, and the mixture is heated under stirring to be subjected to reflux for 24 h. After reaction is completed, a produced product is directly purified by silica-gel column chromatography to produce a compound 20. The compound 20 is dissolved in absolute ethanol, and added with 98% hydrazine hydrate (2 eq.) to produce a mixture, and the mixture is heated to be subjected to reflux for 12 h. After reaction is completed, a produced product is directly purified by silica-gel column chromatography to obtain the amine-substituted pyrazole compounds.

(Route 5) Synthesis of p-Amide Aryl Substituted Pyrazole Skeleton Compounds

41

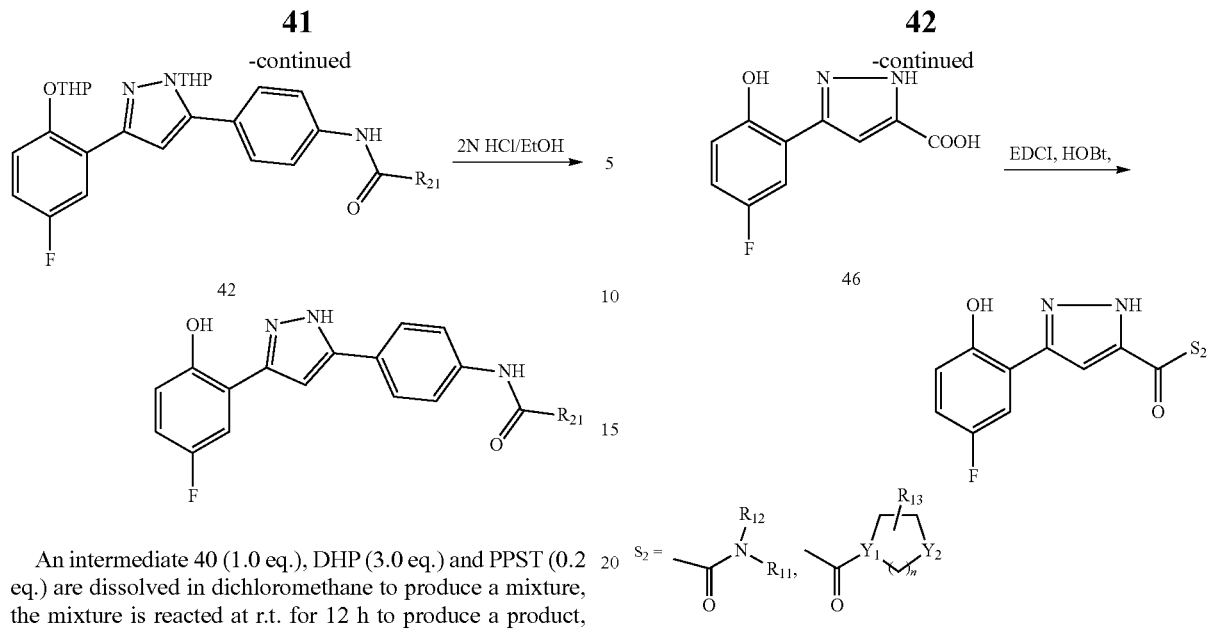

An intermediate 40 (1.0 eq.), DHP (3.0 eq.) and PPST (0.2 eq.) are dissolved in dichloromethane to produce a mixture, the mixture is reacted at r.t. for 12 h to produce a product, and then the product is separated through a neutral aluminum oxide chromatographic column to produce an intermediate 41. The intermediate 41 (1.0 eq.), amide (1.2 eq.), Pd(OAc)$_2$ (0.02 eq.), Xantphos (0.03 eq.) and Cs$_2$CO$_3$ (1.4 eq.) are dissolved in 1,4-dioxane to produce a mixture, the mixture is reacted at 100° C. for 12 h to produce a product, and then the product is separated through a neutral aluminum oxide chromatographic column to obtain an intermediate 42. The intermediate 42 is dissolved in ethanol, and added with 2N HCl in ethanol to produce a mixture, the mixture is extracted with ethyl acetate and added with saturated sodium bicarbonate to produce a crude product, and the crude product is dried, and then purified by silica-gel column chromatography to obtain the p-amide aryl substituted pyrazole skeleton compounds.

(Route 6) Synthesis of Pyrazole Amide Compounds

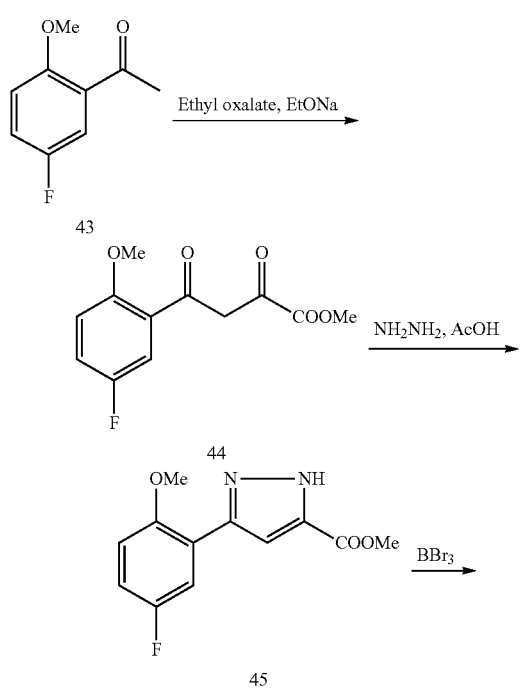

A compound 43 (1 eq.) is added dropwise into EtONa (2.3 eq.) and stirred at room temperature for 1 h, and then slowly added dropwise with diethyl oxalate to produce a mixture, the mixture is heated to be subjected to reflux for 4 h, reaction is carried out to produce a product, and then the product is cooled to room temperature, and then added with glacial acetic acid (4 eq.) to produce a large amount of white solids. The white solids are filtered, and then respectively washed with a small amount of water, ethanol, and ether to produce an intermediate 44. The intermediate 44 is dissolved in acetic acid, and then slowly added dropwise with hydrazine hydrate (1.2 eq.) in ice bath to produce a mixture, and the mixture is reacted overnight at room temperature. After the reaction is completed, a produced product is filtered, the filtered product is recrystallized in ethanol to obtain an intermediate 45. The intermediate 45 is dissolved in anhydrous dichloromethane, and added with BBr$_3$ (6 eq.) at −78° C., and after 1 h, reaction is carried out overnight at room temperature. After the reaction is completed, the reaction is quenched by slowly adding water. The organic phase is removed with a rotary evaporator to produce a reaction solution. The pH value of the reaction solution is adjusted to 5. Extraction is carried out through ethyl acetate to produce a product, the product is dried, and subjected to rotary evaporation under reduced pressure to remove the organic solvent, so as to obtain an intermediate 46. The intermediate 46, EDCI (1.2 eq.) and HOBt (1.2 eq.) are added into anhydrous DMF, stirred for half an hour and then added with a corresponding amine compound R to produce a mixture, and the mixture reacted for 12 hours to produce a product. After the reaction is completed, the product is added with ethyl acetate, and the organic phase is washed for three times with a saturated ammonium chloride solution and once with a saturated sodium chloride solution, the washed organic phase is dried through anhydrous magnesium sulfate, and then the dried organic phase is purified by silica-gel column chromatography to obtain the pyrazole amide compounds as the final products.

(Route 7) Synthesis of 5-Substituted Aminopyrazole Compounds

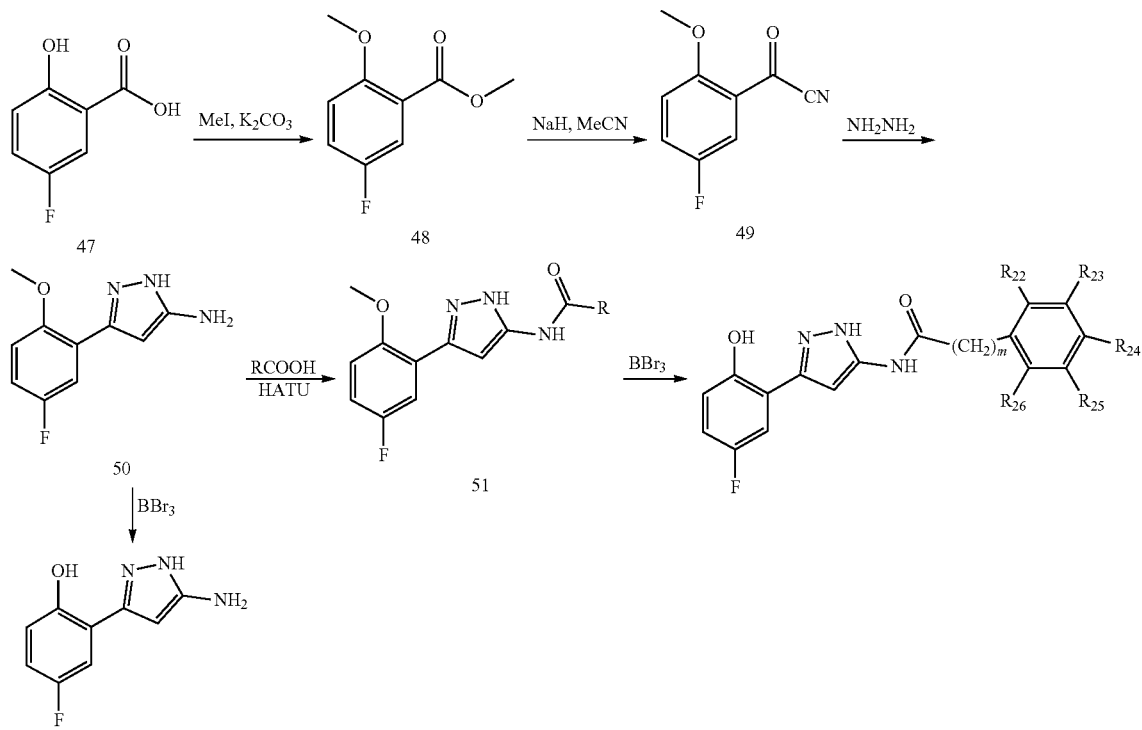

A compound 47 (1.0 eq.), methyl iodide (3.0 eq.), and potassium carbonate (3.0 eq.) are dissolved in a certain amount of acetone solution, and reacted under stirring at 40° C. for 12 h. The solvent is dried by rotary evaporation, extraction is carried with ethyl acetate and saturated sodium bicarbonate is added to produce a crude product. The crude product is dried, and purified by silica-gel column chromatography to obtain an intermediate 48. The intermediate 48 (1.0 eq.) is dissolved in ultra-dry toluene, added with acetonitrile (3.0 eq.), then added with sodium hydride (3.0 eq.), and added with a buffer balloon to produce a mixture, and the mixture heated to react at 90° C. for 3 h. The solvent is dried by rotary evaporation, extraction is carried out with ethyl acetate, and saturated sodium bicarbonate is added to produce a crude product. The crude product is dried, and purified by silica-gel column chromatography to obtain an intermediate 49. The intermediate 49 (1.0 eq.) and hydrazine monohydrate (1.2 eq.) are dissolved in ethanol together, and then added with glacial acetic acid (6.0 eq.) to produce a mixture, and the mixture is heated to react at 50° C. for 3 h. The solvent is dried by rotary evaporation, extraction is carried out with ethyl acetate, and saturated sodium bicarbonate is added to produce a crude product. The crude product is dried, and purified by silica-gel column chromatography to obtain an intermediate 50. The intermediate 50 and different types of carboxylic acids are added into a solvent of DMF in one to one equivalent, and added with HATU (1.5 eq.) and DIPEA (1.5 eq.) to produce a mixture, the mixture is reacted at 70° C. for 12 h to produce a product, and the product is extracted with ethyl acetate to produce a crude product. The crude product is dried, and purified by silica-gel column chromatography to obtain an intermediate 51. The intermediate 51 or 50 (1 eq.) is dissolved in ultra-dry DCM, and added with boron tribromide (8 eq.) at 0° C. to produce a mixture, and the mixture is reacted under stirring at room temperature for 12 h. The solvent is dried by rotary evaporation, extraction is carried out with ethyl acetate and saturated sodium bicarbonate is added to produce a crude product. The crude product is dried, and purified by silica-gel column chromatography to obtain the 5-substituted aminopyrazole compounds as the final products.

The pharmaceutically acceptable salt of the present invention includes an acid addition salt and a base addition salt.

The acid addition salt includes, but is not limited to salts from an inorganic acid such as hydrochloric acid, nitric acid, phosphoric acid, sulfuric acid, hydrobromic acid, hydroiodic acid and phosphonic acid; and salts from an organic acid such as aliphatic monocarboxylic acid and dicarboxylic acid, phenyl-substituted alkanoic acid, hydroxyalkanoic acid, alkanedioic acid, aromatic acid, and salts of aliphatic and aromatic sulfonic acids. Therefore, these salts include, but are not limited to sulfates, pyrosulfates, bisulfates, sulfites, bisulfites, nitrates, phosphates, monohydrogen phosphates, dihydrogen phosphates, metaphosphates, pyrophosphates, hydrochlorides, hydrobromides, iodates, acetates, propionates, octanoates, isobutyrates, oxalates, malonates, succinates, suberates, sebacates, fumarates, maleates, amygdalates, benzoates, chlorobenzoates, methyl benzoates, dinitrobenzoates, phthalates, benzene sulfonates, tosylates, phenyl acetates, citrates, lactates, maleates, tartrates and methanesulfonates, and also include salts from amino acids, such as arginine salts, gluconates and galacturonates. The acid addition salt can be prepared by contacting a free base with a sufficient amount of the desired acid to form a salt in a conventional manner. The free base form can be regenerated by contacting the salt with a base, and the free base can be isolated in a conventional manner.

The alkali addition salt is formed with metals or amines, such as hydroxides of alkali metals and alkaline earth metals, or with organic amines. Examples of metals used as cations include, but are not limited to sodium, potassium, magnesium, and calcium. Examples of suitable amines include, but are not limited to N,N'-dibenzylethylenediamine, chloroprocaine, choline, diethanolamine, ethylenediamine (ethane-1,2-diamine), N-methylglucosamine, and procaine. The base addition salt can be prepared by contacting a free acid with a sufficient amount of the desired base to form a salt in a conventional manner. The free acid form can be regenerated by contacting the salt with an acid, and the free acid can be isolated in a conventional manner.

The stereoisomer described in the present invention includes forms of enantiomers, diastereomers and geometric isomers. Some compounds of the present invention have a cycloalkyl group which can be substituted on more than one carbon atom thereof, in this case, all geometric forms, including cis and trans forms, and mixtures thereof are within the scope of the present invention.

The solvate of the present invention refers to physical bonding of the compound of the present invention to one or more solvent molecules. The physical bonding includes various degrees of ionic and covalent bondings, including a hydrogen bonding. In certain cases, a solvate can be separated, for example when one or more solvent molecules are doped into crystal lattices of a crystalline solid. The "solvate" includes a solution-phase and separable solvate. The representative solvates include ethylates, methylates, and the like. A "hydrate" is a solvate in which one or more solvent molecules are $H_2O$.

The prodrug described in the present invention refers to a form of the compound represented by Formula I, which is suitable for administration to a patient without excessive toxicity, irritation and allergy, etc., is effective for its application purpose, and includes acetal, ester and zwitter-ionic forms. The prodrug is transformed in vivo (for example by hydrolysis in blood) to obtain a parent compound of the above formula.

The present invention further provides a pharmaceutical composition including a compound of the present invention (e.g., the compound represented by Formula I, and a pharmaceutically acceptable salt, stereoisomer, ester, prodrug and solvate thereof), and a pharmaceutically acceptable carrier, diluent or excipient. Preferably, the pharmaceutical composition contains a therapeutically effective amount of the compound of the present invention.

The compounds of the present invention can be formulated into pharmaceutical compositions in the following forms: syrup, elixir, suspensions, powder, granules, tablets, capsules, lozenges, aqueous solutions, creams, ointments, lotions, gels, emulsion, etc.

A pharmaceutical preparation is preferably in a unit dosage form. In such a form, the preparation is subdivided into unit dosages containing appropriate quantities of active components. The unit dosage form can be a packaged preparation containing discrete quantities of the preparation, such as tablets, capsules, and powder packaged in vials or ampoules. Furthermore, the unit dosage form can be a capsule or tablet, or any of these dosage forms which may be in an appropriate number in a packaged form.

The amount of the active components in a unit-dosage preparation can be changed or adjusted between 0.001 mg and 1000 mg, depending on the specific application and potency of the active components. If desired, the composition may also contain other suitable therapeutic agents.

The pharmaceutically acceptable carrier depends in part on the specific administered composition and on a specific method of administration of the composition. Therefore, there are various suitable preparations for the pharmaceutical composition of the present invention.

The compounds of the present invention, alone or in combination with other suitable components, are formulated into aerosols (i.e., they can be "aerosolized") to be administered via inhalation. Aerosols can be placed in acceptable pressurized propellants such as dichlorodifluorohexane, propane and nitrogen.

Preparations suitable for parenteral administration, for example through intravenous, intramuscular, intradermal, and subcutaneous routes, include aqueous and non-aqueous isotonic sterile injections, which may contain antioxidants, buffers, bacteriostatic agents, and solutes that make the preparation be isotonic with the blood of a recipient; and aqueous and non-aqueous sterile suspensions, which may contain suspending agents, solubilizers, thickeners, stabilizers and preservatives. In the practice of the present invention, the composition can be administered by, for example, intravenous infusion, oral, topical, intraperitoneal, intravesical, and intrathecal ways. The preparations of the composition may be presented in unit-dosage or multi-dosage sealed containers, such as ampoules and vials. Solutions and suspensions for injection can be prepared from sterile powders, granules and tablets previously described.

In the context of the present invention, the dosage administrated to a subject should be sufficient to produce a beneficial therapeutic response in the subject over time. The dosage depends on the potency of a specific compound as used and the condition of the subject, as well as the body weight or body surface area of a subject to be treated. The size of the dosage will depend on the existence, nature, and extent of any adverse side effect generated along with the administration of the specific compound in the specific subject. During determination of the effective amount of the compound to be administered in the treatment or prevention of the diseases being treated, a physician can evaluate factors such as the circulating plasma level of the compound, the toxicity of the compound, and/or the disease progression to determine the effective amount.

The present invention also provides use of the compound represented by Formula (I), and a pharmaceutically acceptable salt, stereoisomer, ester, prodrug and solvate thereof in the prevention and/or treatment of cancers.

The present invention also provides use of the compounds represented by formula (I), and a pharmaceutically acceptable salt, stereoisomer, ester, prodrug and solvate thereof in cancer immunotherapy.

The present invention also provides use of the compound represented by formula (I) and a pharmaceutically acceptable salt, stereoisomer, ester, prodrug and solvate thereof in the preparation of a medication for preventing and/or treating cancers.

The cancers described in the present invention include lymphoma, blastoma, medulloblastoma, retinoblastoma, sarcoma, liposarcoma, synovial cell sarcoma, neuroendocrine neoplasm, carcinoid tumor, gastrinoma, islet-cell carcinoma, mesothelioma, schwannoma, acoustic neuroma, meningioma, adenocarcinoma, melanoma, leukemia or lymphoid malignancies, squamous-cell carcinoma, squamous cell carcinoma, lung cancer, small cell lung cancer, non-small cell lung cancer, adenocarcinoma lung cancer, lung squamous carcinoma, peritoneal cancer, hepatocellular carcinoma, gastric cancer, intestinal cancer, pancreatic cancer, glioblastoma, cervical cancer, ovarian cancer, liver cancer, bladder cancer, hepatic carcinoma, breast cancer, metastatic breast cancer, colon cancer, rectal cancer, colorectal cancer, uterine cancer, salivary gland carcinoma, kidney cancer, prostate cancer, vulvar carcinoma, thyroid cancer, hepatoma, anal cancer, penile neoplasms, Merkel cell carcinoma, esophageal carcinoma, biliary tract neoplasms, head and neck neoplasm, and hematologic malignancies.

As used in the present invention, the term "$C_0$ alkyl" refers to H, and thus $C_{0-10}$ alkyl includes H, $C_1$ alkyl, $C_2$ alkyl, $C_3$ alkyl, $C_4$ alkyl, $C_5$ alkyl, $C_6$ alkyl, $C_7$ alkyl, $C_8$ alkyl, $C_9$ alkyl, and $C_{10}$ alkyl.

As used in the present invention, the term "$C_{1-10}$ alkylene" includes $C_1$ alkylene, $C_2$ alkylene, $C_3$ alkylene, $C_4$ alkylene, $C_5$ alkylene, $C_6$ alkylene, $C_7$ alkylene, $C_8$ alkylene, $C_9$ alkylene, and $C_{10}$ alkylene.

As used in the present invention, the term "$C_{3-10}$ cycloalkyl" includes $C_3$ cycloalkyl, $C_4$ cycloalkyl, $C_5$ cycloalkyl, $C_6$ cycloalkyl, $C_7$ cycloalkyl, $C_8$ cycloalkyl, $C_9$ cycloalkyl, and $C_{10}$ cycloalkyl.

As used in the present invention, the term "$C_{1-6}$ alkyl" includes H, $C_1$ alkyl, $C_2$ alkyl, $C_3$ alkyl, $C_4$ alkyl, $C_5$ alkyl, and $C_6$ alkyl.

As used in the present invention, the term "linear $C_{1-6}$ alkyl" includes methyl, ethyl, linear $C_3$ alkyl, linear $C_4$ alkyl, linear $C_5$ alkyl, and linear $C_6$ alkyl.

As used in the present invention, the term "$C_{3-6}$ cycloalkyl" includes $C_3$ cycloalkyl, $C_4$ cycloalkyl, $C_5$ cycloalkyl, and $C_6$ cycloalkyl.

As used in the present invention, the term "halogen" includes fluorine, chlorine, bromine and iodine.

As used in the present invention, the term "heterocycloalkyl" refers to a non-aromatic saturated monocyclic or polycyclic ring system containing 3-10 ring atoms, and preferably 5-10 ring atoms, wherein one or more of the ring atoms are not carbon atoms, but are for example nitrogen, oxygen or sulfur atoms. Preferably, the heterocycloalkyl" contains 5-6 ring atoms. The prefixes aza, oxa or thio before the heterocycloalkyl respectively refers to that there is at least one nitrogen, oxygen or sulfur atom used as a ring atom. Representative monocyclic heterocycloalkyls include piperidinyl, pyrrolidinyl, piperazinyl, morpholinyl, thiomorpholinyl, thiazolidinyl, 1,3-dioxolyl, 1,4-dioxane, tetrahydrofuranyl, tetrahydrothienyl, tetrahydrothiopyranyl, etc.

As used in the present invention, the term "heterocycloaryl" refers to an aromatic monocyclic or polycyclic ring system containing 5-14 ring atoms, and preferably 5-10 ring atoms, wherein one or more of the ring atoms are not carbon atoms, but are for example nitrogen, oxygen or sulfur atoms. Preferably, the heterocycloaryl contains 5-6 ring atoms. Representative heterocycloaryls include pyrazinyl, furyl, thienyl, pyridyl, pyrimidinyl, isoxazolyl, isothiazolyl, oxazolyl, thiazolyl, pyrazolyl, furazyl, pyrrolyl, pyrazolyl, triazolyl, 1,2,4-thiadiazolyl, pyrazinyl, pyridazinyl, quinoxalinyl, 2,3-diazenaphthyl, imidazo[1,2-a]pyridine, imidazo[2,1-b]thiazolyl, benzofurazyl, indolyl, azaindolyl, benzimidazolyl, benzothienyl, quinolinyl, imidazolyl, thienopyridyl, quinazolinyl, thienopyrimidinyl, pyrrolopyridinyl, imidazopyridinyl, isoquinolinyl, benzoazaindolyl, 1,2,4-triazinyl, benzothiazolyl, etc.

As used in the present invention, the term "Me" represents an abbreviation for methyl.

As used in the present invention, the term "Ph" represents an abbreviation for phenyl.

As used in the present invention, the term "Boc" as represents an abbreviation for t-butyloxycarboryl.

As used in the present invention, the term "unit dosage form" refers to a physically discrete unit which is suitable as single dosage for human subjects and other mammals, each unit contains an active substance at a predetermined amount which as calculated can produce a desired preventive or therapeutic effect during the process of treatment when used in combination with a desired pharmaceutical carrier.

As used in the present invention, the term "auxiliary material" means that this component has no biological activity or other undesirable active impurities. For example, the component can be incorporated into the disclosed pharmaceutical preparation and administrated to a patient, without causing any significant adverse biological effects or interacting with other ingredients contained in the preparation in a harmful manner.

As used in the present invention, the term "treatment/treat/treating" includes inhibiting, delaying, alleviating, weakening, limiting, relieving or regressing a disease, disorder, signs or status, the occurrence and/or progression thereof, and/or symptoms thereof.

As used in the present invention, the term "prevention/prevent/preventing" includes reducing the risk of suffering from, infecting with or experiencing a disease, disorder, signs or status, the occurrence and/or progression thereof, and/or symptoms thereof.

As used in the present invention, the term "comprise/comprising" or "include/including" means "open" or "inclusive" terms, such that they include the listed elements, but also allow the inclusion of additional, unmentioned elements.

As used in the present invention, the term "about" generally means +/−5% of the referred value, more generally +/−4% of the referred value, more generally +/−3% of the referred value, more generally +/−2% of the referred value, more generally +/−1% of the referred value, and more generally +/−0.5% of the referred value.

DETAILED DESCRIPTION OF THE EMBODIMENTS

The technical solutions in embodiments of the present invention are clearly and completely described below. Apparently, the described embodiments are merely a part not all of the embodiments of the present invention. All other embodiments obtained by those of ordinary skill in the art based on the embodiments of the present invention without creative efforts are within the protective scope of the present invention.

Example 1

Synthesis of 4-Substituted Pyrazole Compounds (BRM2-1 to BRM2-3)

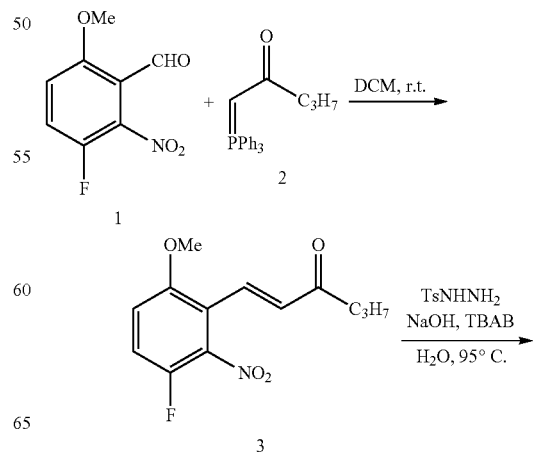

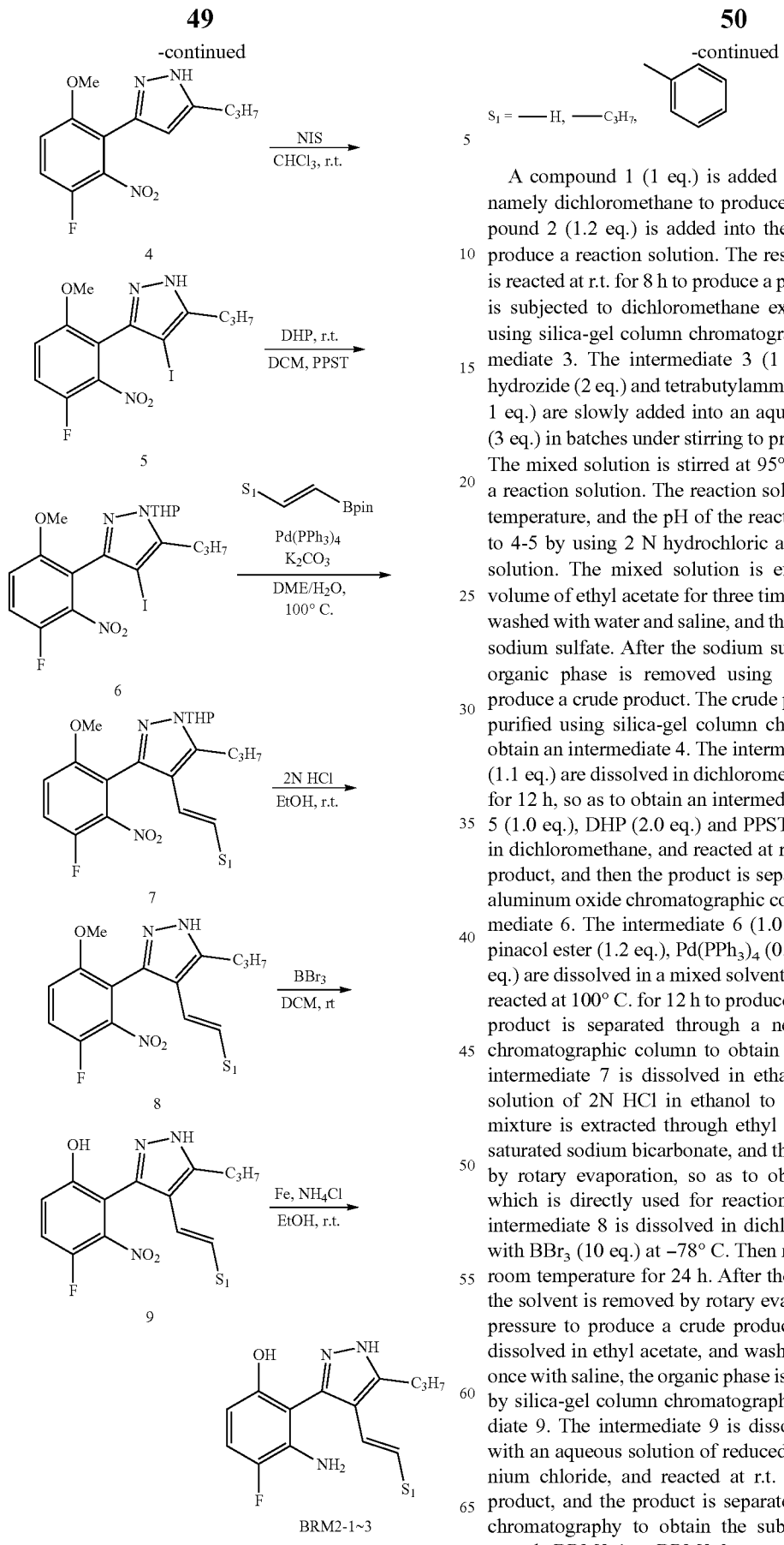

$S_1 = \text{—H}, \text{—}C_3H_7,$ (tolyl)

A compound 1 (1 eq.) is added into a reaction solvent, namely dichloromethane to produce a solution, and a compound 2 (1.2 eq.) is added into the solution in batches to produce a reaction solution. The resulting reaction solution is reacted at r.t. for 8 h to produce a product, then the product is subjected to dichloromethane extraction, and separated using silica-gel column chromatography to obtain an intermediate 3. The intermediate 3 (1 eq.), p-toiuenesulfonyl hydrozide (2 eq.) and tetrabutylammonium bromide (TBAB, 1 eq.) are slowly added into an aqueous solution of NaOH (3 eq.) in batches under stirring to produce a mixed solution. The mixed solution is stirred at 95° C. for 12 h to produce a reaction solution. The reaction solution is cooled to room temperature, and the pH of the reaction solution is adjusted to 4-5 by using 2 N hydrochloric acid to produce a mixed solution. The mixed solution is extracted with an equal volume of ethyl acetate for three times. The organic phase is washed with water and saline, and then dried with anhydrous sodium sulfate. After the sodium sulfate is filtered out, the organic phase is removed using a rotary evaporator to produce a crude product. The crude product is separated and purified using silica-gel column chromatography, so as to obtain an intermediate 4. The intermediate 4 (1 eq.) and NIS (1.1 eq.) are dissolved in dichloromethane, and reacted at r.t. for 12 h, so as to obtain an intermediate 5. The intermediate 5 (1.0 eq.), DHP (2.0 eq.) and PPST (0.2 eq.) are dissolved in dichloromethane, and reacted at r.t. for 12 h to produce a product, and then the product is separated through a neutral aluminum oxide chromatographic column to obtain an intermediate 6. The intermediate 6 (1.0 eq.), vinylboronic acid pinacol ester (1.2 eq.), Pd(PPh$_3$)$_4$ (0.05 eq.) and K$_2$CO$_3$ (2.0 eq.) are dissolved in a mixed solvent of DME and water, and reacted at 100° C. for 12 h to produce a product, and then the product is separated through a neutral aluminum oxide chromatographic column to obtain an intermediate 7. The intermediate 7 is dissolved in ethanol, and added with a solution of 2N HCl in ethanol to produce a mixture, the mixture is extracted through ethyl acetate and added with saturated sodium bicarbonate, and the organic phase is dried by rotary evaporation, so as to obtain an intermediate 8 which is directly used for reaction in the next step. The intermediate 8 is dissolved in dichloromethane, and added with BBr$_3$ (10 eq.) at −78° C. Then reaction is carried out at room temperature for 24 h. After the reaction is completed, the solvent is removed by rotary evaporation under reduced pressure to produce a crude product, the crude product is dissolved in ethyl acetate, and washed once with water and once with saline, the organic phase is dried, and then purified by silica-gel column chromatography to obtain an intermediate 9. The intermediate 9 is dissolved in ethanol, added with an aqueous solution of reduced Fe powder and ammonium chloride, and reacted at r.t. for 12 h to produce a product, and the product is separated by silica-gel column chromatography to obtain the substituted pyrazole compounds BRM2-1 to BRM2-3.

Example 2

Synthesis of 5-Substituted Pyrazole Compounds (BRM2-4 to BRM2-20)

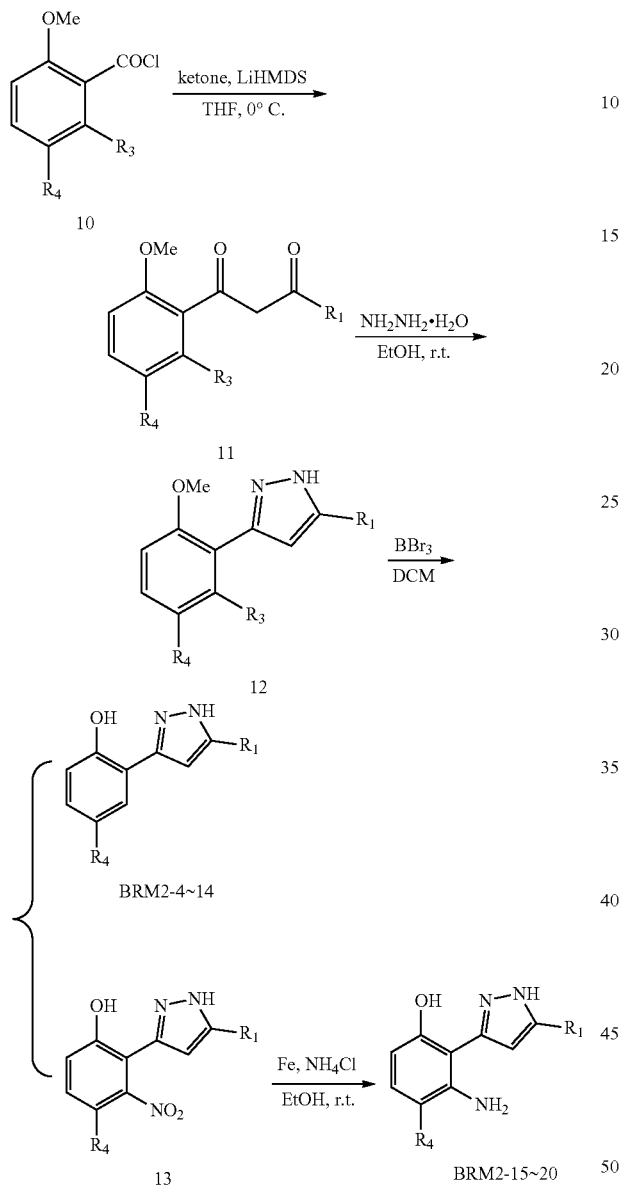

An intermediate 10 is dissolved in dry tetrahydrofuran to produce a mixture, and then the mixture is added dropwise into a reaction solution of ketone (1.1 eq.) and LiHMDS (1.5 eq.) in ice bath to produce a reaction solution. The reaction solution is stirred at r.t. for 1 h, and then quenched by adding water. Extraction is carried out by dichloromethane, and the organic phase is dried through anhydrous magnesium sulfate. After the anhydrous magnesium sulfate is filtered out, the dried organic phase is stirred with silica gel, and then separated and purified by using a silica-gel chromatography column, so as to obtain an intermediate 11. The intermediate 11 is dissolved in methanol to produce a reaction solution, and $NH_2NH_2 \cdot H_2O$ (3.0 eq.) is added dropwise into the reaction solution to produce a mixture. The mixture is reacted at r.t. for 12 h to produce a product, the product is dried by rotary evaporation to obtain a crude product, namely an intermediate 12 which is directly used for reaction in the next step. The intermediate 12 is dissolved in dichloromethane, and added with $BBr_3$ (10 eq.) at −78° C. Then the reaction is carried out at room temperature for 24 h to produce a product. After the reaction is completed, the product is dried by rotary evaporation to produce a crude product. The crude product is dissolved in ethyl acetate, and washed once with water and once with saline, the organic phase is dried, and purified by silica-gel column chromatography to obtain an intermediate 13. The intermediate 13 is dissolved in ethanol, and added with an aqueous solution of reduced Fe powder and ammonium chloride to produce a mixture, the mixture is reacted at r.t. for 12 h to produce a product, and the product is separated by silica-gel column chromatography to obtain the compounds BRM2-4 to BRM2-20.

Example 3

Synthesis of Derivatives of 5-Aryl Substituted Pyrazole Compounds (BRM2-21 to BRM2-39)

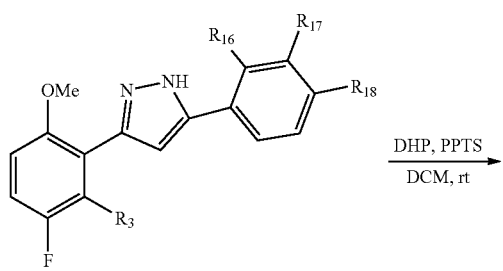

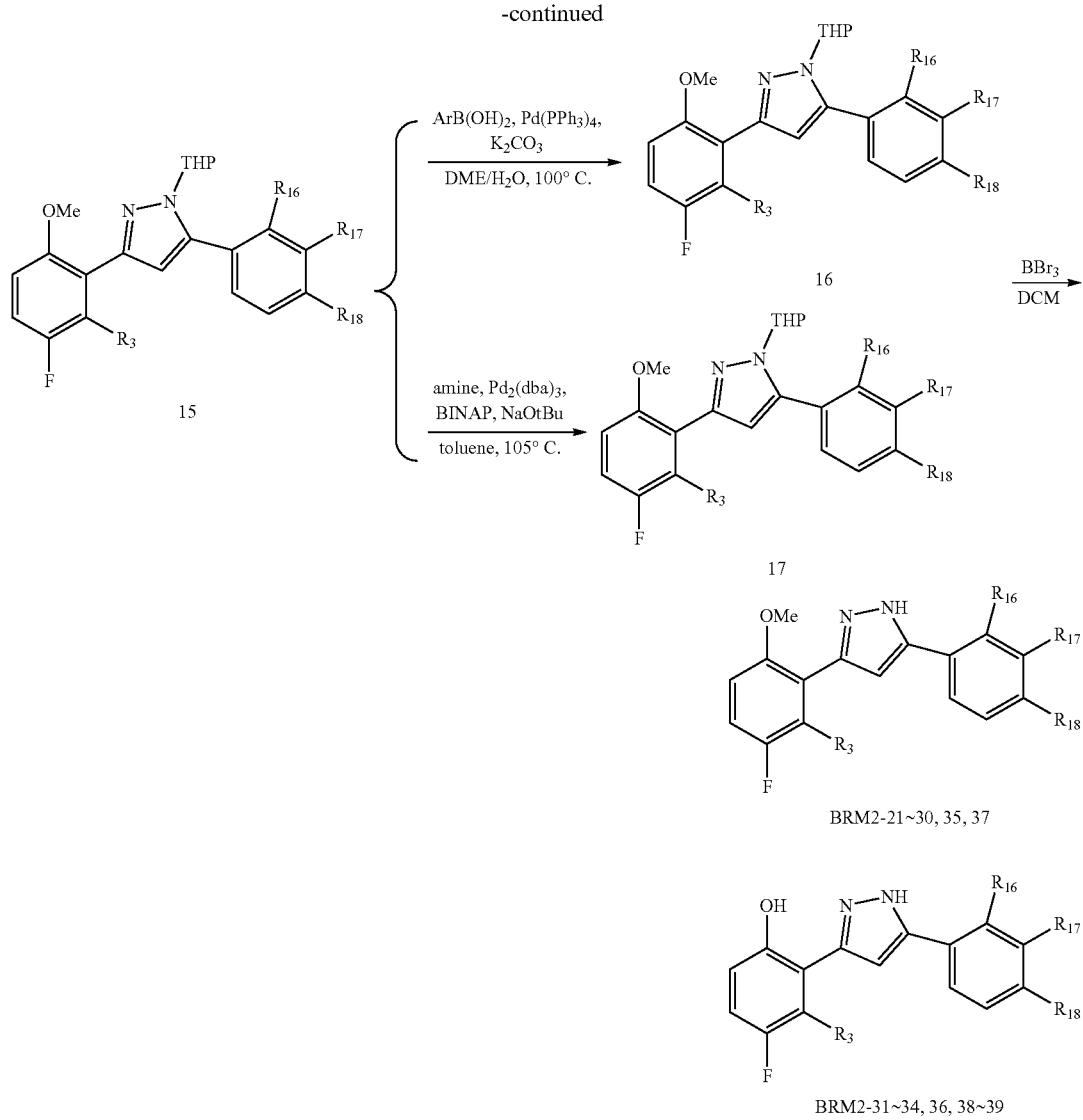

BRM2-21~30, 35, 37

BRM2-31~34, 36, 38~39

The intermediate 12 (1 eq.) and pyridinium toluene-4-sulphonate (PPTS, 0.1 eq.) are dissolved in dichloromethane, and then added with 3,4-dihydro-2H-pyran (DHP, 3 eq.) to produce a mixture, and the mixture is reacted at room temperature for 24 h. After the reaction is completed, the organic phase is removed by rotary evaporation under reduced pressure to produce a crude product, and the crude product is separated by column chromatography with neutral aluminum oxide, so as to obtain an intermediate 15.

A synthesis method of aromatic ring derivatives of pyrazole ring compounds is as follows: the intermediate 15 (1 eq.) is dissolved in a mixed liquor of ethylene glycol dimethyl ether and water (DME:H$_2$O=4:1), and added with K$_2$CO$_3$ (2.5 eq.), Pd(PPh$_3$)$_4$ (0.1 eq.), and an arylboronic acid compound (1.2 eq.). After nitrogen protection, heating is carried out to 100° C., reaction is carried out at 100° C. for 24 h. After the reaction is completed, the organic solvent is removed by rotary evaporation under reduced pressure, and then extraction is carried out twice with ethyl acetate. The organic phase is dried and purified by silica-gel column chromatography to obtain an intermediate 16. The intermediate 16 is dissolved in dichloromethane, and added with BBr$_3$ (10 eq.) at −78° C. Then reaction is carried out at room temperature for 24 h. After the reaction is completed, the organic phase is dried by rotary evaporation to produce a crude product. The crude product is dissolved in ethyl acetate, and washed once with water and once with saline, the organic phase is dried, and then purified by silica-gel column chromatography to obtain the compounds BRM2-21 to BRM2-30, BRM2-35, BRM2-37.

A synthesis method of amine derivatives of pyrazole ring compounds is as follows: the intermediate 15 (1 eq.) and an amino compound (2 eq.) are dissolved in toluene, and then added with Pd$_2$(dba)$_3$ (0.05 eq.), 1,1'-binaphthalene-2,2'-bisdiphenylphosphine (BINAP, 0.1 eq.), and NaOtBu (2.5 eq.). After protected by nitrogen displacement, a reaction flask is heated to react at 105° C. for 24 h. After the reaction is completed, extraction is carried out with ethyl acetate. The organic phase is washed once with water and once with saline, dried, and then purified by silica-gel column chromatography to obtain an intermediate 17. The intermediate 17 is dissolved in dichloromethane, and added with BBr$_3$ (10 eq.) at −78° C. Then reaction is carried out at room temperature for 24 h. After the reaction is completed, the organic phase is dried by rotary evaporation to produce a crude product. The crude product is dissolved in ethyl acetate, washed once with water and once with saline, the organic phase is dried, and then purified by silica-gel column chromatography to obtain the compounds BRM2-31 to BRM2-34, BRM2-36, BRM2-38 to BRM2-39.

Example 4

Synthesis of Bis-N Heterocyclic Substituted Pyrazole Compounds (BRM2-40 to BRM2-42)

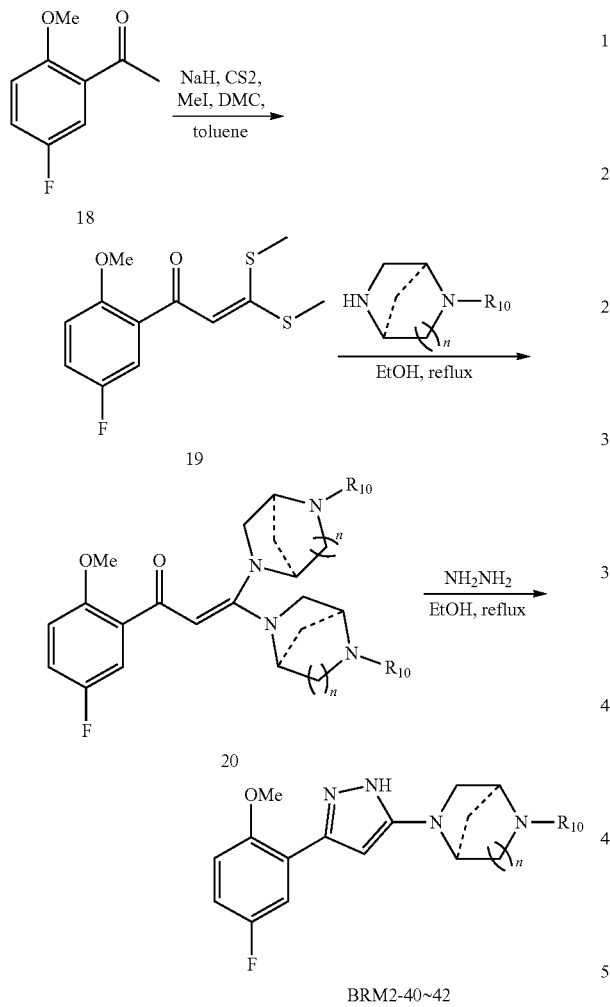

BRM2-40~42 duced after purification through silica-gel column chromatography. The compound 20 is dissolved in absolute ethanol, and added with 98% hydrazine hydrate (2 eq.) to produce a mixture, and the mixture is heated to be subjected to reflux for 12 h to produce a product. After reaction is completed, the product is purified by silica-gel column chromatography to obtain the compounds BRM2-40 to BRM2-42.

Example 5

Synthesis of p-Amide Aryl Substituted Pyrazole Skeleton Compounds (BRM2-96 to BRM2-128)

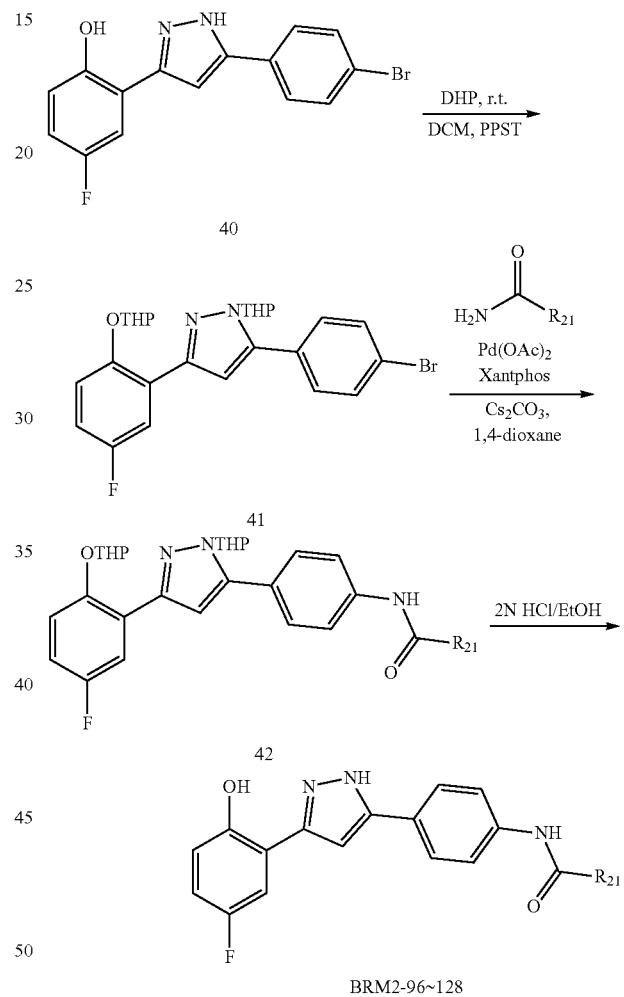

BRM2-96~128

A compound 18 (1 eq.) is dissolved in anhydrous toluene, and added with carbon disulfide (1.6 eq.) and methyl iodide (3.5 eq.). A reactor is placed in ice bath, slowly added with NaH (2.2 eq.), and then slowly added dropwise with N,N-dimethylacetamide (2.2 eq.). After the addition, the reactor is raised to room temperature for reaction for two days, and after the reaction is completed, the reaction is quenched by adding water. The organic phase is washed once with water and once with saline, dried, and purified by silica-gel column chromatography to obtain a compound 19. The compound 19 is dissolved in ethanol, and added with an amine compound R1 (2.2 eq.) to produce a product, and the product is heated to be subjected to reflux under stirring for 24 h. After reaction is completed, a compound 20 is pro- An intermediate 40 (1.0 eq.), DHP (3.0 eq.) and PPST (0.2 eq.) are dissolved in dichloromethane to produce a mixture, the mixture is reacted at r.t. for 12 h to produce a product, and then the product is separated through a neutral aluminum oxide chromatographic column to obtain an intermediate 41. The intermediate 41 (1.0 eq.), amide (1.2 eq.), Pd(OAc)$_2$ (0.02 eq.), Xantphos (0.03 eq.) and Cs$_2$CO$_3$ (1.4 eq.) are dissolved in 1,4-dioxane to produce a mixture, the mixture is reacted at 100° C. for 12 h to produce a product, and then the product is separated through a neutral aluminum oxide chromatographic column to obtain an intermediate 42. The intermediate 42 is dissolved in ethanol, added with 2N HCl in ethanol, extracted with ethyl acetate and added with saturated sodium bicarbonate to produce a crude product. The crude product is dried, and then purified by silica-gel column chromatography to obtain the compounds BRM2-96 to BRM2-128.

Example 6

Synthesis of Pyrazole Amide Compounds (BRM2-129 to BRM2-159)

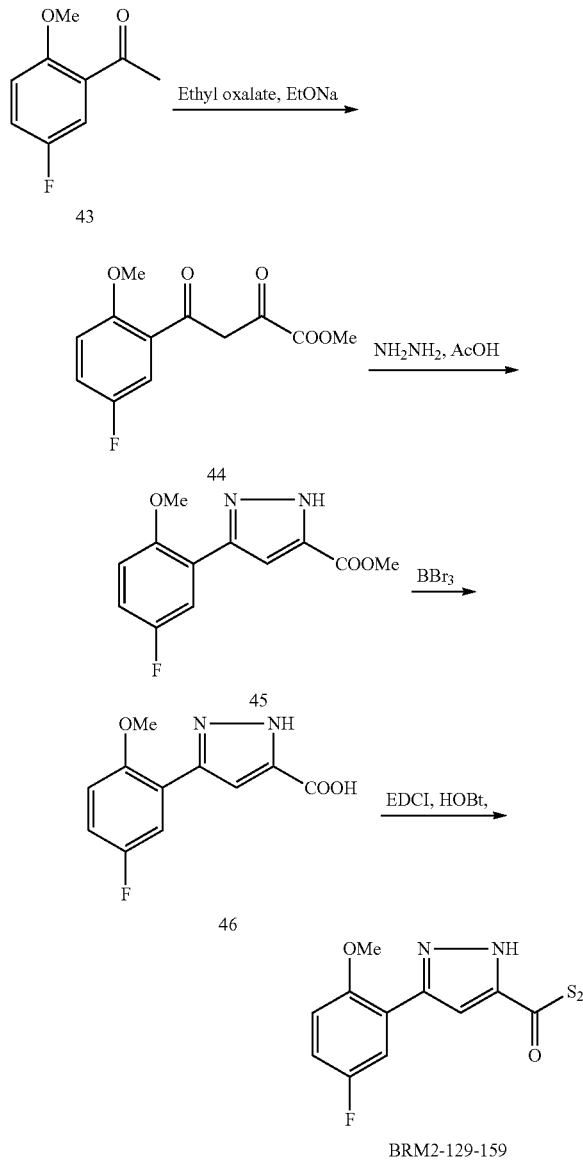

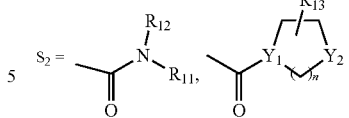

A compound 43 (1 eq.) is added dropwise into EtONa (2.3 eq.) and stirred at room temperature for 1 h, and then slowly added dropwise with diethyl oxalate to produce a mixture, the mixture is heated is to be subjected to for reflux for 4 h, and cooled to room temperature after the reaction is completed, and then glacial acetic acid (4 eq.) is added to generate a large amount of white solids. The white solids are filtered, and then respectively washed with a small amount of water, ethanol, and ether to obtain a product (intermediate) 44. The intermediate 44 is dissolved in acetic acid, then slowly added dropwise with hydrazine hydrate (1.2 eq.) in ice bath, and reacted overnight at room temperature to produce a reaction product. After the reaction is completed, the reaction product is filtered, and recrystallized in ethanol to obtain an intermediate 45. The intermediate 45 is dissolved in anhydrous dichloromethane, and added with BBr$_3$ (6 eq.) at −78° C., and after 1 h, reaction is carried out overnight at room temperature. After the reaction is completed, the reaction is quenched by slowly adding water. The organic phase is removed with a rotary evaporator to produce a reaction solution. The pH value of the reaction solution is adjusted to 5. The product is extracted with ethyl acetate, dried, and subjected to rotary evaporation under reduced pressure to remove the organic solvent, so as to obtain an intermediate 46. The intermediate 46, EDCI (1.2 eq.) and HOBt (1.2 eq.) are added into anhydrous DMF, stirred for half an hour and then added with a corresponding amine compound R to produce a mixture, and the mixture is reacted for 12 h to. After the reaction is completed, with ethyl acetate is added, and the organic phase is washed for three times with a saturated ammonium chloride solution and once with a saturated sodium chloride solution, dried over anhydrous magnesium sulfate, and then the dried organic phase is purified by silica-gel column chromatography to obtain the final products BRM2-129 to BRM2-159.

Example 7

Synthesis of 5-Substituted Aminopyrazole Compounds (BRM2-160 to BRM2-174)

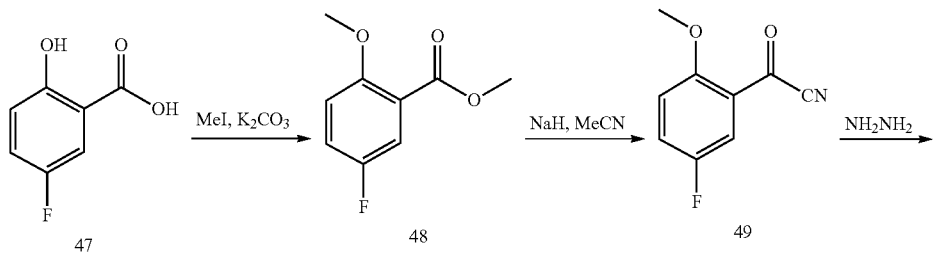

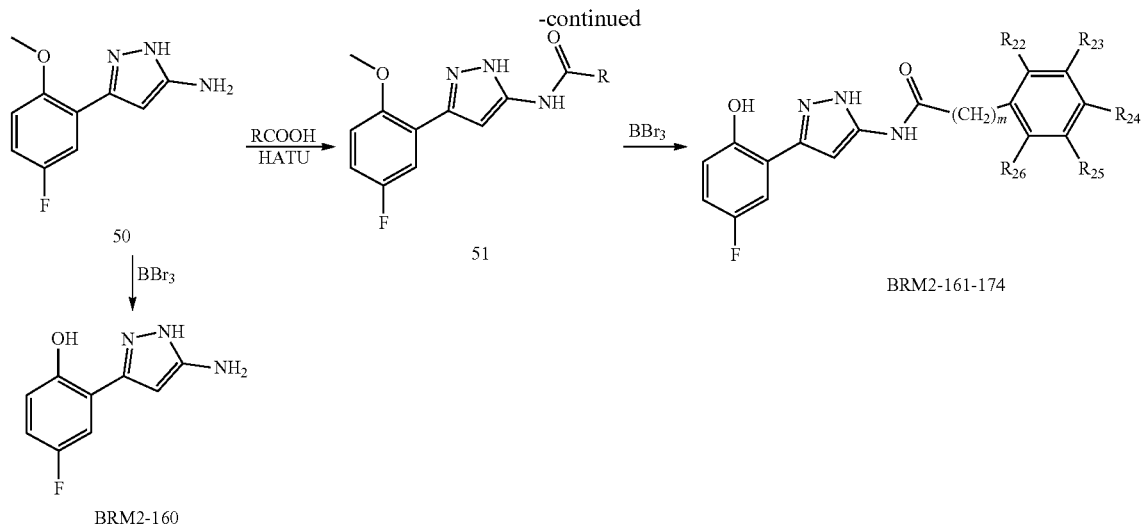

A compound 47 (1.0 eq.), methyl iodide (3.0 eq.), and potassium carbonate (3.0 eq.) are dissolved in a certain amount of acetone solution, and reacted under stirring at 40° C. for 12 h. The solvent is dried by rotary evaporation, and extraction is carried out through ethyl acetate and added with saturated sodium bicarbonate to produce a crude product. The crude product is dried, and purified by silica-gel column chromatography to obtain an intermediate 48. The intermediate 48 (1.0 eq.) is dissolved in ultra-dry toluene, added with acetonitrile (3.0 eq.), then added with sodium hydride (3.0 eq.), and added with a buffer balloon to a produce a mixture, and the mixture is heated to react at 90° C. for 3 h. The solvent is dried by rotary evaporation, extraction is carried out with ethyl acetate and saturated sodium bicarbonate is added to produce a crude product. The crude product is dried, and purified by silica-gel column chromatography to obtain an intermediate 49. The intermediate 49 (1.0 eq.) and hydrazine monohydrate (1.2 eq.) are dissolved in ethanol together, and then added with glacial acetic acid (6.0 eq.) to produce a mixture, and the mixture is heated to react at 50° C. for 3 h. The solvent is dried by rotary evaporation, extraction is carried out with ethyl acetate and saturated sodium bicarbonate is added to produce a crude product. The crude product is dried, and purified by silica-gel column chromatography to obtain an intermediate 50. The intermediate 50 and different types of carboxylic acids are added into a solvent of DMF in one to one equivalent, added with HATU (1.5 eq.) and DIPEA (1.5 eq.) to produce a mixture, the mixture is reacted at 70° C. for 12 h, and extraction is carried out with ethyl acetate to produce a crude product. The crude product is dried, and purified by silica-gel column chromatography to obtain an intermediate 51. The intermediate 51 or 50 (1 eq.) is dissolved in ultra-dry DCM, and added with boron tribromide (8 eq.) at 0° C. to produce a mixture, and the mixture is reacted under stirring at room temperature for 12 h. The solvent is dried by rotary evaporation, extraction is carried out with ethyl acetate and saturated sodium bicarbonate is added to produce a crude product. The crude product is dried, and purified by silica-gel column chromatography to obtain the final products BRM2-160 to BRM2-174.

Example 8

Spectral Data of Compounds Prepared in Examples 1-7

In the example, corresponding synthetic identification spectral data for the compounds prepared according to the general synthesis method described above are as follows:

BRM2-1: $^1$H NMR (400 MHz, CDCl$_3$) δ 6.97-6.82 (m, 1H), 6.48 (dd, J=17.9, 11.6 Hz, 1H), 6.31 (dd, J=8.6, 4.0 Hz, 1H), 5.22 (dd, J=38.2, 14.7 Hz, 2H), 2.74 (t, J=7.6 Hz, 2H), 1.73 (dd, J=15.1, 7.5 Hz, 2H), 1.03 (t, J=7.3 Hz, 3H). Mass spectrum (ESI, m/z): C14H16FN3O, [M+H]$^+$: 262.13.

BRM2-2: $^1$H NMR (400 MHz, CDCl$_3$) δ 7.34 (dt, J=15.2, 7.6 Hz, 4H), 7.25 (t, J=6.8 Hz, 1H), 6.96 (t, J=9.7 Hz, 1H), 6.86 (d, J=16.6 Hz, 1H), 6.65 (d, J=16.6 Hz, 1H), 6.34 (d, J=5.2 Hz, 1H), 2.88 (t, J=7.6 Hz, 2H), 1.88-1.80 (m, 2H), 1.08 (t, J=7.3 Hz, 3H). Mass spectrum (ESI, m/z): C20H20FN3O, [M+H]$^+$: 338.16.

BRM2-3: $^1$H NMR (400 MHz, CDCl$_3$) δ 6.97-6.82 (m, 1H), 6.27 (dd, J=8.8, 4.1 Hz, 1H), 6.07 (d, J=16.1 Hz, 1H), 5.78-5.62 (m, 1H), 2.68-2.48 (m, 2H), 2.06 (q, J=7.1 Hz, 2H), 1.70-1.51 (m, 2H), 1.37 (dd, J=14.6, 7.3 Hz, 2H), 0.93 (t, J=7.3 Hz, 3H), 0.87 (t, J=7.3 Hz, 4H). Mass spectrum (ESI, m/z): C17H20FN3O, [M+H]$^+$: 304.17.

BRM2-4: $^1$H NMR (400 MHz, MeOD) δ 7.71 (d, J=6.8 Hz, 2H), 7.59 (d, J=6.8 Hz, 2H), 7.01 (s, 1H), 6.82 (t, J=8.9 Hz, 1H), 6.20 (s, 1H). Mass spectrum (ESI, m/z): C15H10BrFN2O, [M+H]$^+$: 333.00.

BRM2-5: $^1$H NMR (400 MHz, MeOD) δ 7.69 (d, J=8.2 Hz, 2H), 7.56-7.41 (m, 3H), 7.05 (s, 1H), 6.97-6.85 (m, 2H), 1.35 (s, 9H). Mass spectrum (ESI, m/z): C19H19FN2O, [M+H]$^+$: 311.15.

BRM2-6: $^1$H NMR (400 MHz, MeOD) δ 7.67 (d, J=7.9 Hz, 2H), 7.50-7.39 (m, 1H), 7.28 (d, J=8.0 Hz, 2H), 7.02 (s, 1H), 7.00-6.77 (m, 2H), 2.67 (q, J=7.6 Hz, 2H), 1.25 (t, J=7.6 Hz, 3H). Mass spectrum (ESI, m/z): C17H15FN2O, [M+H]$^+$: 283.12.

BRM2-7: $^1$H NMR (400 MHz, MeOD) δ 7.43 (d, J=8.3 Hz, 2H), 7.30 (s, 3H), 6.90 (d, J=5.7 Hz, 2H), 6.83 (s, 1H), 2.42 (s, 3H). Mass spectrum (ESI, m/z): C16H13FN2O, [M+H]$^+$: 269.10.

BRM2-8: $^1$H NMR (400 MHz, MeOD) δ 7.66-7.48 (m, 2H), 7.48-7.38 (m, 1H), 7.32 (t, J=7.6 Hz, 1H), 7.18 (d, J=7.5 Hz, 1H), 7.04 (s, 1H), 6.89 (d, J=5.5 Hz, 2H), 2.39 (s, 3H). Mass spectrum (ESI, m/z): C16H12FN2O, [M+H]$^+$: 269.10.

BRM2-9: ¹H NMR (400 MHz, MeOD) δ 7.42 (d, J=10.3 Hz, 1H), 7.26 (s, 1H), 7.15 (dd, J=26.4, 7.6 Hz, 2H), 6.90 (d, J=5.3 Hz, 2H), 6.82 (s, 1H), 2.35 (d, J=14.3 Hz, 6H). Mass spectrum (ESI, m/z): C17H15FN2O, [M+H]⁺: 283.12.

BRM2-10: ¹H NMR (400 MHz, MeOD) δ 7.44 (d, J=9.7 Hz, 1H), 7.38 (s, 2H), 7.03 (d, J=4.8 Hz, 2H), 6.89 (d, J=4.1 Hz, 2H), 2.36 (s, 6H). Mass spectrum (ESI, m/z): C17H15FN2O, [M+H]⁺:283.12.

BRM2-11: ¹H NMR (400 MHz, CDCl₃) δ 7.35-7.30 (m, 1H), 7.26 (s, 2H), 7.10 (s, 1H), 7.05-6.93 (m, 2H), 6.87 (s, 1H), 2.42 (s, 6H). Mass spectrum (ESI, m/z): C17H15FN2O, [M+H]⁺: 283.12.

BRM2-12: 1H NMR (400 MHz, DMSO) δ 13.44 (d, J=188.0 Hz, 1H), 10.52 (s, 1H), 7.93 (s, 1H), 7.64 (s, 1H), 7.38 (d, J=36.3 Hz, 4H), 7.04 (t, J=8.3 Hz, 1H), 6.97 (d, J=4.8 Hz, 1H). Mass spectrum (ESI, m/z): C15H10F2N2O, [M+H]⁺: 273.08.

BRM2-13: ¹H NMR (400 MHz, CDCl₃) δ 7.46 (d, J=7.8 Hz, 2H), 7.07 (d, J=7.9 Hz, 2H), 6.93-6.85 (m, 1H), 6.61 (s, 1H), 6.37 (d, J=4.5 Hz, 1H), 3.12-3.04 (m, 2H), 3.02-2.94 (m, 2H). Mass spectrum (ESI, m/z): C15H10ClFN2O, [M+H]⁺: 289.05.

BRM2-14: ¹H NMR (400 MHz, MeOD) δ 12.62 (s, 1H), 7.68-7.66 (m, 2H), 7.45 (m, 1H), 7.35-7.30 (m, 2H), 7.05-6.95 (m, 2H), 6.81 (m, 1H). Mass spectrum (ESI, m/z): C15H10BrFN2O, [M+H]⁺: 333.00.

BRM2-15: ¹H NMR (400 MHz, MeOD) δ 7.47 (d, J=6.6 Hz, 1H), 7.35-7.19 (m, 3H), 6.90-6.74 (m, 2H), 6.24 (dd, J=8.8, 4.2 Hz, 1H), 2.44 (s, 3H). Mass spectrum (ESI, m/z): C15H11BrFN3O, [M+H]⁺: 348.01.

BRM2-16: ¹H NMR (400 MHz, MeOD) δ 7.42 (d, J=7.5 Hz, 1H), 7.34 (d, J=4.0 Hz, 2H), 7.29-7.19 (m, 1H), 6.95-6.81 (m, 2H), 6.22 (dd, J=8.8, 4.2 Hz, 1H), 2.80 (q, J=7.6 Hz, 2H), 1.17 (t, J=7.5 Hz, 3H). Mass spectrum (ESI, m/z): C16H13BrFN3O, [M+H]⁺: 362.02.

BRM2-17: ¹H NMR (400 MHz, CDCl₃) δ 7.50-7.42 (m, 2H), 7.35-7.24 (m, 2H), 6.93-6.86 (m, 2H), 6.36 (s, 1H), 3.32-3.02 (m, 1H), 1.23 (d, J=6.5 Hz, 6H). Mass spectrum (ESI, m/z): C15H12BrN3O, [M+H]⁺: 330.02.

BRM2-18: ¹H NMR (400 MHz, DMSO) δ 13.44 (d, J=188.0 Hz, 1H), 10.52 (s, 1H), 7.93 (s, 1H), 7.64 (s, 1H), 7.38 (d, J=36.3 Hz, 4H), 7.04 (t, J=8.3 Hz, 1H), 6.97 (d, J=4.8 Hz, 1H). Mass spectrum (ESI, m/z): C16H14FN3O, [M+H]⁺: 284.11.

BRM2-19: ¹H NMR (400 MHz, Acetone) δ 12.90 (s, 1H), 10.72 (s, 1H), 7.78 (dd, J=5.9, 3.4 Hz, 1H), 7.62 (ddd, J=12.6, 7.4, 2.8 Hz, 2H), 7.55-7.47 (m, 2H), 7.32 (s, 1H), 7.06-6.93 (m, 2H). Mass spectrum (ESI, m/z): C17H16FN3O, [M+H]⁺: 298.13.

BRM2-20: ¹H NMR (400 MHz, CDCl₃) δ 7.85 (s, 1H), 7.61 (d, J=7.7 Hz, 1H), 7.48 (d, J=7.9 Hz, 1H), 7.29 (dd, J=13.4, 6.5 Hz, 2H), 6.90 (d, J=5.6 Hz, 2H), 6.83 (s, 1H). Mass spectrum (ESI, m/z): C18H18FN3O, [M+H]⁺: 312.14.

BRM2-21: ¹H NMR (400 MHz, MeOD) δ 7.86 (d, J=7.0 Hz, 2H), 7.68 (dd, J=19.1, 7.3 Hz, 4H), 7.45 (t, J=6.8 Hz, 2H), 7.35 (d, J=6.8 Hz, 2H), 7.07 (s, 1H), 6.82 (d, J=9.5 Hz, 1H), 6.22 (d, J=4.9 Hz, 1H). Mass spectrum (ESI, m/z): C21H16FN3O, [M+H]⁺: 346.13.

BRM2-22: ¹H NMR (400 MHz, MeOD) δ 7.85 (d, J=8.0 Hz, 2H), 7.67 (dd, J=7.9, 4.4 Hz, 4H), 7.18 (t, J=8.6 Hz, 2H), 7.06 (s, 1H), 6.93-6.70 (m, 2H), 6.21 (dd, J=8.8, 4.1 Hz, 1H). Mass spectrum (ESI, m/z): C21H15F2N3O, [M+H]⁺: 364.12.

BRM2-23: ¹H NMR (400 MHz, CDCl₃) δ 12.62 (s, 1H), 10.10 (br, 1H), 8.30 (dd, 2H), 7.85-7.70 (m, 5H), 7.35-7.27 (m, 2H), 7.03-6.99 (m, 2H), 6.45 (d, 1H). Mass spectrum (ESI, m/z): C23H16FN3O, [M+H]⁺: 370.13.

BRM2-24: ¹H NMR (400 MHz, CDCl₃) δ 7.82-7.46 (m, 7H), 7.40-7.20 (m, 2H), 6.97-6.84 (m, 3H). Mass spectrum (ESI, m/z): C21H14BrFN2O, [M+H]⁺: 409.03.

BRM2-25: ¹H NMR (400 MHz, MeOD) δ 7.87 (d, J=7.9 Hz, 2H), 7.73 (d, J=8.0 Hz, 2H), 7.67 (d, J=8.2 Hz, 2H), 7.47 (d, J=8.2 Hz, 3H), 7.16 (s, 1H), 6.93 (d, J=4.2 Hz, 2H). Mass spectrum (ESI, m/z): C21H14ClFN2O, [M+H]⁺: 365.08.

BRM2-26: ¹H NMR (400 MHz, DMSO) δ 13.81 (s, 1H), 10.68 (s, 1H), 8.98 (s, 1H), 8.59 (s, 1H), 8.15 (d, J=6.4 Hz, 1H), 7.95 (t, J=15.6 Hz, 4H), 7.64 (s, 1H), 7.60-7.36 (m, 2H), 7.10-6.88 (m, 2H). Mass spectrum (ESI, m/z): C20H14FN3O, [M+H]⁺: 332.11.

BRM2-27: ¹H NMR (400 MHz, MeOD) δ 7.84 (d, J=7.8 Hz, 2H), 7.47 (d, J=9.9 Hz, 1H), 7.20 (d, J=7.8 Hz, 2H), 7.15-7.04 (m, 4H), 6.92 (d, J=5.7 Hz, 2H), 2.02 (s, 6H). Mass spectrum (ESI, m/z): C23H19FN2O, [M+H]⁺: 359.15.

BRM2-28: ¹H NMR (400 MHz, MeOD) δ 7.81 (d, J=7.5 Hz, 2H), 7.66 (d, J=7.8 Hz, 2H), 7.46 (d, J=9.0 Hz, 1H), 7.24 (s, 2H), 7.09 (s, 1H), 7.00 (s, 1H), 6.92 (d, J=5.2 Hz, 2H), 2.36 (s, 6H). Mass spectrum (ESI, m/z): C23H19FN2O, [M+H]⁺: 359.15.

BRM2-29: ¹H NMR (400 MHz, MeOD) δ 7.80 (d, J=8.0 Hz, 2H), 7.64 (d, J=8.1 Hz, 2H), 7.52-7.42 (m, 1H), 7.16-7.07 (m, 2H), 7.04 (dd, J=8.2, 2.0 Hz, 1H), 6.96-6.90 (m, 2H), 6.88 (d, J=8.2 Hz, 1H). Mass spectrum (ESI, m/z): C21H15FN2O3, [M+H]⁺: 363.11.

BRM2-30: ¹H NMR (400 MHz, DMSO) δ 8.10-7.95 (m, 6H), 7.90 (d, J=8.1 Hz, 2H), 7.61 (dd, J=9.8, 2.5 Hz, 1H), 7.41 (s, 1H), 7.02 (td, J=8.5, 2.6 Hz, 1H), 6.95 (dd, J=8.8, 5.0 Hz, 1H), 3.28 (s, 3H). Mass spectrum (ESI, m/z): C22H17FN2O3S, [M+H]⁺: 409.09.

BRM2-31: ¹H NMR (400 MHz, Acetone) δ 13.08 (s, 1H), 10.80 (s, 1H), 8.21 (s, 1H), 7.89 (d, J=7.4 Hz, 1H), 7.75 (dd, J=19.1, 7.7 Hz, 3H), 7.61 (t, J=8.4 Hz, 2H), 7.55-7.36 (m, 4H), 7.00 (dd, J=13.2, 4.0 Hz, 2H). Mass spectrum (ESI, m/z): C21H15FN2O, [M+H]⁺: 331.12

BRM2-32: ¹H NMR (400 MHz, Acetone) δ 13.05 (s, 1H), 10.80 (s, 1H), 8.21 (s, 1H), 7.90 (d, J=7.7 Hz, 1H), 7.77 (dd, J=15.3, 7.6 Hz, 3H), 7.67-7.56 (m, 2H), 7.53 (t, J=7.6 Hz, 2H), 7.48 (s, 1H), 7.43 (t, J=7.3 Hz, 1H), 7.05-6.91 (m, 2H). Mass spectrum (ESI, m/z): C21H15FN2O, [M+H]⁺: 331.12.

BRM2-33: ¹H NMR (400 MHz, Acetone) δ 12.91 (s, 1H), 10.84 (s, 1H), 7.57 (d, J=9.5 Hz, 1H), 7.47 (s, 1H), 7.33 (d, J=8.0 Hz, 2H), 7.27 (d, J=7.3 Hz, 1H), 7.07-6.87 (m, 3H), 3.26 (d, J=4.7 Hz, 4H), 1.65 (dd, J=34.6, 4.1 Hz, 6H). Mass spectrum (ESI, m/z): C20H20FN3O, [M+H]⁺: 338.16.

BRM2-34: ¹H NMR (400 MHz, MeOD) δ 7.50-7.43 (m, 1H), 7.36 (s, 1H), 7.31 (t, J=7.8 Hz, 1H), 7.26 (d, J=7.6 Hz, 1H), 7.09 (d, J=5.1 Hz, 1H), 6.98-6.89 (m, 3H), 3.33-3.25 (m, 4H), 2.81-2.70 (m, 4H), 2.45 (s, 3H). Mass spectrum (ESI, m/z): C20H21FN4O, [M+H]⁺: 353.17.

BRM2-35:1H NMR (400 MHz, Acetone) δ 12.91 (s, 1H), 10.86 (s, 1H), 7.57 (dd, J=9.6, 2.9 Hz, 1H), 7.49-7.44 (m, 1H), 7.36-7.29 (m, 2H), 7.28-7.23 (m, 1H), 7.04-6.92 (m, 3H), 3.31-3.21 (m, 4H), 1.75-1.64 (m, 4H), 1.60 (ddd, J=11.5, 4.7, 2.2 Hz, 2H). Mass spectrum (ESI, m/z): C20H20FN3O, [M+H]⁺: 338.16.

BRM2-36: 1H NMR (400 MHz, MeOD) δ 7.51-7.45 (m, 1H), 7.36 (dd, J=15.8, 7.9 Hz, 2H), 7.27 (d, J=7.7 Hz, 1H), 7.11 (s, 1H), 7.01 (dd, J=8.2, 1.7 Hz, 1H), 6.95-6.90 (m, 2H), 3.32-3.26 (m, 4H), 2.72-2.64 (m, 4H), 2.39 (s, 3H). Mass spectrum (ESI, m/z): C20H21FN4O, [M+H]⁺: 353.17.

BRM2-37: ¹H NMR (400 MHz, MeOD) δ 7.60 (d, J=8.4 Hz, 2H), 7.49-7.38 (m, 1H), 6.91 (t, J=5.0 Hz, 3H), 6.81 (d, J=8.5 Hz, 2H), 3.70-3.58 (m, 2H), 3.53 (t, J=6.2 Hz, 2H), 2.99-2.86 (m, 2H), 2.84-2.73 (m, 2H), 2.51 (s, 3H), 2.15-2.01 (m, 2H). Mass spectrum (ESI, m/z): C21H23FN4O, [M+H]+: 367.19.

BRM2-38: $^1$H NMR (400 MHz, Acetone) δ 12.76 (s, 1H), 10.92 (s, 1H), 7.74 (d, J=8.2 Hz, 2H), 7.54 (d, J=9.6 Hz, 1H), 7.19 (s, 1H), 7.08 (d, J=8.2 Hz, 2H), 6.96 (dt, J=13.5, 8.5 Hz, 2H), 3.31 (s, 4H), 2.56 (s, 4H), 2.31 (s, 3H). Mass spectrum (ESI, m/z): C20H21FN4O, [M+H]+: 353.17.

BRM2-39: $^1$H NMR (400 MHz, Acetone) δ 12.72 (s, 1H), 10.93 (s, 1H), 7.72 (d, J=8.6 Hz, 2H), 7.54 (dd, J=9.6, 2.7 Hz, 1H), 7.17 (s, 1H), 7.07 (d, J=8.2 Hz, 2H), 7.02-6.89 (m, 2H), 3.39-3.21 (m, 4H), 1.66 (dd, J=25.3, 4.2 Hz, 6H). Mass spectrum (ESI, m/z): C20H20FN3O, [M+H]+: 338.16.

BRM2-40: $^1$H NMR (400 MHz, DMSO) δ 12.25 (s, 1H), 11.30 (s, 1H), 8.06 (d, J=3.5 Hz, 1H), 7.55-7.35 (m, 2H), 6.96 (td, J=8.5, 3.0 Hz, 1H), 6.90-6.83 (m, 1H), 6.66 (d, J=8.6 Hz, 1H), 6.57-6.43 (m, 1H), 6.09 (s, 1H), 3.86-3.80 (m, 2H), 3.55 (d, J=4.8 Hz, 4H), 3.38-3.32 (m, 2H), 2.06-1.88 (m, 2H). Mass spectrum (ESI, m/z): C19H20FN5O, [M+H]+: 353.17.

BRM2-41: $^1$H NMR (400 MHz, Acetone) δ 11.62 (s, 1H), 11.10 (s, 1H), 8.06 (d, J=4.0 Hz, 1H), 7.55-7.38 (m, 1H), 7.34 (dd, J=9.7, 3.0 Hz, 1H), 6.99-6.78 (m, 2H), 6.54 (dd, J=6.8, 5.2 Hz, 1H), 6.46 (d, J=8.5 Hz, 1H), 6.01 (s, 1H), 4.98 (s, 1H), 4.58 (s, 1H), 3.70 (dd, J=8.7, 1.6 Hz, 1H), 3.63-3.48 (m, 2H), 3.31 (d, J=8.7 Hz, 1H), 2.13 (q, J=9.6 Hz, 2H). Mass spectrum (ESI, m/z): C19H18FN5O, [M+H]+: 352.15.

BRM2-42: $^1$H NMR (400 MHz, Acetone) δ 11.89 (s, 1H), 11.07 (s, 1H), 7.41 (dd, J=9.7, 3.0 Hz, 1H), 7.32-7.21 (m, 2H), 7.05 (d, J=8.0 Hz, 2H), 6.99-6.80 (m, 3H), 6.27 (s, 1H), 3.50-3.40 (m, 4H), 3.40-3.30 (m, 4H). Mass spectrum (ESI, m/z): C19H19FN4O, [M+H]+: 339.15.

BRM2-96: $^1$H NMR (400 MHz, CDCl$_3$) δ 8.97 (s, 1H), 7.91-7.76 (m, 4H), 7.76-7.45 (m, 3H), 7.46-7.30 (m, 2H), 7.21-7.06 (m, 2H), 6.95 (dd, J=15.0, 10.1 Hz, 1H), 4.94 (s, 1H). Mass spectrum (ESI, m/z): C22H15F2N3O2, [M+H]+: 392.11.

BRM2-97: $^1$H NMR (400 MHz, CDCl$_3$) δ 9.04 (s, 1H), 8.28-8.02 (m, 1H), 8.00-7.70 (m, 4H), 7.51 (tdd, J=14.9, 10.0, 3.1 Hz, 1H), 7.42-7.25 (m, 2H), 7.21-6.99 (m, 3H), 6.95 (dd, J=15.0, 10.1 Hz, 1H), 4.89 (s, 1H). Mass spectrum (ESI, m/z): C22H15F2N3O2, [M+H]+: 392.11.

BRM2-98: $^1$H NMR (400 MHz, CDCl$_3$) δ 9.17 (s, 1H), 8.01-7.76 (m, 6H), 7.76-7.53 (m, 2H), 7.35 (dd, J=16.0, 3.0 Hz, 1H), 7.31-7.04 (m, 2H), 6.95 (dd, J=15.0, 10.0 Hz, 1H), 4.97 (s, 1H). Mass spectrum (ESI, m/z): C22H15BrFN3O2, [M+H]+: 452.03.

BRM2-99: $^1$H NMR (400 MHz, CDCl$_3$) δ 9.19 (s, 1H), 8.25-8.04 (m, 2H), 7.98-7.66 (m, 4H), 7.52-7.27 (m, 3H), 7.22-7.06 (m, 2H), 6.95 (dd, J=15.0, 10.0 Hz, 1H), 4.97 (s, 1H). Mass spectrum (ESI, m/z): C22H15F2N3O2, [M+H]+: 392.11.

BRM2-100: $^1$H NMR (400 MHz, CDCl$_3$) δ 8.95 (s, 1H), 8.02-7.73 (m, 6H), 7.76-7.52 (m, 2H), 7.35 (dd, J=16.0, 2.9 Hz, 1H), 7.24-7.07 (m, 2H), 6.95 (dd, J=15.0, 10.1 Hz, 1H), 4.92 (s, 1H). Mass spectrum (ESI, m/z): C22H15FClN3O2, [M+H]+: 408.08.

BRM2-101: $^1$H NMR (400 MHz, CDCl$_3$) δ 9.17 (s, 1H), 8.01-7.59 (m, 4H), 7.43 (s, 4H), 7.35 (dd, J=16.0, 2.9 Hz, 1H), 7.25-7.04 (m, 2H), 6.95 (dd, J=15.0, 10.1 Hz, 1H), 4.93 (s, 1H). Mass spectrum (ESI, m/z): C22H15FClN3O2, [M+H]+: 408.08.

BRM2-102: $^1$H NMR (400 MHz, CDCl$_3$) δ 8.95 (s, 1H), 8.01-7.59 (m, 6H), 7.50-7.21 (m, 3H), 7.22-7.03 (m, 2H), 6.95 (dd, J=15.0, 10.1 Hz, 1H), 4.94 (s, 1H), 2.42 (s, 3H). Mass spectrum (ESI, m/z): C23H18FN3O2, [M+H]+: 388.14.

BRM2-103: $^1$H NMR (400 MHz, CDCl$_3$) δ 9.20 (s, 1H), 8.04-7.61 (m, 6H), 7.48-7.22 (m, 3H), 7.24-7.03 (m, 2H), 6.95 (dd, J=15.0, 10.0 Hz, 1H), 4.98 (s, 1H), 2.41 (s, 3H). Mass spectrum (ESI, m/z): C23H18FN3O2, [M+H]+: 388.14.

BRM2-104: $^1$H NMR (400 MHz, CDCl$_3$) δ 9.10 (s, 1H), 7.98-7.58 (m, 6H), 7.55-7.26 (m, 2H), 7.31-7.02 (m, 3H), 6.95 (dd, J=15.0, 10.0 Hz, 1H), 4.96 (s, 1H). Mass spectrum (ESI, m/z): C23H15F4N3O2, [M+H]+: 442.12.

BRM2-105: $^1$H NMR (400 MHz, CDCl$_3$) δ 9.58 (s, 1H), 8.07-7.67 (m, 4H), 7.59-7.41 (m, 1H), 7.38-7.22 (m, 2H), 7.18-7.04 (m, 3H), 6.95 (dd, J=15.0, 10.1 Hz, 1H). Mass spectrum (ESI, m/z): C22H14F3N3O2, [M+H]+: 410.10.

BRM2-106: $^1$H NMR (400 MHz, CDCl$_3$) δ 9.00 (s, 1H), 8.10-7.58 (m, 4H), 7.35 (dd, J=16.0, 2.9 Hz, 1H), 7.20-7.00 (m, 2H), 6.95 (dd, J=15.0, 10.1 Hz, 1H), 4.43 (s, 1H), 2.10-1.96 (m, 3H), 1.97-1.78 (m, 6H), 1.81-1.52 (m, 6H). Mass spectrum (ESI, m/z): C26H26FN3O2, [M+H]+: 432.20.

BRM2-107: $^1$H NMR (400 MHz, CDCl$_3$) δ 8.93 (s, 1H), 8.08-7.65 (m, 6H), 7.35 (dd, J=16.0, 2.9 Hz, 1H), 7.25-7.04 (m, 4H), 6.95 (dd, J=15.0, 10.1 Hz, 1H), 4.94 (s, 1H), 3.79 (s, 3H). Mass spectrum (ESI, m/z): C23H18FN3O2, [M+H]+: 404.13.

BRM2-108: $^1$H NMR (400 MHz, CDCl$_3$) δ 8.94 (s, 1H), 8.08-7.59 (m, 4H), 7.35 (dd, J=16.0, 2.9 Hz, 1H), 7.25-7.03 (m, 2H), 6.95 (dd, J=15.0, 10.1 Hz, 1H), 4.95 (s, 1H), 4.54-3.86 (m, 2H), 2.96-2.59 (m, 2H), 2.37 (p, J=15.6 Hz, 1H), 1.90-1.69 (m, 2H), 1.67-1.40 (m, 1H), 1.37-0.89 (m, 3H). Mass spectrum (ESI, m/z): C22H22FN3O2, [M+H]+: 380.17.

BRM2-109: $^1$H NMR (400 MHz, CDCl$_3$) δ 8.92 (s, 1H), 8.82 (d, J=15.0 Hz, 2H), 8.07-7.62 (m, 6H), 7.35 (dd, J=16.0, 2.9 Hz, 1H), 7.35 (dd, J=16.0, 2.9 Hz, 1H), 7.17-7.00 (m, 2H), 6.95 (dd, J=15.0, 10.1 Hz, 1H), 4.57 (s, 1H). Mass spectrum (ESI, m/z): C21H15FN4O2, [M+H]+: 375.12.

BRM2-110: $^1$H NMR (400 MHz, CDCl$_3$) δ 8.93 (s, 1H), 8.03-7.72 (m, 6H), 7.68-7.46 (m, 3H), 7.35 (dd, J=16.0, 2.9 Hz, 1H), 7.27 (s, 1H), 7.22-7.05 (m, 1H), 6.95 (dd, J=15.0, 10.1 Hz, 1H). Mass spectrum (ESI, m/z): C22H16FN3O2, [M+H]+: 374.12.

BRM2-111: $^1$H NMR (400 MHz, CDCl$_3$) δ 9.15-8.80 (m, 2H), 8.09 (dd, J=15.0, 3.0 Hz, 1H), 7.97-7.65 (m, 4H), 7.55-7.27 (m, 2H), 7.28-7.06 (m, 2H), 6.95 (dd, J=15.0, 10.1 Hz, 1H), 4.94 (s, 1H), 2.55 (s, 3H) Mass spectrum (ESI, m/z): C22H17FN4O2, [M+H]+: 389.13.

BRM2-112: $^1$H NMR (400 MHz, CDCl$_3$) δ 8.97-8.61 (m, 2H), 8.53-8.28 (m, 1H), 8.14-7.66 (m, 6H), 7.35 (dd, J=16.0, 2.9 Hz, 1H), 7.22-7.04 (m, 2H), 6.95 (dd, J=15.0, 10.1 Hz, 1H), 4.92 (s, 1H). Mass spectrum (ESI, m/z): C21H15FN4O2, [M+H]+: 375.12.

BRM2-113: $^1$H NMR (400 MHz, CDCl$_3$) δ 9.79 (s, 1H), 7.79 (ddd, J=18.3, 9.0, 4.5 Hz, 5H), 7.50-7.27 (m, 2H), 7.25-7.01 (m, 3H), 6.95 (dd, J=7.4, 5.0 Hz, 1H), 4.96 (s, 1H), 3.87 (d, J=16.0 Hz, 6H). Mass spectrum (ESI, m/z): C24H20FN3O4, [M+H]+: 434.14.

BRM2-114: $^1$H NMR (400 MHz, CDCl$_3$) δ 9.00 (s, 1H), 8.00-7.62 (m, 5H), 7.49-7.20 (m, 3H), 7.17-7.04 (m, 2H), 6.95 (dd, J=15.0, 10.1 Hz, 1H), 4.93 (s, 1H). Mass spectrum (ESI, m/z): C22H14F3N3O2, [M+H]+: 410.10.

BRM2-115: $^1$H NMR (400 MHz, CDCl$_3$) δ 8.31 (s, 1H), 7.98-7.59 (m, 4H), 7.35 (dd, J=16.0, 2.9 Hz, 1H), 7.27-7.07 (m, 2H), 6.95 (dd, J=15.0, 10.1 Hz, 1H), 4.98 (s, 1H), 3.98-3.38 (m, 4H), 3.00 (tt, J=17.7, 15.8 Hz, 1H), 2.30-1.65 (m, 4H). Mass spectrum (ESI, m/z): C21H20FN3O3, [M+H]+: 382.15.

BRM2-116: ¹H NMR (400 MHz, CDCl₃) δ 8.79 (s, 1H), 8.24-7.65 (m, 4H), 7.49-7.21 (m, 2H), 7.20-7.07 (m, 1H), 6.95 (dd, J=15.0, 10.1 Hz, 1H), 2.48-1.88 (m, 1H), 1.21-0.30 (m, 4H). Mass spectrum (ESI, m/z): C19H16FN3O2, [M+H]⁺: 338.12.

BRM2-117: ¹H NMR (400 MHz, CDCl₃) δ 8.67 (s, 1H), 8.15-7.69 (m, 5H), 7.55-7.22 (m, 2H), 7.21-7.01 (m, 2H), 6.95 (dd, J=15.0, 10.1 Hz, 1H), 6.71 (t, J=15.0 Hz, 1H), 4.99 (s, 1H). Mass spectrum (ESI, m/z): C20H14FN3O3, [M+H]⁺: 364.10.

BRM2-118: ¹H NMR (400 MHz, CDCl₃) δ 8.98 (s, 1H), 8.02-7.74 (m, 5H), 7.67-7.44 (m, 1H), 7.35 (dd, J=16.0, 2.9 Hz, 1H), 7.33 (d, J=2.9 Hz, 1H), 7.24-6.69 (m, 5H), 4.94 (s, 1H), 4.05 (q, J=11.8 Hz, 2H), 1.34 (t, J=11.8 Hz, 3H). Mass spectrum (ESI, m/z): C24H20FN3O3, [M+H]⁺: 418.15.

BRM2-119: ¹H NMR (400 MHz, CDCl₃) δ 8.82 (s, 1H), 8.30 (dd, J=15.0, 3.0 Hz, 1H), 8.08-7.65 (m, 5H), 7.35 (dd, J=16.0, 2.9 Hz, 1H), 7.27-7.07 (m, 3H), 6.95 (dd, J=15.0, 10.1 Hz, 1H), 4.95 (s, 1H). Mass spectrum (ESI, m/z): C20H14FN3O2S, [M+H]⁺: 380.08.

BRM2-120: ¹H NMR (400 MHz, CDCl₃) δ 7.95-7.48 (m, 4H), 7.34 (dd, J=16.0, 2.9 Hz, 1H), 7.20-7.00 (m, 1H), 7.07-6.73 (m, 1H), 2.68-2.13 (m, 4H), 2.10-1.67 (m, 3H). Mass spectrum (ESI, m/z): C20H18FN3O2, [M+H]⁺: 352.14.

BRM2-121: ¹H NMR (400 MHz, CDCl₃) δ 9.14 (dd, J=3.0, 0.5 Hz, 1H), 8.93 (s, 1H), 8.85-8.61 (m, 1H), 8.21 (dt, J=15.0, 3.0 Hz, 1H), 8.02-7.63 (m, 4H), 7.58-7.30 (m, 2H), 7.22-7.09 (m, 2H), 6.95 (dd, J=15.0, 10.1 Hz, 1H), 4.93 (s, 1H). Mass spectrum (ESI, m/z): C21H15FN4O2, [M+H]⁺: 375.12.

BRM2-122: ¹H NMR (400 MHz, CDCl₃) δ 8.78 (s, 1H), 8.05 (s, 1H), 7.93-7.65 (m, 4H), 7.35 (dd, J=16.0, 2.9 Hz, 1H), 7.28-7.01 (m, 2H), 6.95 (dd, J=15.0, 10.1 Hz, 1H), 4.94 (s, 1H), 2.43 (s, 3H). Mass spectrum (ESI, m/z): C20H15FN4O3, [M+H]⁺: 379.11.

BRM2-123: ¹H NMR (400 MHz, CDCl₃) δ 8.95 (s, 1H), 8.43 (d, J=15.0 Hz, 1H), 8.08-7.72 (m, 5H), 7.62 (d, J=2.9 Hz, 1H), 7.35 (dd, J=16.0, 2.9 Hz, 1H), 7.27-7.03 (m, 2H), 6.95 (dd, J=15.0, 10.1 Hz, 1H), 4.93 (s, 1H). Mass spectrum (ESI, m/z): C21H2OClFN4O2, [M+H]⁺: 409.08.

BRM2-124: ¹H NMR (400 MHz, CDCl₃) δ 9.96 (s, 1H), 9.10 (d, J=15.0 Hz, 1H), 8.89 (d, J=15.0 Hz, 1H), 8.78 (s, 1H), 8.07-7.58 (m, 4H), 7.35 (dd, J=16.0, 2.9 Hz, 1H), 7.22-7.06 (m, 2H), 6.97-6.69 (m, 1H), 4.90 (s, 1H). Mass spectrum (ESI, m/z): C20H14FN5O2, [M+H]⁺: 376.11.

BRM2-125: ¹H NMR (400 MHz, CDCl₃) δ 8.96 (s, 1H), 7.97-7.66 (m, 4H), 7.35 (dd, J=16.0, 2.9 Hz, 1H), 7.20-7.01 (m, 2H), 6.95 (dd, J=15.0, 10.1 Hz, 1H), 6.46 (dt, J=6.9, 2.5 Hz, 3H), 4.93 (s, 1H), 3.77 (s, 6H). Mass spectrum (ESI, m/z): C24H20FN3O4, [M+H]⁺: 434.14.

BRM2-126: ¹H NMR (400 MHz, CDCl₃) δ 8.23 (s, 1H), 8.05-7.58 (m, 4H), 7.44-7.15 (m, 1H), 7.31-6.82 (m, 3H), 4.31 (s, 1H), 2.32 (td, J=15.0, 0.8 Hz, 2H), 2.00-1.50 (m, 2H), 0.98 (t, J=13.1 Hz, 3H). Mass spectrum (ESI, m/z): C19H18FN3O2, [M+H]⁺: 340.14.

BRM2-127: ¹H NMR (400 MHz, CDCl₃) δ 8.19 (s, 1H), 7.93-7.59 (m, 4H), 7.35 (dd, J=16.0, 2.9 Hz, 1H), 7.18-7.06 (m, 2H), 6.95 (dd, J=15.0, 10.1 Hz, 1H), 4.93 (s, 1H), 1.23 (s, 9H). Mass spectrum (ESI, m/z): C20H20FN3O2, [M+H]⁺: 354.15.

BRM2-128: ¹H NMR (400 MHz, CDCl₃) δ 8.99 (s, 1H), 8.07-7.69 (m, 4H), 7.46-7.03 (m, 8H), 6.95 (dd, J=15.0, 10.1 Hz, 1H), 4.95 (s, 1H), 3.23-2.68 (m, 4H). Mass spectrum (ESI, m/z): C24H20FN3O2, [M+H]⁺: 402.15.

BRM2-129: ¹H NMR (400 MHz, CDCl₃) δ 7.32 (dd, J=16.0, 2.9 Hz, 1H), 7.21-7.01 (m, 2H), 6.92 (dd, J=14.9, 10.0 Hz, 1H), 5.93 (s, 1H), 4.88 (s, 1H), 3.55 (p, J=15.2 Hz, 1H), 2.80-2.24 (m, 4H), 2.17 (s, 3H), 1.83 (dddt, J=62.2, 24.8, 15.3, 11.1 Hz, 4H). Mass spectrum (ESI, m/z): C16H19FN4O2, [M+H]⁺: 319.15.

BRM2-130: ¹H NMR (400 MHz, CDCl₃) δ 9.09 (s, 1H), 7.61-7.03 (m, 4H), 7.03-6.58 (m, 4H), 4.91 (s, 1H), 3.44 (t, J=10.3 Hz, 4H), 2.35 (t, J=10.3 Hz, 4H), 2.21 (s, 3H). Mass spectrum (ESI, m/z): C21H22FN5O2, [M+H]⁺: 396.18.

BRM2-131: ¹H NMR (400 MHz, CDCl₃) δ 7.80 (d, J=15.0 Hz, 1H), 7.35 (dd, J=16.0, 2.9 Hz, 1H), 7.25-6.99 (m, 2H), 7.04-6.72 (m, 2H), 4.45 (s, 1H), 3.94 (s, 3H). Mass spectrum (ESI, m/z): C14H12FN5O2, [M+H]⁺: 302.10.

BRM2-132: ¹H NMR (400 MHz, CDCl₃) δ 8.04 (dd, J=15.0, 2.9 Hz, 1H), 7.55 (td, J=15.0, 3.0 Hz, 1H), 7.35 (dd, J=16.0, 2.9 Hz, 1H), 7.27-6.87 (m, 4H), 6.73 (td, J=15.0, 3.0 Hz, 1H), 4.87 (s, 1H), 3.99 (t, J=10.0 Hz, 4H), 3.36 (t, J=10.0 Hz, 4H). Mass spectrum (ESI, m/z): C19H18FN5O2, [M+H]⁺: 368.14.

BRM2-133: ¹H NMR (400 MHz, CDCl₃) δ 7.33 (dd, J=16.0, 2.9 Hz, 1H), 7.22-7.00 (m, 2H), 6.93 (dd, J=15.0, 10.1 Hz, 1H), 4.87 (s, 1H), 3.42-2.96 (m, 6H), 2.81 (t, J=10.1 Hz, 2H), 2.17 (s, 3H), 2.02-1.55 (m, 2H). Mass spectrum (ESI, m/z): C16H19FN4O2, [M+H]⁺: 319.15.

BRM2-134: ¹H NMR (400 MHz, CDCl₃) δ 7.35 (dd, J=16.0, 3.0 Hz, 1H), 7.15-7.04 (m, 2H), 6.94 (dd, J=15.0, 10.1 Hz, 1H), 4.91 (s, 1H), 3.52-2.97 (m, 8H), 1.42 (s, 9H). Mass spectrum (ESI, m/z): C19H23FN4O4, [M+H]⁺: 391.17.

BRM2-135: ¹H NMR (400 MHz, CDCl₃) δ 7.35 (dd, J=16.0, 2.9 Hz, 1H), 7.24-7.02 (m, 2H), 6.95 (dd, J=15.0, 10.1 Hz, 1H), 6.29 (s, 1H), 4.92 (s, 1H), 3.75-3.32 (m, 4H), 3.11-2.88 (m, 2H), 2.21-1.78 (m, 3H), 1.55 (ddt, J=24.8, 15.3, 11.1 Hz, 2H), 1.42 (s, 9H). Mass spectrum (ESI, m/z): C21H27FN4O4, [M+H]⁺: 419.20.

BRM2-136: ¹H NMR (400 MHz, CDCl₃) δ 7.53-7.20 (m, 3H), 7.27-6.89 (m, 5H), 6.82 (s, 1H), 4.83 (s, 1H), 4.11 (s, 2H). Mass spectrum (ESI, m/z): C17H13F2N3O2, [M+H]⁺: 330.10.

BRM2-137: ¹H NMR (400 MHz, CDCl₃) δ 7.35 (dd, J=16.0, 2.9 Hz, 1H), 7.21-6.82 (m, 5H), 6.78-6.55 (m, 2H), 6.35 (s, 1H), 4.65 (d, J=50.8 Hz, 2H), 3.37 (td, J=15.4, 0.8 Hz, 2H), 2.79 (td, J=15.4, 0.8 Hz, 2H) Mass spectrum (ESI, m/z): C18H16FN3O3, [M+H]⁺: 342.12.

BRM2-138: ¹H NMR (400 MHz, CDCl₃) δ 7.35 (dd, J=16.0, 2.9 Hz, 1H), 7.24 (s, 1H), 7.14 (dd, J=15.1, 2.9 Hz, 1H), 7.10-7.02 (m, 1H), 6.99-6.89 (m, 3H), 6.82-6.66 (m, 2H), 4.64 (s, 1H), 4.11 (s, 2H). Mass spectrum (ESI, m/z): C17H14FN3O3, [M+H]⁺: 328.10.

BRM2-139: ¹H NMR (400 MHz, 6d-DMSO) δ 8.98 (s, 1H), 7.62-7.22 (m, 3H), 7.27-6.80 (m, 7H), 3.31 (t, J=10.4 Hz, 2H), 2.90 (t, J=10.4 Hz, 2H). Mass spectrum (ESI, m/z): C20H17FN4O2, [M+H]⁺: 365.13.

BRM2-140: ¹H NMR (400 MHz, 6d-DMSO) δ 8.98 (s, 1H), 7.46-7.27 (m, 3H), 7.18-6.83 (m, 6H), 3.37 (td, J=15.4, 0.8 Hz, 2H), 2.79 (td, J=15.4, 0.8 Hz, 2H). Mass spectrum (ESI, m/z): C18H15ClFN3O2, [M+H]⁺: 360.08.

BRM2-141: ¹H NMR (400 MHz, 6d-DMSO) δ 8.98 (s, 1H), 7.35 (dd, J=16.0, 2.9 Hz, 1H), 7.31-7.07 (m, 6H), 7.03 (t, J=8.2 Hz, 2H), 6.98 (dd, J=15.0, 10.1 Hz, 1H), 3.37 (td, J=15.4, 0.8 Hz, 2H), 2.79 (td, J=15.4, 0.8 Hz, 2H). Mass spectrum (ESI, m/z): C18H16FN3O2, [M+H]⁺: 326.12.

BRM2-142: ¹H NMR (400 MHz, 6d-DMSO) δ 8.98 (s, 1H), 7.48-7.14 (m, 1H), 7.25-6.65 (m, 4H), 3.25 (t, J=15.2 Hz, 2H), 1.75-1.20 (m, 2H), 0.88 (t, J=13.2 Hz, 3H). Mass spectrum (ESI, m/z): C13H14FN3O3, [M+H]⁺: 264.11.

BRM2-143: ¹H NMR (400 MHz, 6d-DMSO) δ 7.37-7.12 (m, 3H), 7.10-6.78 (m, 6H), 4.61 (s, 3H), 3.19 (s, 3H). Mass spectrum (ESI, m/z): C18H16FN3O2, [M+H]⁺: 326.12.

BRM2-144: ¹H NMR (400 MHz, 6d-DMSO) δ 7.45-7.22 (m, 3H), 7.20-6.91 (m, 6H), 4.67 (s, 3H), 3.07 (q, J=12.6 Hz, 2H), 1.17 (t, J=12.6 Hz, 3H). Mass spectrum (ESI, m/z): C19H18FN3O3, [M+H]⁺: 340.14.

BRM2-145: ¹H NMR (400 MHz, 6d-DMSO) δ 7.43-7.25 (m, 6H), 7.19-7.03 (m, 3H), 6.98 (dd, J=15.0, 10.1 Hz, 1H), 4.67 (s, 2H), 3.77 (hept, J=12.0 Hz, 1H), 1.26 (d, J=12.0 Hz, 6H). Mass spectrum (ESI, m/z): C20H20FN3O3, [M+H]⁺: 354.15.

BRM2-146: ¹H NMR (400 MHz, 6d-DMSO) δ 7.43 (d, J=8.9 Hz, 1H), 7.41-7.20 (m, 11H), 7.18-6.87 (m, 3H), 4.67 (s, 4H). Mass spectrum (ESI, m/z): C24H20FN3O3, [M+H]⁺: 402.15.

BRM2-147: ¹H NMR (400 MHz, 6d-DMSO) δ 9.38 (s, 1H), 7.33 (dt, J=25.8, 12.9 Hz, 1H), 7.28-6.70 (m, 9H), 4.81 (t, J=14.2 Hz, 1H), 3.66 (s, 3H), 3.10 (ddd, J=103.0, 24.8, 14.2 Hz, 2H). Mass spectrum (ESI, m/z): C20H18FN3O4, [M+H]⁺: 384.13.

BRM2-148: ¹H NMR (400 MHz, 6d-DMSO) δ 9.38 (s, 1H), 7.35 (dd, J=16.0, 2.9 Hz, 1H), 7.22-6.76 (m, 4H), 4.51 (t, J=12.9 Hz, 1H), 3.66 (s, 3H), 2.60 (td, J=16.0, 1.3 Hz, 2H), 2.38-1.88 (m, 5H). Mass spectrum (ESI, m/z): C16H18FN3O4S, [M+H]⁺: 368.10.

BRM2-149: ¹H NMR (400 MHz, 6d-DMSO) δ 9.38 (s, 1H), 7.56-7.30 (m, 2H), 7.27-6.78 (m, 3H), 4.51 (t, J=6.6 Hz, 1H), 3.66 (s, 3H), 2.89 (dd, J=17.4, 6.1 Hz, 2H), 2.80 (s, 3H), 2.56-2.42 (m, 2H). Mass spectrum (ESI, m/z): C16H18FN3O6S, [M+H]⁺: 400.09.

BRM2-150: ¹H NMR (400 MHz, 6d-DMSO) δ 7.35 (dd, J=16.0, 2.9 Hz, 1H), 7.22-6.87 (m, 4H), 4.43-4.08 (m, 1H), 4.01-3.17 (m, 5H), 2.40-1.86 (m, 2H), 1.83-1.43 (m, 2H). Mass spectrum (ESI, m/z): C16H16FN3O4, [M+H]⁺: 334.11.

BRM2-151: ¹H NMR (400 MHz, 6d-DMSO) δ 9.38 (s, 1H), 9.05 (s, 1H), 7.35 (dd, J=16.0, 2.9 Hz, 1H), 7.28-6.85 (m, 6H), 6.75-6.50 (m, 2H), 4.81 (t, J=6.9 Hz, 1H), 3.11 (ddd, J=103.0, 24.8, 6.8 Hz, 2H). Mass spectrum (ESI, m/z): C20H18FN3O5, [M+H]⁺: 400.12.

BRM2-152: ¹H NMR (400 MHz, 6d-DMSO) δ 9.38 (s, 1H), 8.47 (d, J=0.5 Hz, 1H), 7.35 (dd, J=16.0, 1.6 Hz, 2H), 7.21-6.78 (m, 4H), 4.68 (t, J=7.8 Hz, 1H), 3.66 (s, 3H), 3.10 (dd, J=24.8, 7.8 Hz, 1H), 2.44 (dd, J=24.8, 7.8 Hz, 1H). Mass spectrum (ESI, m/z): C17H16FN5O4, [M+H]⁺: 374.12.

BRM2-153: ¹H NMR (400 MHz, 6d-DMSO) δ 9.34 (s, 1H), 7.32 (dd, J=16.0, 2.9 Hz, 1H), 7.17-6.80 (m, 4H), 4.19 (d, J=4.8 Hz, 1H), 3.64 (s, 3H), 2.80 (tqd, J=15.5, 13.0, 4.8 Hz, 1H), 1.78-1.37 (m, 2H), 1.21-0.75 (m, 6H). Mass spectrum (ESI, m/z): C17H20FN3O4, [M+H]⁺: 350.14.

BRM2-154: ¹H NMR (400 MHz, 6d-DMSO) δ 9.38 (s, 1H), 7.46-7.24 (m, 1H), 7.28-6.76 (m, 9H), 5.11 (t, J=12.2 Hz, 1H), 3.98-3.42 (m, 4H), 3.39-2.83 (m, 2H), 2.14-1.67 (m, 4H). Mass spectrum (ESI, m/z): C23H23FN4O3, [M+H]⁺: 423.18.

BRM2-155: ¹H NMR (400 MHz, 6d-DMSO) δ 9.38 (s, 1H), 7.35 (dd, J=16.0, 2.9 Hz, 1H), 7.32-7.21 (m, 1H), 7.15-6.92 (m, 7H), 4.81 (t, J=11.7 Hz, 1H), 3.64 (tdd, J=10.2, 8.3, 3.9 Hz, 6H), 3.51-3.12 (m, 3H), 3.04 (dd, J=24.8, 11.7 Hz, 1H). Mass spectrum (ESI, m/z): C23H23FN4O4, [M+H]⁺: 439.17.

BRM2-156: ¹H NMR (400 MHz, 6d-DMSO) δ 9.33 (s, 1H), 7.31 (dd, J=16.0, 2.9 Hz, 1H), 7.17-6.62 (m, 4H), 6.11 (s, 2H), 4.67-4.26 (m, 1H), 3.75 (dd, J=9.9, 8.6 Hz, 2H), 3.59 (dd, J=9.8, 8.8 Hz, 4H), 3.39 (d, J=9.7, 8.8 Hz, 2H), 2.40-1.76 (m, 4H). Mass spectrum (ESI, m/z): C19H22FN5O5, [M+H]⁺: 420.16.

BRM2-157: ¹H NMR (400 MHz, 6d-DMSO) δ 8.98 (s, 1H), 7.35 (dd, J=16.0, 2.9 Hz, 1H), 7.28-6.75 (m, 8H), 3.37 (td, J=15.4, 0.8 Hz, 2H), 2.79 (td, J=15.4, 0.8 Hz, 2H). Mass spectrum (ESI, m/z): C18H15F2N3O2, [M+H]⁺: 344.11.

BRM2-158: ¹H NMR (400 MHz, 6d-DMSO) δ 8.98 (s, 1H), 7.35 (dd, J=16.0, 2.9 Hz, 1H), 7.22-6.75 (m, 3H), 4.26 (dd, J=103.0, 24.8 Hz, 4H), 0.92 (s, 3H). Mass spectrum (ESI, m/z): C15H16FN3O3, [M+H]⁺: 306.12.

BRM2-159: ¹H NMR (400 MHz, 6d-DMSO) δ 8.98 (s, 1H), 8.21-7.73 (m, 2H), 7.35 (dd, J=16.0, 2.9 Hz, 1H), 7.21-6.85 (m, 6H), 6.08 (s, 2H), 3.37 (t, J=10.2 Hz, 2H), 2.79 (t, J=10.2 Hz, 2H). Mass spectrum (ESI, m/z): C19H17FN4O3, [M+H]⁺: 369.13.

BRM2-160: ¹H NMR (400 MHz, 6d-DMSO) δ 7.35 (dd, J=7.9, 1.4 Hz, 1H), 7.12 (td, J=7.8, 1.4 Hz, 1H), 7.05 (s, 1H), 6.98 (dd, J=7.4, 5.0 Hz, 1H), 5.99 (s, 2H), 5.57 (s, 1H). Mass spectrum (ESI, m/z): C9H8FN3O, [M+H]⁺: 194.07.

BRM2-161: ¹H NMR (400 MHz, 6d-DMSO) δ7.35 (dd, J=16.0, 2.9 Hz, 1H), 7.23-6.84 (m, 3H), 5.74 (s, 1H), 2.36 (td, J=16.1, 0.7 Hz, 2H), 1.89-1.38 (m, 2H), 0.98 (t, J=13.1 Hz, 3H). Mass spectrum (ESI, m/z): C13H14FN3O2, [M+H]⁺: 264.11.

BRM2-162: ¹H NMR (400 MHz, 6d-DMSO) δ 8.03-7.80 (m, 1H), 7.73-7.45 (m, 2H), 7.45-7.25 (m, 1H), 7.24-6.85 (m, 2H), 5.99 (s, 1H). Mass spectrum (ESI, m/z): C16H12FN3O2, [M+H]⁺: 298.09.

BRM2-163: ¹H NMR (400 MHz, 6d-DMSO) δ 9.68 (s, 1H), 7.92-7.58 (m, 2H), 7.35 (dd, J=16.0, 2.9 Hz, 1H), 7.24-6.72 (m, 5H), 5.98 (s, 1H). Mass spectrum (ESI, m/z): C16H12FN3O3, [M+H]⁺: 314.09.

BRM2-164: ¹H NMR (400 MHz, 6d-DMSO) δ 9.05 (s, 1H), 7.35 (dd, J=16.0, 2.9 Hz, 1H), 7.26-6.78 (m, 5H), 6.78-6.56 (m, 2H), 5.83 (s, 1H), 3.80 (s, 2H). Mass spectrum (ESI, m/z): C17H14FN3O3, [M+H]⁺: 328.10.

BRM2-165: ¹H NMR (400 MHz, 6d-DMSO) δ 9.14 (dd, J=3.0, 0.5 Hz, 1H), 8.92-8.60 (m, 1H), 8.30 (dt, J=15.0, 3.0 Hz, 1H), 7.59 (t, J=15.0 Hz, 1H), 7.50-7.30 (m, 1H), 7.25-6.80 (m, 3H), 5.37 (s, 1H). Mass spectrum (ESI, m/z): C15H11FN4O2, [M+H]⁺: 299.09.

BRM2-166: ¹H NMR (400 MHz, 6d-DMSO) δ 9.96 (s, 1H), 9.10 (d, J=15.0 Hz, 1H), 8.89 (d, J=15.0 Hz, 1H), 7.32 (dt, J=46.6, 23.3 Hz, 1H), 7.27-6.55 (m, 3H), 5.80 (s, 1H). Mass spectrum (ESI, m/z): C14H10FN5O2, [M+H]⁺: 300.08.

BRM2-167: ¹H NMR (400 MHz, 6d-DMSO) δ 9.05 (s, 1H), 7.35 (dd, J=16.0, 2.9 Hz, 1H), 7.20-6.86 (m, 5H), 6.76-6.54 (m, 2H), 5.65 (s, 1H), 3.25-2.49 (m, 4H). Mass spectrum (ESI, m/z): C18H16FN3O3, [M+H]⁺: 342.12.

BRM2-168: ¹H NMR (400 MHz, 6d-DMSO) δ 7.50-7.21 (m, 2H), 7.27-6.85 (m, 4H), 5.85 (s, 2H), 3.80 (s, 2H). Mass spectrum (ESI, m/z): C17H13F2N3O2, [M+H]⁺: 330.10.

BRM2-169: ¹H NMR (400 MHz, 6d-DMSO) δ 8.11-7.70 (m, 1H), 7.55-7.24 (m, 2H), 7.30-6.50 (m, 5H), 5.99 (s, 1H). Mass spectrum (ESI, m/z): C16H12FN3O3, [M+H]⁺: 314.09.

BRM2-170: ¹H NMR (400 MHz, 6d-DMSO) δ 7.91-7.72 (m, 1H), 7.72-7.49 (m, 1H), 7.35 (dd, J=16.0, 2.9 Hz, 1H), 7.15-6.68 (m, 1H), 5.69 (s, 1H). Mass spectrum (ESI, m/z): C17H11F4N3O2, [M+H]⁺: 366.08.

BRM2-171: ¹H NMR (400 MHz, 6d-DMSO) δ 8.19-7.86 (m, 1H), 7.77-7.49 (m, 1H), 7.35 (dd, J=16.0, 2.9 Hz, 1H), 7.17-6.65 (m, 1H), 5.98 (s, 1H). Mass spectrum (ESI, m/z): C16H11BrFN3O3, [M+H]⁺: 376.00.

BRM2-172: ¹H NMR (400 MHz, 6d-DMSO) δ 7.42 (d, J=15.0 Hz, 1H), 7.35 (dd, J=16.0, 2.9 Hz, 1H), 7.21-7.07 (m,

1H), 7.06-6.91 (m, 2H), 6.70 (d, J=15.0 Hz, 1H), 6.00 (s, 1H). Mass spectrum (ESI, m/z): C13H10FN5O2, [M+H]⁺: 288.08.

BRM2-173: ¹H NMR (400 MHz, 6d-DMSO) δ 7.44 (dd, J=7.9, 1.4 Hz, 1H), 7.35 (dd, J=7.9, 1.4 Hz, 1H), 7.27 (td, J=7.8, 1.4 Hz, 1H), 7.12 (td, J=7.8, 1.4 Hz, 1H), 7.05 (s, 1H), 6.97 (ddd, J=7.6, 4.9, 3.9 Hz, 2H), 6.00 (s, 1H). Mass spectrum (ESI, m/z): C16H11F2N3O2, [M+H]⁺: 332.08.

BRM2-174: ¹H NMR (400 MHz, 6d-DMSO) δ 7.35 (dd, J=16.0, 2.9 Hz, 1H), 7.22-7.07 (m, 1H), 7.05 (s, 1H), 6.98 (dd, J=15.0, 10.1 Hz, 1H), 5.73 (s, 1H). Mass spectrum (ESI, m/z): C16H12FN3O3, [M+H]⁺: 314.09. Mass spectrum (ESI, m/z): C18H13F2N5O2, [M+H]⁺: 370.10.

Example 9

Determining the Pharmacodynamic Activity of the Compounds of the Present Invention by a Cell Viability Test Method A tetrazolium salt (MTT) method is used for determining the pharmacodynamics activity of the compounds of the present invention by using H1299 cells as the cell line, wherein the cell line has deletion of the BRG1 gene (BRG1−), and has no deletion of the BRM gene (BRM+). That is, the cells of the cell line cannot express a BRG1 protein, but can normally express a BRM protein. Small molecules that could prevent the BRM protein from interacting with the chromosomes in the cells, could prevent the BRM protein from exerting functions in the cells. According to the law of synergistic lethality, in a BRG1-gene-deleted cell, if the function of the BRM protein is blocked, cell death will be caused, thereby achieving the function that the small molecules kill cancer cells.

The specific steps of the test are as follows:
(1) different experimental cell lines are subcultured into a 96-well plate, and to prevent a marginal effect, the peripheries of the 96-well plate are added with 100 μL of PBS as a blank, wherein the cell line as used is H1299 cells (BRG1−/BRM+cell line);
(2) when the cells are in adherent growth to be 40-50%, different concentrations of drug molecules and DMSO as controls are added, the cells treated with the small molecules continue to be cultured for 3-4 days, and the medium is replaced by a medium supplemented with small molecules during the culture;
(3) after the 96-well plate treated with DMSO in the control group is full of the cells, each well is added with 20 μL of a MTT mother liquor (5 mg/mL);
(4) the cell plate is placed back into a C2O incubator of 37° C. and continue to be incubated for 4 hours;
(5) the MTT solution is pipetted off, and each well is added with 150 μL DMSO;
(6) the 96-well plate is placed in a shaker at room temperature with protection from light for 15 min, until purple crystals are completely dissolved.
(7) The absorbance (OD) of each well is determined by a SpectraMax M5 multi-well plate reader (Molecular Devices, USA) at a wavelength of 490 nm.

According to a conventional detection method, the EC50 values of respective compounds (small molecules) are determined, and the results are summarized in Table 1.

TABLE 1

| Compound No. | Structure of Compound | Ki (μM) | EC50 (μM) |
| --- | --- | --- | --- |
| BRM2-4 | | 1.8 | 6.7 |
| BRM2-6 | | 2.3 | 12.0 |
| BRM2-8 | | 2.2 | 8.5 |

TABLE 1-continued

| Compound No. | Structure of Compound | Ki (μM) | EC50 (μM) |
|---|---|---|---|
| BRM2-9 | | 4.6 | >20 |
| BRM2-11 | | 1.6 | >20 |
| BRM2-22 | | 1.5 | 3.3 |
| BRM2-27 | | 2.7 | >20 |
| BRM2-30 | | 2.0 | 10.5 |
| BRM2-31 | | 0.9 | 1.7 |
| BRM2-32 | | 3.7 | 5.8 |

TABLE 1-continued
| Compound No. | Structure of Compound | Ki (μM) | EC50 (μM) |
|---|---|---|---|
| BRM2-33 | 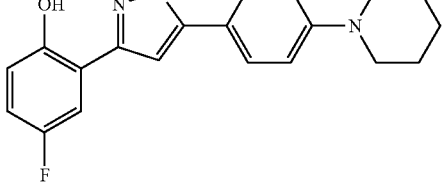 | 2.7 | 15.0 |
| BRM2-34 | 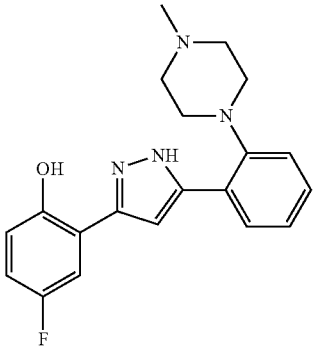 | 1.4 | 7.6 |
| BRM2-39 | 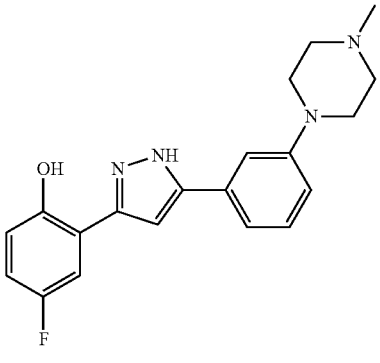 | 1.8 | 9.3 |
| BRM2-41 | 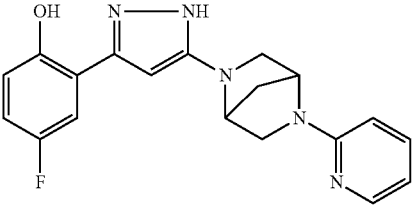 | 2.7 | 13.5 |
| BRM2-105 | 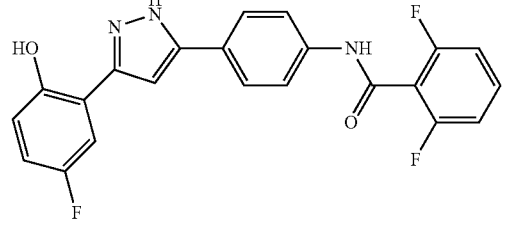 | 4.1 | >20 |

TABLE 1-continued

| Compound No. | Structure of Compound | Ki (μM) | EC50 (μM) |
|---|---|---|---|
| BRM2-106 | | 0.2 | 0.9 |
| BRM2-111 | | 0.8 | 3.8 |
| BRM2-112 | | 0.9 | 6.5 |
| BRM2-113 | | 2.0 | >20 |
| BRM2-114 | | 3.0 | 11.4 |
| BRM2-121 | | 0.6 | 2.4 |

TABLE 1-continued
| Compound No. | Structure of Compound | Ki (μM) | EC50 (μM) |
|---|---|---|---|
| BRM2-123 | 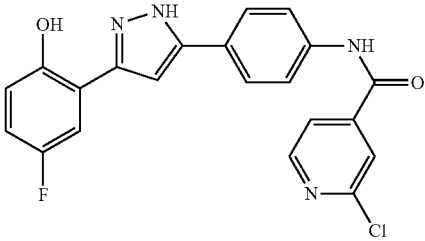 | 0.7 | 2.8 |
| BRM2-124 | 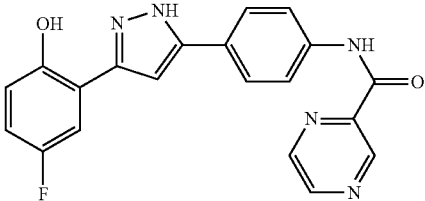 | 0.6 | 1.5 |
| BRM2-136 | 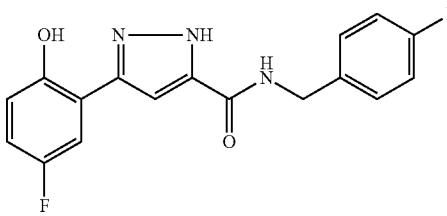 | 3.0 | 18.0 |
| BRM2-137 | 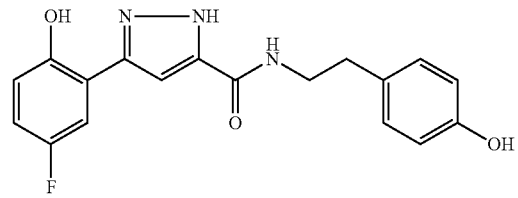 | 1.1 | >20 |
| BRM2-138 | 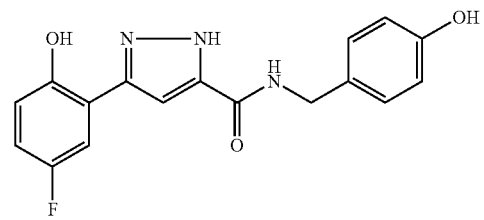 | 2.0 | >20 |
| BRM2-140 | 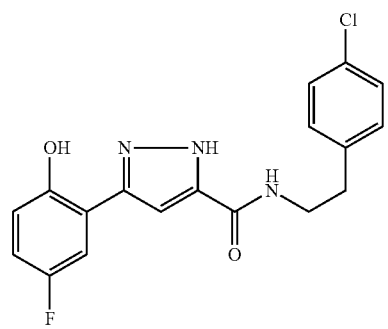 | 2.0 | 14.7 |

TABLE 1-continued

| Compound No. | Structure of Compound | Ki (μM) | EC50 (μM) |
|---|---|---|---|
| BRM2-143 | | 2.8 | 17.3 |
| BRM2-144 | | 4.6 | >20 |
| BRM2-145 | | 5.3 | >20 |
| BRM2-149 | | 1.2 | 8.9 |
| BRM2-150 | | 1.8 | 10.3 |
| BRM2-152 | | 0.5 | 2.5 |

TABLE 1-continued

| Compound No. | Structure of Compound | Ki (μM) | EC50 (μM) |
|---|---|---|---|
| BRM2-156 | | 0.4 | 1.7 |
| BRM2-157 | | 0.8 | 4.3 |
| BRM2-160 | | 3.2 | 18.2 |
| BRM2-162 | | 6.8 | >20 |
| BRM2-163 | | 4.4 | 17.2 |
| BRM2-164 | | 6.9 | >20 |

TABLE 1-continued

| Compound No. | Structure of Compound | Ki (μM) | EC50 (μM) |
|---|---|---|---|
| BRM2-166 | 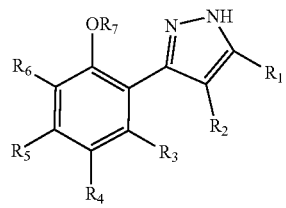 | 1.7 | 7.3 |
| BRM2-168 | | 2.5 | 13.4 |

The invention claimed is:

1. A compound represented by Formula (I) or a pharmaceutically acceptable salt, stereoisomer, ether, ester, prodrug and solvate thereof (I)

wherein, when $R_1$ is

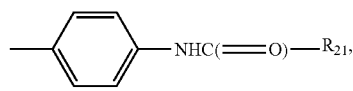

wherein $R_2$ is H, $R_3$ is H, $R_4$ is F, $R_5$ is H, $R_6$ is H, $R_7$ is H and $R_{21}$ is selected from the group consisting of heterocyclic rings or substituted phenyl.

2. The compound or the pharmaceutically acceptable salt, stereoisomer, ether, ester, prodrug and solvate thereof according claim 1, characterized in that the compound has the following structures:

BRM2-96
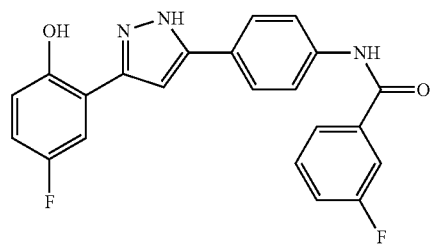

BRM2-97
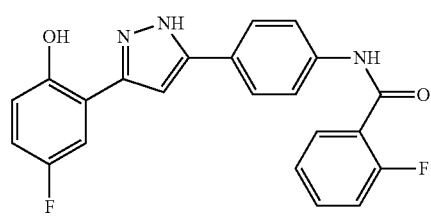

BRM2-98
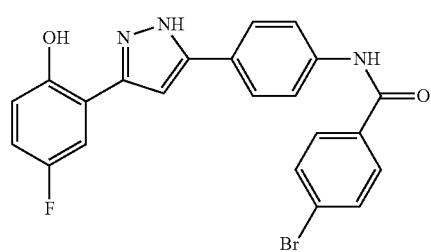

BRM2-99
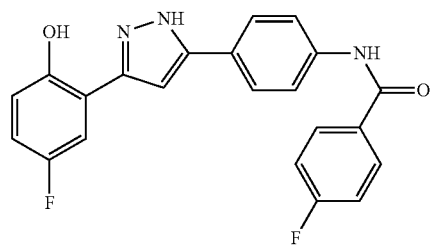

BRM2-100
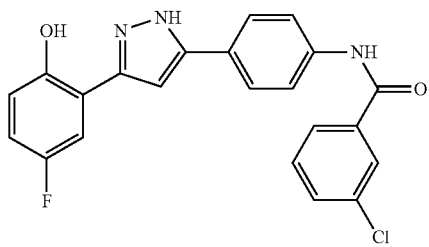
BRM2-101
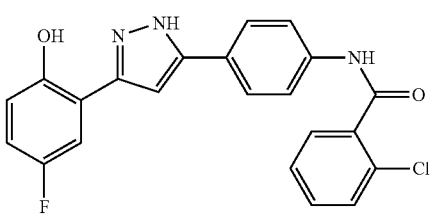
BRM2-102
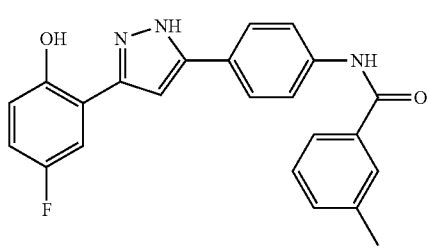
BRM2-103
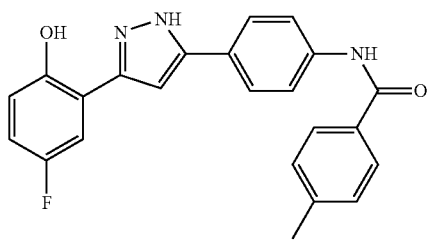
BRM2-104
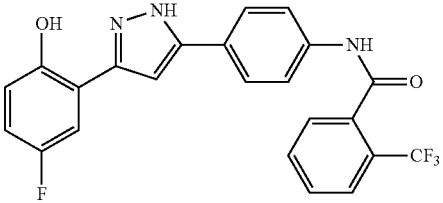
BRM2-105
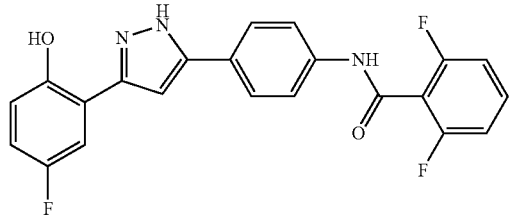
BRM2-107
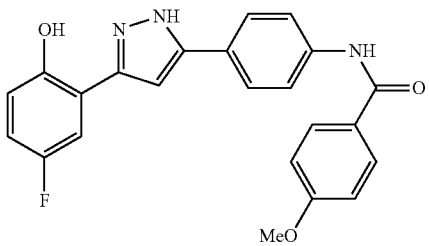
BRM2-109
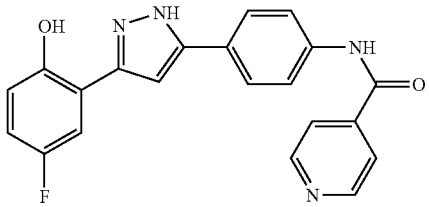
BRM2-111
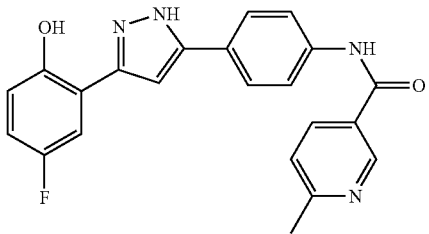
BRM2-112
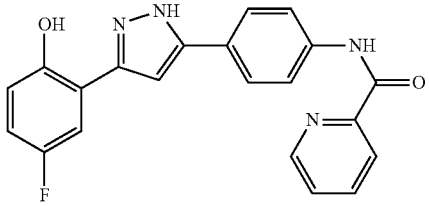
BRM2-113
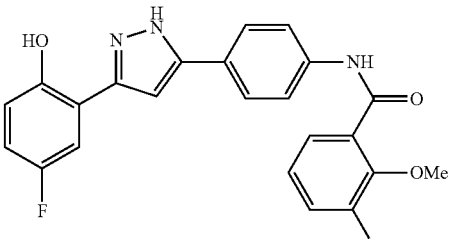
BRM2-114
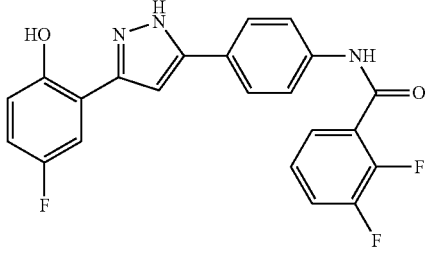

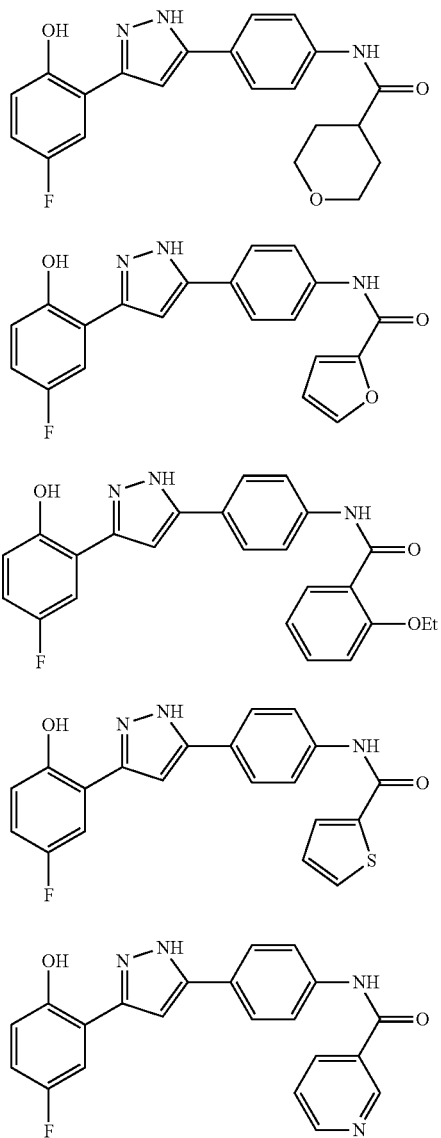
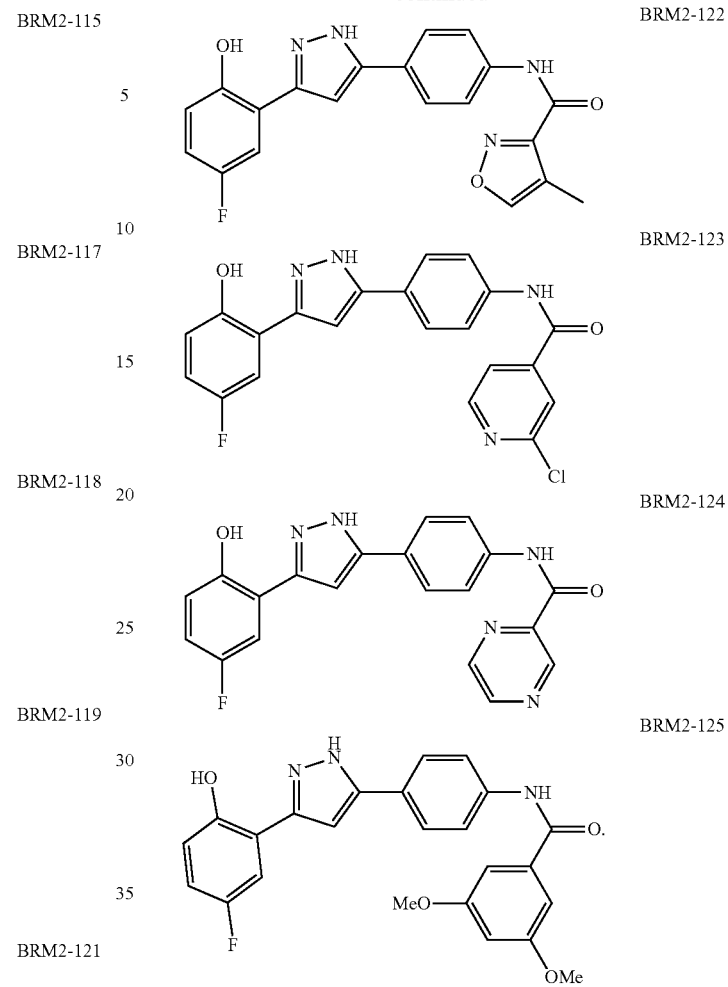
3. A pharmaceutical composition, comprising the compound represented by Formula (I) or the pharmaceutically acceptable salt, stereoisomer, ether, ester, prodrug, solvate thereof according to claim 1, and a pharmaceutically acceptable auxiliary material.
* * * * *